United States Patent
Marzabadi et al.

(10) Patent No.: US 6,225,330 B1
(45) Date of Patent: May 1, 2001

(54) SELECTIVE NPY (Y5) ANTAGONISTS (TRICYCLICS)

(75) Inventors: Mohammad R. Marzabadi, Ridgewood, NJ (US); Wai C. Wong, Hamden, CT (US); Walter Schilling, Himmelried (CH); Stewart A. Noble, Wheeling, IL (US)

(73) Assignees: Synaptic Pharmaceutical Corporation, Paramus, NJ (US); Novartis AG, Basel (CH)

( * ) Notice: Subject to any disclaimer, the term of this patent is extended or adjusted under 35 U.S.C. 154(b) by 0 days.

(21) Appl. No.: 09/343,635

(22) Filed: Jun. 30, 1999

(51) Int. Cl.[7] .................. C07D 277/60; A61K 31/428
(52) U.S. Cl. ................... 514/360; 544/133; 546/270; 548/150; 548/151
(58) Field of Search .................. 548/150, 151; 514/366; 546/270; 544/133

(56) References Cited

U.S. PATENT DOCUMENTS

| | | |
|---|---|---|
| 4,383,113 | 5/1983 | Levitt et al. . |
| 5,166,214 | 11/1992 | Billheimer . |
| 5,232,921 | 8/1993 | Biziere et al. . |
| 5,238,936 | 8/1993 | Reginier et al. . |
| 5,536,722 | 7/1996 | Coe et al. . |
| 5,550,138 * | 8/1996 | Sohda .................. 514/361 |

FOREIGN PATENT DOCUMENTS

| | | |
|---|---|---|
| 0448078 | 9/1991 | (EP) . |
| 0283390 | 3/1993 | (EP) . |
| 0432040 | 7/1994 | (EP) . |
| 0775487 | 5/1997 | (EP) . |
| 57151653 | 9/1992 | (JP) . |
| 9323381 | 11/1993 | (WO) . |
| 9418212 | 8/1994 | (WO) . |
| 9619457 | 6/1997 | (WO) . |
| 9720823 | 6/1997 | (WO) . |
| 9835944 | 8/1998 | (WO) . |
| 9835957 | 8/1998 | (WO) . |
| 9905138 | 2/1999 | (WO) . |
| 9932466 | 7/1999 | (WO) . |
| 9962829 | 12/1999 | (WO) . |

OTHER PUBLICATIONS

Berlin, K. Darrell and Melvin D. Herd, "Novel 2–Amino–4, 5–Aryl–Substituted– and 2–Amino–4–Disubstituted–Thiazoles", *Proc. Okla. Acad. Sci.* 71: 29–33 (1991) (Exhibit 9);.

Ohkubo, M., et al., "Studies on Cerebral Protective Agents. VIII. Synthesis of 2–Aminothiazoles and 2–Thiazolecarboxamides with Anti–anoxic Activity", *Chem. Pharm. Bull.*, 43 (9): 1497–1504 (1995) (Exhibit 10);.

Peesapati, V. and N. Lingaiah, "Thiopheno [3,2] [1] Benzazepine, Benzo [3,4] Cyclohepta [2,1–b] Thiophenes, Thiazolo [5,4–d] Benzazepine and Benzo [3,4] Cyclohepta [2,1–d] Thiazoles", *OPPI Briefs*, 25 (5) : 602–606 (1993) (Exhibit 11);.

Yamane, Kameji, *Nippon Kagaku Zasshi* 91 (4) : 395–399 (1970) (Exhibit 12);.

Yamane, et al., *Nippon Kagaku Zasshi* 90 (6) : 569–571 (1969) (Exhibit 13); and.

Yamane, et al., *Nippon Kagaku Zasshi* 89 (6) : 612–614 (1968) (Exhibit 14).

Brown, et al., *Aust. J. Chem.*, 34: 2423–2429 (1981).
Khazi, et al., *J. Hetereocyclic Chem.*, 4: 243–248 (1995).
Xia, et al., *Bioorg. Med. Chem. Lett.*, 6(7): 919–922 (1996).

* cited by examiner

*Primary Examiner*—Robert Gerstl
(74) *Attorney, Agent, or Firm*—John P. White; Cooper & Dunham LLP

(57) ABSTRACT

This invention is directed to tricyclic compounds which are selective antagonists for NPY (Y5) receptors. The invention provides a pharmaceutical composition comprising a therapeutically effective amount of the compound of the invention and a pharmaceutically acceptable carrier. This invention provides a pharmaceutical composition made by combining a therapeutically effective amount of the compound of this invention and a pharmaceutically acceptable carrier. This invention further provides a process for making a pharmaceutical composition comprising combining a therapeutically effective amount of the compound of the invention and a pharmaceutically acceptable carrier.

23 Claims, No Drawings

SELECTIVE NPY (Y5) ANTAGONISTS (TRICYCLICS)

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

The peptide neurotransmitter neuropeptide Y (NPY) is a 36 amino acid member of the pancreatic polypeptide family with widespread distribution throughout the mammalian nervous system (Dumont et al., 1992). The family includes the pancreatic polypeptide (PP), synthesized primarily by endocrine cells in the pancreas; peptide YY (PYY), synthesized primarily by endocrine cells in the gut; and NPY, synthesized primarily in neurons (Michel, 1991; Dumont et al., 1992; Wahlestedt and Reis, 1993). All pancreatic polypeptide family members share a compact structure involving a "PP-fold" and a conserved C-terminal hexapeptide ending in $Tyr^{36}$ (or $Y^{36}$ in the single letter code). The striking conservation of $Y^{36}$ has prompted the reference to the pancreatic polypeptides' receptors as "Y-type" receptors (Wahlestedt et al., 1987), all of which are proposed to function as seven transmembrane-spanning G protein-coupled receptors (Dumont et al., 1992). NPY and its relatives elicit a broad range of physiological effects through activation of at least five G protein-coupled receptor subtypes known as Y1, Y2, Y3, Y4 (or PP), and the "atypical Y1". While the Y1, Y2, Y3, and Y4 (or PP) receptors were each described previously in both radioligand binding and functional assays, the "atypical Y1" receptor is unique in that its classification is based solely on feeding behavior induced by various peptides including NPY.

The role of NPY in normal and abnormal eating behavior, and the ability to interfere with NPY-dependent pathways as a means to appetite and weight control, are areas of great interest in pharmacological and pharmaceutical research (Sahu and Kalra, 1993; Dryden et al., 1994). NPY is considered to be the most powerful stimulant of feeding behavior yet described (Clark et al., 1984; Levine and Morley, 1984; Stanley and Leibowitz, 1984). The stimulation of feeding behavior by NPY is thought to occur primarily through activation of the hypothalamic "atypical Y1" receptor. For example, direct injection of NPY into the hypothalamus of satiated rats can increase food intake up to 10-fold over a 4-hour period (Stanley et al., 1992). Similar studies using other peptides has resulted in a pharmacologic profile for the "atypical Y1" receptor according to the rank order of potencies of peptides in stimulating feeding behavior as follows: $NPY_{2-36} \geqq NPY \sim PYY \sim [Leu^{31}, Pro^{34}]NPY > NPY_{13-36}$ (Kalra et al., 1991; Stanley et al., 1992). The profile is similar to that of a Y1-like receptor except for the anomalous ability of $NPY_{2-36}$ to stimulate food intake with potency equivalent or better than that of NPY. A subsequent report in *J. Med. Chem.* by Balasubramaniam and co-workers (1994) showed that feeding can be regulated by $[D-Trp^{32}]NPY$. While this peptide was presented as an NPY antagonist, the published data at least in part support a stimulatory effect of $[D-Trp^{32}]NPY$ on feeding. In contrast to other NPY receptor subtypes, the "feeding" receptor has never been characterized for peptide binding affinity in radioligand binding assays.

This problem has been addressed by cloning rat and human cDNAs which encode a single receptor protein, referred to herein as Y5, whose pharmacologic profile links it to the "atypical Y1" receptor. The identification and characterization of a single molecular entity which explains the "atypical Y1" receptor allows the design of selective drugs which modulate feeding behavior (WO 96/16542). It is important to note, though, that any credible means of studying or modifying NPY-dependent feeding behavior must necessarily be highly selective, as NPY interacts with multiple receptor subtypes, as noted above (Dumont et al., 1992).

As used in this invention, the term "antagonist" refers to a compound which binds to, and decreases the activity of, a receptor in the presence of an agonist. In the case of a G-protein coupled receptor, activation may be measured using any appropriate second messenger system which is coupled to the receptor in a cell or tissue in which the receptor is expressed. Some specific but by no means limiting examples of well-known second messenger systems are adenylate cyclase, intracellular calcium mobilization, ion channel activation, guanylate cyclase, and inositol phospholipid hydrolysis. Conversely, the term "agonist" refers to a compound which binds to, and increases the activity of, a receptor as compared with the activity of the receptor in the absence of any agonist.

In order to test compounds for selective binding to the human Y5 receptor the cloned cDNAs encoding both the human and rat Y2 and Y4 (or PP) receptors have been used. The human and rat Y5 receptors are described in coassigned U.S. Pat. No. 5,602,024 and in PCT International Application PCT/US95/15646, published Jun. 6, 1996, as WO 96/16542, the contents of which are hereby incorporated by reference into this application. The human and rat Y2 receptors are described in coassigned U.S. Pat. No. 5,545,549 and in PCT International Application PCT/US95/01469, published Aug. 10, 1995, as WO 95/21245, the contents of which are hereby incorporated by reference into this application. The human and rat Y4 receptors are described in coassigned U.S. Pat. No. 5,516,653 and in PCT International Application PCT/US94/14436, published Jul. 6, 1995, as WO 95/17906, the contents of which are hereby incorporated by reference into this application. The Y1 receptor has been cloned from a variety of species including human, rat and mouse (Larhammar et al., 1992; Herzog et al., 1992; Eva et al., 1990; Eva et al., 1992).

Using the NPY-Y5-selective antagonist CGP 71683A, it was demonstrated recently that food intake in free-feeding and energy-derived lean rats is mediated by the Y5 receptor (Criscione et al., 1998). CGP 71683A has high affinity for the cloned rat NPY-Y5 receptor subtype, but 1,000-fold lower affinity for the cloned rat NPY-Y1, Y2, and Y4 receptors. Examples of additional NPY-Y5-selective compounds are described in WO 97/20823, WO 98/35957, and WO 98/35944.

In one embodiment of this invention the synthesis of novel tricyclic compounds which bind selectively to the cloned human Y5 receptor, compared to the other cloned human NPY receptors, and inhibit the activation of the cloned human Y5 receptor as measured in in vitro assays is disclosed. The in vitro receptor binding and activation assays described hereinafter were performed using various cultured cell lines, each transfected with and expressing only a single Y-type receptor.

In addition, the compounds of the present invention may also be used to treat abnormal conditions such as feeding disorders (obesity and bulimia nervosa), sexual/reproductive disorders, depression, epileptic seizure, hypertension, cerebral hemorrhage, congestive heart failure, sleep disturbances, or any condition in which antagonism of a Y5 receptor may be beneficial.

SUMMARY OF THE INVENTION

This invention provides a compound having the structure:

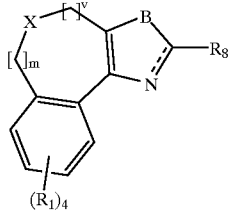

wherein each $R_1$ is independently H, F, Cl, Br, —CN, —OH, —NO$_2$, —NR$_5$R$_6$, —SO$_2$R$_5$, —(CH$_2$)$_n$OR$_5$, —(CH$_2$)$_n$CONR$_5$R$_6$, —(CH$_2$)$_n$NR$_5$COR$_5$, perfluoroalkyl, polyfluoroalkyl, aminoalkyl, or straight chained or branched $C_1$–$C_7$ alkyl;

wherein $R_5$ is independently H; or straight chained or branched $C_1$–$C_7$ alkyl;

wherein $R_6$ is independently H; or straight chained or branched $C_1$–$C_7$ alkyl;

wherein B is O, NH or S;

wherein X is CHR$_5$, O or NR$_5$;

wherein each n independently is an integer from 0 to 6 inclusive;

wherein $R_8$ is

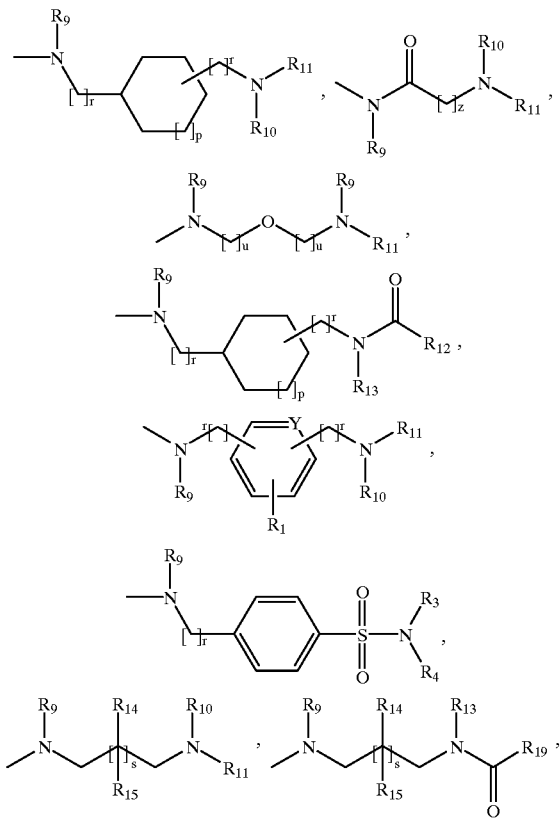

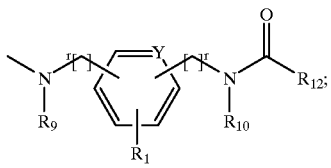

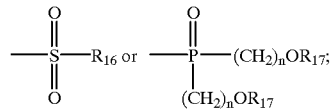

wherein Y is C or N;

wherein $R_7$ is independently straight chained or branched $C_1$–$C_7$ alkyl;

wherein $R_9$ is independently H; or straight chained or branched $C_1$–$C_4$ alkyl;

wherein $R_{10}$ is independently H; or straight chained or branched $C_1$–$C_4$ alkyl;

wherein $R_{11}$ is $$\underset{\underset{O}{\|}}{\overset{\overset{O}{\|}}{-S-}}R_{16} \text{ or } -\overset{(CH_2)_nOR_{17}}{\underset{(CH_2)_nOR_{17}}{\overset{O}{\overset{\|}{P}}}}-(CH_2)_nOR_{17};$$

wherein $R_{12}$ is H, straight chained or branched $C_1$–$C_7$ alkyl, $(CH_2)_nOR_{17}$, or $O(CH_2)_uOR_{17}$; provided that when X is O, $R_{12}$ cannot be methyl;

wherein $R_{13}$ is independently H; —(CH$_2$)$_u$OR$_5$; —(CH$_2$)$_t$CONR$_5$R$_6$; —(CH$_2$)$_u$NR$_5$COR$_5$; —(CH$_2$)$_t$COR$_7$; —(CH$_2$)$_t$CO$_2$R$_5$; —(CH$_2$)$_u$NR$_5$R$_6$; —(CH$_2$)$_u$CN; straight chained or branched $C_1$–$C_7$ alkyl; $C_1$–C7 alkyl in which the $C_2$–$C_7$ atoms may be optionally substituted with one or more F or Cl; $C_3$–$C_7$ cycloalkyl-$C_1$–$C_7$ alkyl; straight chained or branched $C_2$–$C_7$ alkenyl or alkynyl; or $C_3$–$C_7$ cycloalkyl; phenyl or $C_1$–$C_6$ phenylalkyl; wherein the phenyl or $C_1$–$C_6$ phenylalkyl may be substituted with one or more of F, Cl, —CN, —NO$_2$, —NR$_5$R$_6$, —SO$_2$R$_5$, —(CH$_2$)$_n$COR$_7$, —(CH$_2$)$_n$ OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched $C_1$–$C_7$ alkyl, perfluoroalkyl, polyfluoroalkyl, or aminoalkyl;

or $R_{12}$ and $R_{13}$ together with the amide linkage to which they are attached are pyrrolidinonyl, piperidonyl, or oxazolidinonyl; provided that when X is O, $R_{12}$ and $R_{13}$ cannot be oxazolidinonyl;

wherein $R_{14}$ is H; straight chained or branched $C_1$–$C_4$ alkyl; F; or —(CH$_2$)$_r$OR$_5$;

wherein $R_{15}$ is H, straight chained or branched $C_1$–$C_4$ alkyl, or F;

with the proviso that when $R_{14}$ is —OH, $R_{15}$ cannot be F;

wherein $R_{16}$ is NR$_3$R$_4$, perfluoroalkyl, unsubstituted straight chained or branched $C_1$–$C_7$ alkyl, substituted straight chained or branched $C_2$–$C_7$ alkyl, wherein the $C_2$–$C_7$ alkyl may be substituted with one or more of F, Cl, —CN, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$ NR$_5$COR$_5$, —(CH$_2$)$_n$CO$_2$R$_5$, —(CH$_2$)$_n$OCF$_3$, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl; $C_3$–$C_7$ cycloalkyl or cycloalkenyl; phenyl, heteroaryl, or $C_1$–$C_7$ phenylalkyl, wherein the phenyl, heteroaryl, or $C_1$–$C_7$ phenylalkyl may be substituted with one or more of F, Cl, Br, —CN, —$NO_2$, —$NR_5R_6$, —$(CH_2)_nNR_5COR_5$, —$SO_2R_5$, —$(CH_2)_nCOR_7$, —$(CH_2)_nOR_5$, —$(CH_2)_nCONR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl; quinolinyl, 1-naphthyl, 2-naphthyl, or 2,1,3-benzothiadiazolyl; wherein the quinolinyl, 1-naphthyl, 2-naphthyl or 2,1,3-benzothiadiazolyl may be substituted with one or more of F, Cl, Br, —CN, —$NO_2$, —$NR_5R_6$, —$(CH_2)_nNR_5COR_5$, —$SO_2R_5$, —$(CH_2)_nCOR_7$, $(CH_2)_nOR_5$, —$(CH_2)_nCONR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, perfluoroalkyl, polyfluoroalkyl, or aminoalkyl;

with the proviso that when X is O and $R_8$ is $NR_9(CH_2)_uO(CH_2)_uNR_{10}R_{11}$, $R_{16}$ cannot be methyl;

wherein $R_3$ is independently H; —$(CH_2)_uOR_5$; —$(CH_2)_tCONR_5R_6$; —$(CH_2)_uNR_5COR_5$; —$(CH_2)_tCOR_7$; —$(CH_2)_tCO_2R_5$; —$(CH_2)_uNR_5R_6$; —$(CH_2)_uCN$; straight chained or branched $C_1$–$C_7$ alkyl; straight chained or branched $C_2$–$C_7$ alkenyl or alkynyl; or $C_3$–$C_7$ cycloalkyl or cycloalkenyl; phenyl, $C_1$–$C_6$ phenylalkyl, or $C_1$–$C_6$ heteroarylalkyl; wherein the phenyl, $C_1$–$C_6$ phenylalkyl or $C_1$–$C_6$ heteroarylalkyl may be substituted with one or more of F, Cl, Br, —CN, —$NO_2$, —$NR_5R_6$, —$SO_2R_5$, —$(CH_2)_nCOR_7$, —$(CH_2)_n$ $OR_5$, —$(CH_2)_nCONR_5R_6$, —$(CH_2)_nNR_5COR_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

wherein $R_4$ is independently H; —$(CH_2)_uOR_5$; —$(CH_2)_tCONR_5R_6$; —$(CH_2)_uNR_5COR_5$; —$(CH_2)_tCOR_7$; —$(CH_2)_tCO_2R_5$; —$(CH_2)_uNR_5R_6$; —$(CH_2)_uCN$; straight chained or branched $C_1$–$C_7$ alkyl; straight chained or branched $C_2$–$C_7$ alkenyl or alkynyl; or $C_3$–$C_7$ cycloalkyl or cycloalkenyl; phenyl or $C_1$–$C_6$ phenylalkyl; wherein the phenyl or $C_1$–$C_6$ phenylalkyl may be substituted with one or more of F, Cl, Br, —CN, —$NO_2$, —$NR_5R_6$, —$SO_2R_5$, —$(CH_2)_nCOR_7$, —$(CH_2)_n$ $OR_5$, —$(CH_2)_nCONR_5R_6$, —$(CH_2)_nNR_5COR_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

or $R_3$ and $R_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —$(CH_2)_nNR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, straight chained or branched $C_1$–$C_7$ alkyl, perfluoroalkyl, polyfluoroalkyl, or aminoalkyl, straight chained or branched $C_2$–$C_7$ alkenyl or alkynyl, Or $C_3$–$C_7$ cycloalkyl or cycloalkenyl, or phenyl or heteroaryl; wherein if —$(CH_2)_nNR_5R_6$, —$(CH_2)_nOR_5$, or —$(CH_2)_nNR_5COR_5$ are in the 2-position, then n is not 0; wherein the phenyl or heteroaryl may be substituted with one or more of F, Cl, Br, —CN, —$NO_2$, —$NR_5R_6$, —$SO_2R_5$, —$(CH_2)_nCOR_7$, —$(CH_2)_nOR_5$, —$(CH_2)_n$ $CONR_5R_6$, —$(CH_2)_nNR_5COR_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

or $R_3$ and $R_4$ taken together with the nitrogen atom to which they are attached are morpholinyl, thiomorpholinyl, [1,4]oxazepanyl, [1,4]thiazepanyl, piperazinyl, or [1,4]diazepanyl, wherein the morpholinyl, thiomorpholinyl, [1,4]oxazepanyl, [1,4]thiazepanyl, piperazinyl, or [1,4]diazepanyl is optionally substituted with straight chained or branched $C_1$–$C_5$ alkyl or $(CH_2)_tOR_5$; and wherein the nitrogen atom of the piperazinyl or [1,4]diazepanyl ring may be optionally substituted with —$(CH_2)_uOR_5$; —$COR_5$; straight chained or branched $C_1$–$C_5$ alkyl; or phenyl; wherein the phenyl may be substituted with one or more of F, Cl, Br, —CN, —$NO_2$, —$NR_5R_6$ —$(CH_2)_nOR_5$, straight chained or branched $C_1$–$C_3$ alkyl, perfluoroalkyl, polyfluoroalkyl, or aminoalkyl;

wherein $R_{17}$ is H, straight chained or branched $C_1$–$C_4$ alkyl, perfluoroalkyl, or polyfluoroalkyl;

wherein $R_{19}$ is $(CH_2)_nOR_5$, $NR_5R_6$, phenyl, or heteroaryl, wherein the phenyl or heteroaryl may be substituted with one or more of F, Cl, Br, —CN, —$NO_2$, —$NR_5R_6$, —$(CH_2)_nNR_5COR_5$, —$SO_2R_5$, —$(CH_2)_nCOR_7$, —$(CH_2)_nOR_5$, —$(CH_2)_nCONR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

wherein m is 0 or 1;

wherein each p independently is an integer from 0 to 2 inclusive;

wherein each r independently is an integer from 0 to 3 inclusive;

wherein each s independently is an integer from 1 to 6 inclusive;

wherein t is an integer from 1 to 4 inclusive;

wherein each u independently is an integer from 2 to 4 inclusive;

wherein v is 1 or 2;

with the proviso that when v is 2, m is 0;

wherein z is an integer from 2 to 7;

or a pharmaceutically acceptable salt thereof.

The invention also provides a pharmaceutical composition comprising a therapeutically effective amount of the compound of the invention and a pharmaceutically acceptable carrier. This invention further provides a pharmaceutical composition made by combining a therapeutically effective amount of the compound of this invention and a pharmaceutically acceptable carrier. This invention further provides a process for making a pharmaceutical composition comprising combining a therapeutically effective amount of the compound of the invention and a pharmaceutically acceptable carrier.

DETAILED DESCRIPTION OF THE INVENTION

This invention provides a compound having the structure:

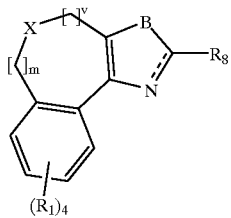

wherein each $R_1$ is independently H, F, Cl, Br, —CN, —OH, —NO$_2$, —NR$_5$R$_6$, —SO$_2$R$_5$, —(CH$_2$)$_n$OR$_5$, —(CH$_2$)$_n$CONR$_5$R$_6$, —(CH$_2$)$_n$NR$_5$COR$_5$, perfluoroalkyl, polyfluoroalkyl, aminoalkyl, or straight chained or branched $C_1$–$C_7$ alkyl;

wherein $R_5$ is independently H; or straight chained or branched $C_1$–$C_7$ alkyl;

wherein $R_6$ is independently H; or straight chained or branched $C_1$–$C_7$ alkyl;

wherein B is O, NH or S;

wherein X is CHR$_5$, O or NR$_5$;

wherein each n independently is an integer from 0 to 6 inclusive;

wherein $R_8$ is

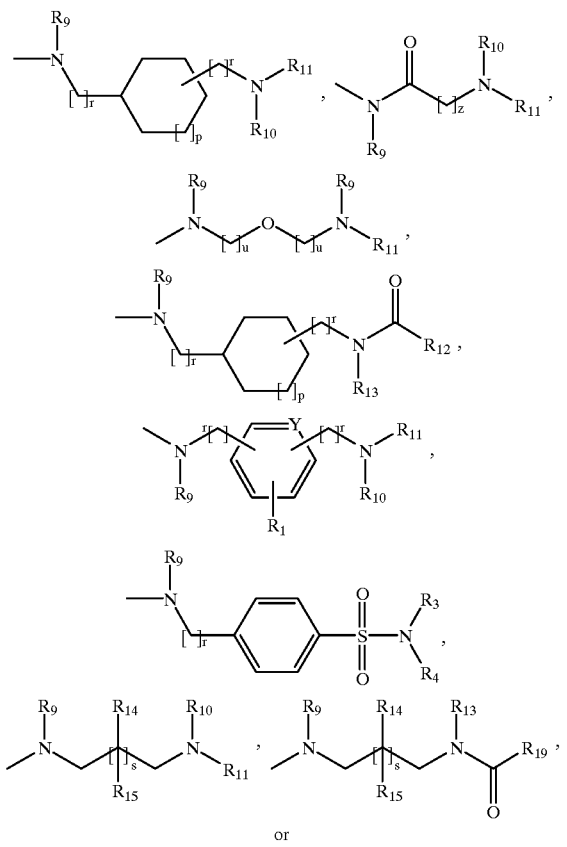

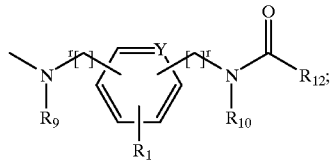

wherein Y is C or N;

wherein $R_7$ is independently straight chained or branched $C_1$–$C_7$ alkyl;

wherein $R_9$ is independently H; or straight chained or branched $C_1$–$C_4$ alkyl;

wherein $R_{10}$ is independently H; or straight chained or branched $C_1$–$C_4$ alkyl;

wherein $R_{11}$ is

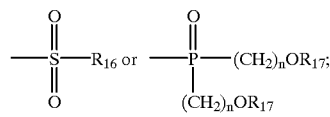

wherein $R_{12}$ is H, straight chained or branched $C_1$–$C_7$ alkyl, (CH$_2$)$_n$OR$_{17}$, or O(CH$_2$)$_u$OR$_{17}$; provided that when X is O, $R_{12}$ cannot be methyl;

wherein $R_{13}$ is independently H; —(CH$_2$)$_u$OR$_5$; —(CH$_2$)$_t$CONR$_5$R$_6$; —(CH$_2$)$_u$NR$_5$COR$_5$; —(CH$_2$)$_t$COR$_7$; —(CH$_2$)$_t$CO$_2$R$_5$; —(CH$_2$)$_u$NR$_5$R$_6$; —(CH$_2$)$_u$CN; straight chained or branched $C_1$–$C_7$ alkyl; $C_1$–$C_7$ alkyl in which the $C_2$–$C_7$ atoms may be optionally substituted with one or more F or Cl; $C_3$–$C_7$ cycloalkyl-$C_1$–$C_7$ alkyl; straight chained or branched $C_2$–$C_7$ alkenyl or alkynyl; or $C_3$–$C_7$ cycloalkyl; phenyl or $C_1$–$C_6$ phenylalkyl; wherein the phenyl or $C_1$–$C_6$ phenylalkyl may be substituted with one or more of F, Cl, —CN, —NO$_2$, —NR$_5$R$_6$, —SO$_2$R$_5$, —(CH$_2$)$_n$COR$_7$, —(CH$_2$)$_n$ OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched $C_1$–$C_7$ alkyl, perfluoroalkyl, polyfluoroalkyl, or aminoalkyl;

or $R_{12}$ and $R_{13}$ together with the amide linkage to which they are attached are pyrrolidinonyl, piperidonyl, or oxazolidinonyl; provided that when X is O, $R_{12}$ and $R_{13}$ cannot be oxazolidinonyl;

wherein $R_{14}$ is H; straight chained or branched $C_1$–$C_4$ alkyl; F; or —(CH$_2$)$_r$OR$_5$;

wherein $R_{15}$ is H, straight chained or branched $C_1$–$C_4$ alkyl, or F;

with the proviso that when $R_{14}$ is —OH, $R_{15}$ cannot be F;

wherein $R_{16}$ is NR$_3$R$_4$, perfluoroalkyl, unsubstituted straight chained or branched $C_1$–$C_7$ alkyl, substituted straight chained or branched $C_2$–$C_7$ alkyl, wherein the $C_2$–$C_7$ alkyl may be substituted with one or more of F, Cl, —CN, —NR$_5$R$_6$, —SO$_2$R$_5$, (CH$_2$)$_n$COR$_7$, —(CH$_2$)$_n$ OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$OCF$_3$, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl; $C_3$–$C_7$ cycloalkyl or cycloalkenyl; phenyl, heteroaryl, or $C_1$–$C_7$ phenylalkyl, wherein the phenyl, heteroaryl, or $C_1$–$C_7$ phenylalkyl may be substituted with one or more of F, Cl, Br, —CN, —NO$_2$, —NR$_5$R$_6$, —(CH$_2$)$_n$NR$_5$COR$_5$, —$SO_2R_5$, —$(CH_2)_nCOR_7$, —$(CH_2)_nOR_5$, —$(CH_2)_n$
$CONR_5R_6$, —$(CH_2)_nCO_2R_5$, —$(CH_2)_nSO_2NR_5R_6$,
ethylenedioxy, methylenedioxy, straight chained or
branched $C_1$–$C_7$ alkyl, perfluoroalkyl, polyfluoroalkyl,
or aminoalkyl, straight chained or branched $C_2$–$C_7$
alkenyl or alkynyl, or $C_3$–$C_7$ cycloalkyl or cycloalk-
enyl; quinolinyl, 1-naphthyl, 2-naphthyl, or 2,1,3-
benzothiadiazolyl; wherein the quinolinyl, 1-naphthyl,
2-naphthyl or 2,1,3-benzothiadiazolyl may be substi-
tuted with one or more of F, Cl, Br, —CN, —$NO_2$,
—$NR_5R_6$, —$(CH_2)_nNR_5COR_5$, —$SO_2R_5$, —$(CH_2)_n$
$COR_7$, —$(CH_2)_nOR_5$, —$(CH_2)_nCONR_5R_6$, —$(CH_2)_n$
$CO_2R_5$, —$(CH_2)_nSO_2NR_5R_6$, ethylenedioxy,
methylenedioxy, straight chained or branched $C_1$–$C_7$
alkyl, perfluoroalkyl, polyfluoroalkyl, or aminoalkyl;
with the proviso that when X is O and $R_8$ is $NR_9(CH_2)_u$
$O(CH_2)_uNR_{10}R_{11}$, $R_{16}$ cannot be methyl;
wherein $R_3$ is independently H; —$(CH_2)_uOR_5$; —$(CH_2)_t$
$CONR_5R_6$; —$(CH_2)_uNR_5COR_5$; —$(CH_2)_tCOR_7$;
—$(CH_2)_tCO_2R_5$; —$(CH_2)_uNR_5R_6$; —$(CH_2)_uCN$;
straight chained or branched $C_1$–$C_7$ alkyl; straight
chained or branched $C_2$–$C_7$ alkenyl or alkynyl; or
$C_3$–$C_7$ cycloalkyl or cycloalkenyl; phenyl, $C_1$–$C_6$
phenylalkyl, or $C_1$–$C_6$ heteroarylalkyl; wherein the
phenyl, $C_1$–$C_6$ phenylalkyl or $C_1$–$C_6$ heteroarylalkyl
may be substituted with one or more of F, Cl, Br, —CN,
—$NO_2$, —$NR_5R_6$, —$SO_2R_5$, —$(CH_2)_nCOR_7$,
—$(CH_2)_n$ $OR_5$, —$(CH_2)_nCONR_5R_6$, —$(CH_2)_n$
$NR_5COR_5$, —$(CH_2)_nCO_2R_5$, —$(CH_2)_nSO_2NR_5R_6$,
straight chained or branched $C_1$–$C_7$ alkyl,
perfluoroalkyl, polyfluoroalkyl, or aminoalkyl, straight
chained or branched $C_2$–$C_7$ alkenyl or alkynyl, or
$C_3$–$C_7$ cycloalkyl or cycloalkenyl;
wherein $R_4$ is independently H; —$(CH_2)_uOR_5$; —$(CH_2)_t$
$CONR_5R_6$; —$(CH_2)_uNR_5COR_5$; —$(CH_2)_tCOR_7$;
—$(CH_2)_tCO_2R_5$; —$(CH_2)_uNR_5R_6$; —$(CH_2)_uCN$;
straight chained or branched $C_1$–$C_7$ alkyl; straight
chained or branched $C_2$–$C_7$ alkenyl or alkynyl; or
$C_3$–$C_7$ cycloalkyl or cycloalkenyl; phenyl or $C_1$–$C_6$
phenylalkyl; wherein the phenyl or $C_1$–$C_6$ phenylalkyl
may be substituted with one or more of F, Cl, Br, —CN,
—$NO_2$, —$NR_5R_6$, —$SO_2R_5$, —$(CH_2)_nCOR_7$,
—$(CH_2)_n$ $OR_5$, —$(CH_2)_nCONR_5R_6$, —$(CH_2)_n$
$NR_5COR_5$, —$(CH_2)_nCO_2R_5$, —$(CH_2)_nSO_2NR_5R_6$,
straight chained or branched $C_1$–$C_7$ alkyl,
perfluoroalkyl, polyfluoroalkyl, or aminoalkyl, straight
chained or branched $C_2$–$C_7$ alkenyl or alkynyl, or
$C_3$–$C_7$ cycloalkyl or cycloalkenyl;
or $R_3$ and $R_4$ taken together with the nitrogen atom to
which they are attached are 1-azetidinyl,
1-pyrrolidinyl, 1-piperidinyl, or 1H-azepanyl, wherein
the 1-azetidinyl, 1-pyrrolidinyl, 1-piperidinyl, or
1H-azepanyl is substituted with one or more of F,
—CN, —$(CH_2)_nNR_5R_6$, —$SO_2R_5$, —$(CH_2)_nCOR_7$,
—$(CH_2)_nOR_5$, —$(CH_2)_nCONR_5R_6$, —$(CH_2)_n$
$NR_5COR_5$, —$(CH_2)_nCO_2R_5$, straight chained or
branched $C_1$–$C_7$ alkyl, perfluoroalkyl, polyfluoroalkyl,
or aminoalkyl, straight chained or branched $C_2$–$C_7$
alkenyl or alkynyl, or $C_3$–$C_7$ cycloalkyl or
cycloalkenyl, or phenyl or heteroaryl; wherein if
—$(CH_2)_nNR_5R_6$, —$(CH_2)_nOR_5$, or —$(CH_2)_n$
$NR_5COR_5$ are in the 2-position, then n is not 0; wherein
the phenyl or heteroaryl may be substituted with one or
more of F, Cl, Br, —CN, —$NO_2$, —$NR_5R_6$, —$SO_2R_5$,
—$(CH_2)_nCOR_7$, —$(CH_2)_nOR_5$, —$(CH_2)_n$ $CONR_5R_6$,
—$(CH_2)_nNR_5COR_5$, —$(CH_2)_nCO_2R_5$, —$(CH_2)_n$
$SO_2NR_5R_6$, straight chained or branched $C_1$–$C_7$ alkyl,
perfluoroalkyl, polyfluoroalkyl, or aminoalkyl, straight
chained or branched $C_2$–$C_7$ alkenyl or alkynyl, or
$C_3$–$C_7$ cycloalkyl or cycloalkenyl;
or $R_3$ and $R_4$ taken together with the nitrogen atom to
which they are attached are morpholinyl,
thiomorpholinyl, [1,4]oxazepanyl, [1,4]thiazepanyl,
piperazinyl, or [1,4]diazepanyl, wherein the
morpholinyl, thiomorpholinyl, [1,4]oxazepanyl, [1,4]
thiazepanyl, piperazinyl, or [1,4]diazepanyl is option-
ally substituted with straight chained or branched
$C_1$–$C_5$ alkyl or $(CH_2)_rOR_5$; and wherein the nitrogen
atom of the piperazinyl or [1,4]diazepanyl ring may be
optionally substituted with —$(CH_2)_uOR_5$; —$COR_5$;
straight chained or branched $C_1$–$C_5$ alkyl; or phenyl;
wherein the phenyl may be substituted with one or
more of F, Cl, Br, —CN, —$NO_2$, —$NR_5R_6$ —$(CH_2)_n$
$OR_5$, straight chained or branched $C_1$–$C_3$ alkyl,
perfluoroalkyl, polyfluoroalkyl, or aminoalkyl;
wherein $R_{17}$ is H, straight chained or branched $C_1$–$C_4$
alkyl, perfluoroalkyl, or polyfluoroalkyl;
wherein $R_{19}$ is $(CH_2)_nOR_5$, $NR_5R_6$, phenyl, or heteroaryl,
wherein the phenyl or heteroaryl may be substituted
with one or more of F, Cl, Br, —CN, —$NO_2$, —$NR_5R_6$,
—$(CH_2)_nNR_5COR_5$, —$SO_2R_5$, —$(CH_2)_nCOR_7$,
—$(CH_2)_nOR_5$, —$(CH_2)_nCONR_5R_6$, —$(CH_2)_nCO_2R_5$,
—$(CH_2)_nSO_2NR_5R_6$, ethylenedioxy, methylenedioxy,
straight chained or branched $C_1$–$C_7$ alkyl,
perfluoroalkyl, polyfluoroalkyl, or aminoalkyl, straight
chained or branched $C_2$–$C_7$ alkenyl or alkynyl, or
$C_3$–$C_7$ cycloalkyl or cycloalkenyl;
wherein m is 0 or 1;
wherein each p independently is an integer from 0 to 2
inclusive;
wherein each r independently is an integer from 0 to 3
inclusive;
wherein each s independently is an integer from 1 to 6
inclusive;
wherein t is an integer from 1 to 4 inclusive;
wherein each u independently is an integer from 2 to 4
inclusive;
wherein v is 1 or 2;
with the proviso that when v is 2, m is 0;
wherein z is an integer from 2 to 7;
or a pharmaceutically acceptable salt thereof.

In one embodiment, the compound comprises the (+) enantiomer. In another embodiment, the compound comprises the (−) enantiomer.

In one embodiment, the compound has the structure:

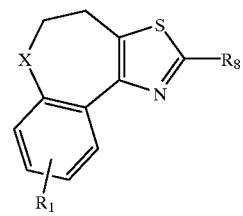

wherein X is $CR_5R_6$, O or $NR_5$.

In another embodiment, the compound has the structure:

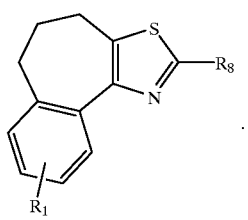

In still another embodiment, the compound has the structure:

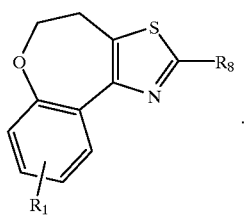

In a further embodiment, the compound has the structure:

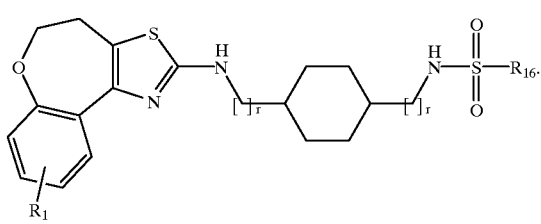

In still further embodiments, the compound has the structure selected from the group consisting of:

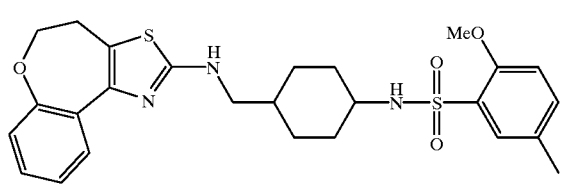

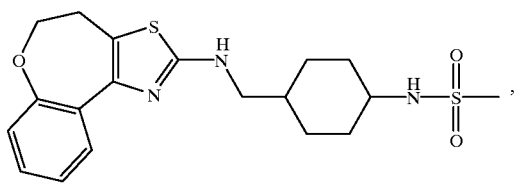

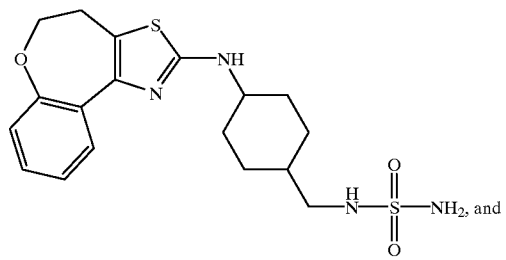

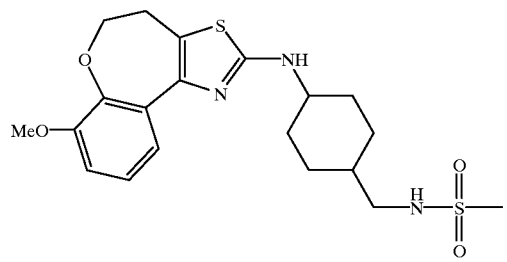

In another embodiment, the compound has the structure:

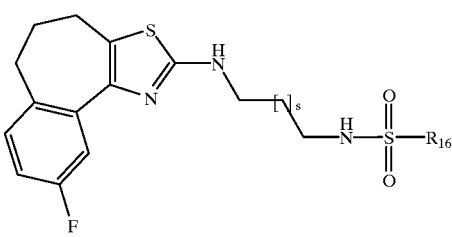

wherein s is 2, 3 or 4.

In still other embodiments, the compound has the structure selected from the group consisting of:

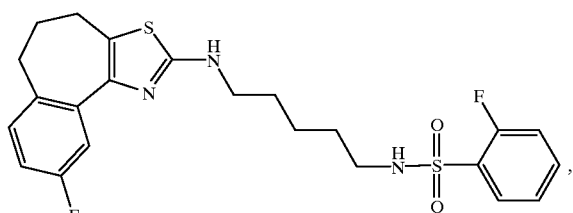

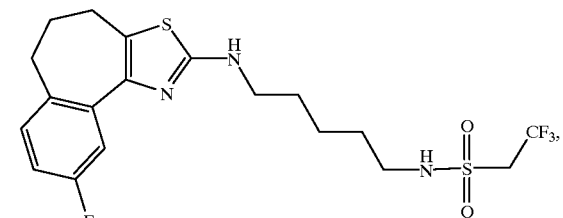

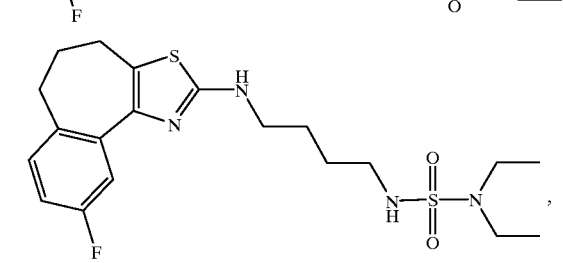

-continued
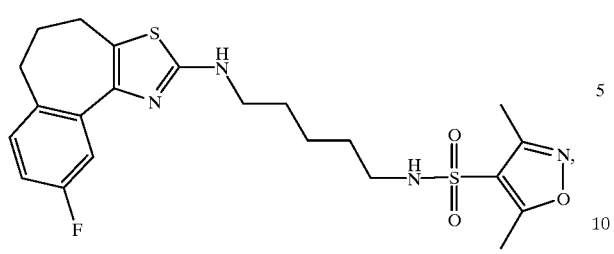
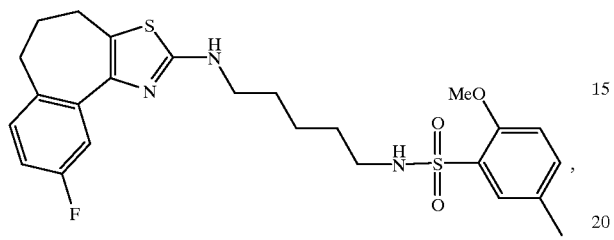
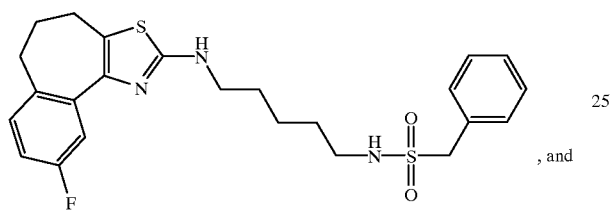
, and
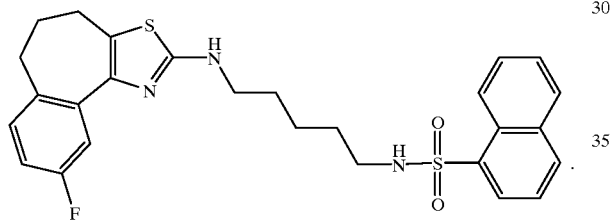
In a further embodiment, the compound has the structure:
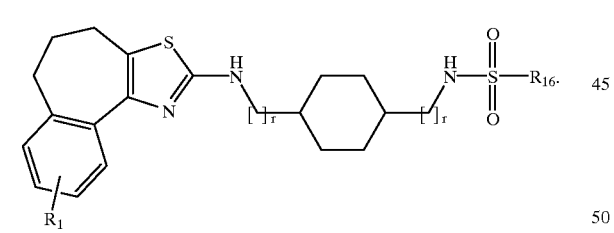
In still further embodiments, the compound has the structure selected from the group consisting of:
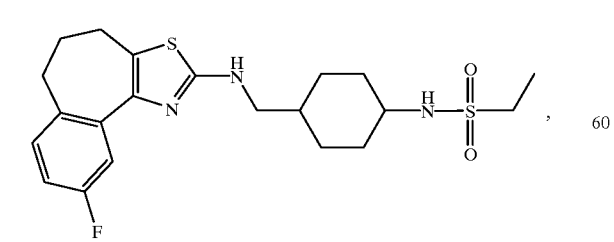
-continued
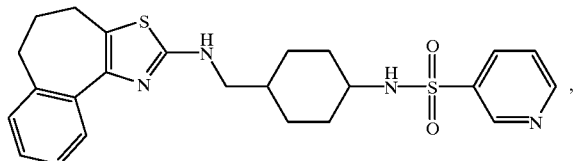
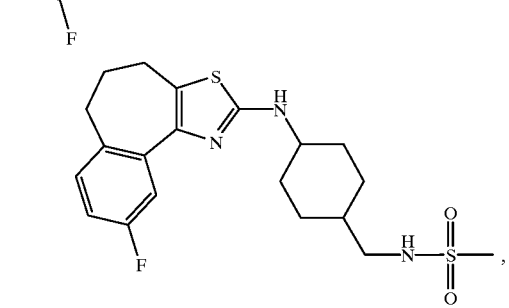
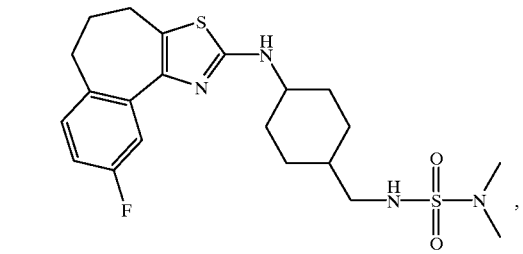
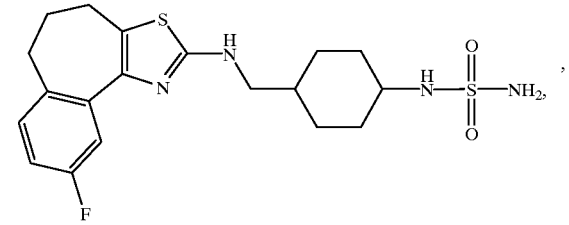
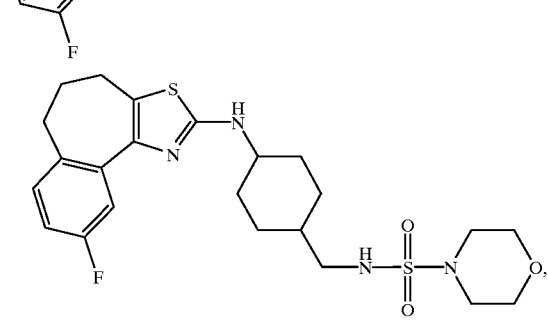
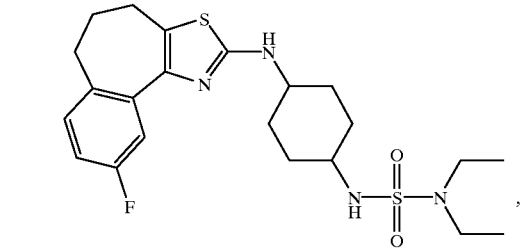

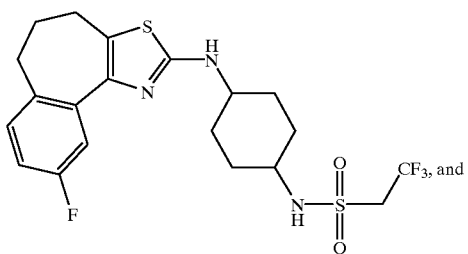

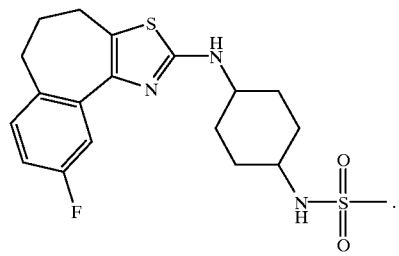

In still other embodiments, the compound has the structure:

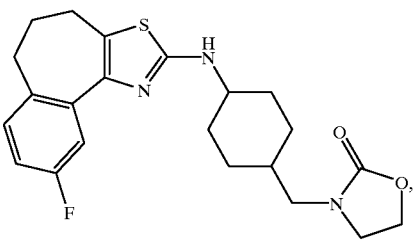

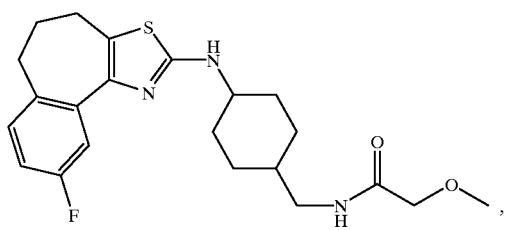

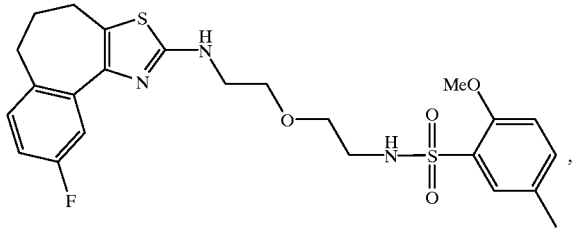

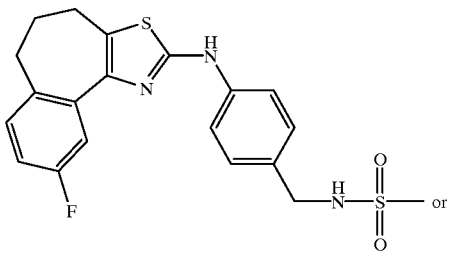

In still further embodiments, the compound has the structure selected from the group consisting of:

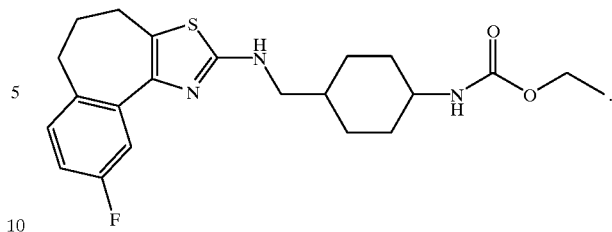

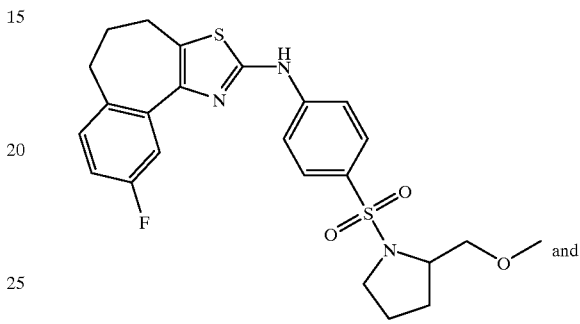

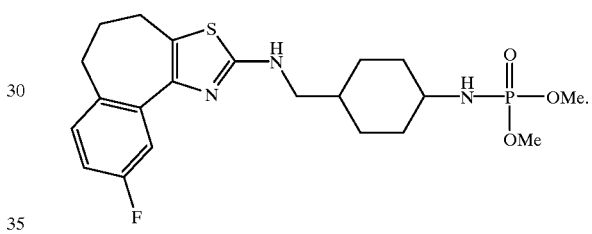

In the present invention, the term "heteroaryl" is used to include five and six membered unsaturated rings that may contain one or more heteroatoms such as oxygen, sulfur, and nitrogen. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, benzthiazolyl, purinyl, imidazo[2,1-b]thiazolyl, quinolinyl, isoquinolinyl, quinolizinyl, and 2,1,3-benzothiazolyl.

Furthermore, any of the heteroaryl groups recited above may be substituted with thienyl, isoxazolyl, or pyridyl.

Included in this invention are pharmaceutically acceptable salts and complexes of all of the compounds described herein. The salts include but are not limited to the acids and bases listed herein. The salts include, but are not limited to the following inorganic acids: hydrochloric acid, hydrobromic acid, hydroiodic acid, sulfuric acid and boric acid. The salts include, but are not limited to the following organic acids: acetic acid, malonic acid, succinic acid, fumaric acid, tartaric acid, maleic acid, citric acid, methanesulfonic acid, benzoic acid, glycolic acid, lactic acid and mandelic acid. The salts include, but are not limited to the inorganic base, ammonia. The salts include, but are not limited to the following organic bases: methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

The present invention includes within its scope prodrugs of the compounds of the invention. In general, such prodrugs will be functional derivatives of the compounds of the invention which are readily convertible in vivo into the required compound.

Thus, in the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

This invention further provides a pharmaceutical composition comprising a therapeutically effective amount of the compound of the invention and a pharmaceutically acceptable carrier. In one embodiment, the amount of the compound is an amount from about 0.01 mg to about 800 mg. In another embodiment, the amount of the compound is an amount from about 0.01 mg to about 500 mg. In another embodiment, the amount of the compound is an amount from about 0.01 mg to about 250 mg. In another embodiment, the amount of the compound is an amount from about 0.1 mg to about 60 mg. In another embodiment, the amount of the compound is an amount from about 1 mg to about 20 mg. In a further embodiment, the carrier is a liquid and the composition is a solution. In another embodiment, the carrier is a solid and the composition is a tablet. In a further embodiment, the carrier is a gel and the composition is a suppository.

This invention provides a pharmaceutical composition made by combining a therapeutically effective amount of the compound of this invention and a pharmaceutically acceptable carrier.

This invention provides a process for making a pharmaceutical composition comprising combining a therapeutically effective amount of the compound of this invention and a pharmaceutically acceptable carrier.

In the subject invention a "therapeutically effective amount" is any amount of a compound which, when administered to a subject suffering from a disease against which the compounds are effective, causes reduction, remission, or regression of the disease.

In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be readily determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

One skilled in the art will readily appreciate that appropriate biological assays will be used to determine the therapeutic potential of the claimed compounds for treating the above noted disorders.

This invention further provides compositions which need not be pharmaceutical as that term is understood in the art. Such compositions comprise a compound in accordance with the subject invention in an amount effective to agonize and/or antagonize a Y5 receptor and a suitable carrier.

Still further, the invention provides a method of agonizing and/or antagonizing a Y5 receptor which comprises contacting the receptor, e.g. in vitro or in vivo, with an amount of a compound of this invention effective to agonize and/or antagonize the receptor.

This invention will be better understood from the Experimental Details which follow. However, one skilled in the art will readily appreciate that the specific methods and results discussed are merely illustrative of the invention as described more fully in the claims which follow thereafter.

Experimental Details and Results
I. Synthetic Methods for Examples

General Procedures Relating to Examples

For the formation of 2-aminothiazoles from 2-haloketones and thioureas, see, for example, Kearney, P. C., et al., 1998; Di Fabio, R. and Pentassuglia, G., 1998; De Kimpe, N., et al., 1996; Plazzi, P. V., et al., 1995; and Novikova, A. P., 1991.

For the formation of thiazoles from 2-haloketones and thioamides, see, for example, Critcher, D. J. and Pattenden, G., 1996; and Friedman, B. S., et al., 1937.

For the formation of 2-aminoimidazoles from 2-haloketones and guanidines, see, for example, Little, T. L. and Webber, 1994; and Chabaka, L. M., et al., 1994.

For the formation of imidazoles from 2-haloketones and amidines, see, for example, Demchenko, A. M., et al., 1997; and Nagao, Y., et al., 1996.

For the synthesis of 2-aminooxazoles from 2-haloketones and ureas, see, for example, Pathak, V. N., et al., 1993; Crangk, G. and Foulis, M. J., 1971; and Marchetti, E., et al., 1968.

For the formation of oxazoles from 2-haloketones and amides, see, for example, Hammar, W. J. and Rustad, M. A., 1981; and Zhao, Z., et al., 1991.

All reactions were performed under an inert atmosphere (Argon) and the reagents, neat or in appropriate solvents, were transferred to the reaction vessel via syringe and cannula techniques. Anhydrous solvents were purchased from Aldrich Chemical Company and used as received. Examples 1–90 described in this patent application were named using ACD/Name program (version 2.51, Advanced Chemistry Development Inc., Toronto, Ontario, M5H2L3, Canada).

$^1$H and $^{13}$C spectra were recorded at 300 and 75 MHz (QE Plus) with $CDCl_3$ as solvent (unless otherwise noted) and tetramethylsilane as internal standard. s=singlet; d=doublet; t=triplet; q=quartet; p=pentet; sextet; septet; b=broad; m=multiplet. Elemental analyses were performed by Robertson Microlit Laboratories, Inc. Low-resolution electrospray MS spectra were measured (ESMS, MS) and MH$^+$ is reported. Thin-layer chromatography (TLC) was carried out on glass plates precoated with silica gel 60 $F_{254}$ (0.25 mm, EM Separations Tech.). Preparative thin-layer chromatography was carried out on glass sheets precoated with silica gel GF (2 mm, Analtech). Flash column chromatography was performed on Merck silica gel 60 (230–400 mesh). Melting points were determined in open capillary tubes on a Med-Temp apparatus and are uncorrected.

General Procedure for the Synthesis of Bromoketones

To a cooled solution of the ketone (1 equivalent) in acetic acid was slowly added bromine (1 equivalent). The reaction mixture was stirred at room temperature for 3 hours. The solvent was evaporated and the residue dissolved in dichloromethane, washed with saturated sodium bicarbonate and water. The organic phase was dried over sodium sulfate. Evaporation of the combined decolored organic phase afforded a light yellow oil in >80% yield in most cases.

Similarly, the following were prepared:

6-Bromo-3-fluoro-6,7,8,9-tetrahydro-5H-benzo[a]cyclohepten-5-one was obtained as a light yellow oil in 97% yield from 8-fluoro 1-benzosuberone and bromine: $^1$H NMR δ 7.30 (dd, 1H, JJ=2.7, 9.0 Hz), 7.20–7.09 (m, 2H), 4.85 (dd, 1H, JJ=4.2, 7.5 Hz), 3.06–2.97 (m, 1H), 2.91–2.81 (m, 1H), 2.43–2.24 (m, 2H), 2.05–1.97 (m, 2H).

6-Bromo-2-methoxy-6,7,8,9-tetrahydro-5H-benzo[a]cyclohepten-5-one was obtained as a light brown oil in 97% yield from 2-methoxy-6,7,8,9-tetrahydro-5H-benzo[a]cyclohepten-5-one and bromine: $^1$H NMR δ 7.68 (d, 1H, J=8.6 Hz), 6.80 (dd, 1H, J=2.5, 8.6 Hz), 6.70 (d, 1H, J=2.5 Hz), 4.87 (dd, 1H, J=4.3, 7.9 Hz), 3.85 (s, 3H), 3.10–2.99 (m, 1H), 2.94–2.82 (m, 1H), 2.40–2.30 (m, 2H), 2.0 (m, 2H).

2-Methoxy-6,7,8,9-tetrahydro-5H-benzo[a]cyclohepten-5-one: To a homogeneous mixture of phosphorus pentoxide and 85% phosphorus acid at 100° C., was added 5-(3-methoxyphenyl)pentanoic acid in small portions over 20 minutes. The vigorously stirred mixture was heated at 100° C. for 6 hours. Then it was poured on ice-water, and extracted with ether (3 times). The organic phase was washed with water and dried over anhydrous sodium sulfate. Evaporation of the combined organic phase afforded a light yellow oil in more than 95% yield; $^1$H NMR δ 7.77 (d, 1H, J=8.6 Hz), 6.80 (dd, 1H, J=2.5, 8.6 Hz), 6.69 (d, 1H, J=2.5 Hz), 3.84 (s, 3H), 2.90 (t, 2H, J=6.2 Hz), 2.71 (t, 2H, J=5.9 Hz), 1.91–1.76 (m, 4H).

5-(3-Methoxyphenyl)pentanoic acid. A mixture of ethyl 5-(3-methoxyphenyl)pentanoate (1 equivalent) and sodium hydroxide (3 equivalents) in THF/$H_2O$ was heated at reflux overnight. THF was evaporated, the aqueous phase acidified with 6N HCl to pH<5, and then extracted with a mixture of chloroform:isopropyl alcohol (3:1, 5 times). The organic phase was dried over anhydrous sodium sulfate. A light yellow oil was obtained in more than 85% yield after removal of the solvent: $^1$H NMR δ 7.20 (m, 1H), 6.79–6.73 (m, 3H), 3.80 (s, 3H), 2.62 (m, 2H), 2.38 (m, 2H), 1.68 (m, 4H).

Ethyl 5-(3-methoxyphenyl)pentanoate. A reaction mixture comprising ethyl (E) 5-(3-methoxyphenyl) 4-pentenoate and 5% palladium on carbon in methanol was stirred under 300 psi $H_2$ overnight. A light yellow oil was obtained after filtration and evaporation: $^1$H NMR δ 7.20 (m, 1H), 6.78–6.72 (m, 3H), 4.12 (q, 2H, J=7.1 Hz), 3.80 (s, 3H), 2.60 (m, 2H), 2.32 (m, 2H), 1.66 (m, 4H), 1.25 (t, 3H, J=7.1 Hz).

Ethyl (E) 5-(3-methoxyphenyl) 4-pentenoate. To a refluxed solution of 3-iodoanisole (5.0 g, 21.37 mmol, 1 equivalent), tetrakis(triphenylphosphine)palladium(0) ([($C_6H_5$)$_3$P]$_4$Pd, 740 mg, 0.64 mmol, 0.03 equivalent), and triethyl amine (6.0 ml, 42.74 mmol, 2.0 equivalents) in $CH_3CN$/THF, was added 1.0 g of ethyl 4-pentenoate every two hours (total 3.3 g, 25.64 mmol, 1.2 equivalents). After the addition was complete, the reaction mixture was stirred at reflux overnight. Solvent was removed and the dark brown residue dissolved in 5% HCl and extracted with methylene chloride (3 times). The combined organic extracts were washed with saturated sodium bicarbonate. A dark brown oil was obtained after the organic solvent was removed. The crude product was purified by flash column (silica gel, chloroform hexane=1:5) to afford 3.6 g of a light yellow oil in 72% yield: $^1$H NMR δ 7.21 (t, 1H, J=7.9 Hz), 6.93 (m, 1H), 6.87 (m, 1H), 6.76 (dd, 1H, J=2.6, 8.1 Hz), 6.40 (d, 1H, J=18 Hz), 6.25–6.16 (m, 1H), 4.15 (q, 2H, J=7.2 Hz), 3.81 (s, 3H), 2.50 (m, 4H), 1.26 (t, 3H, J=7.2 Hz).

4-Bromo-9-methoxy-3,4-dihydro-1-benzoxepin-5(2H)-one was obtained as a light yellow oil in 100% yield from 9-methoxy-3,4-dihydro-1-benzoxepin-5(2H)-one and bromine: $^1$H NMR δ 7.32 (t, 1H, J=4.8 Hz), 7.06 (d, 2H, J=5.1 Hz), 4.99 (dd, 1H, J=7.0, 8.4 Hz), 4.60–4.53 (m, 1H), 4.20–4.11 (m, 1H), 3.90 (s, 3H), 3.02–2.91 (m, 1H), 2.56–2.45 (m, 1H).

9-Methoxy-3,4-dihydro-1-benzoxepin-5(2H)-one. To PPA in toluene at 100° C., was added 4-(2-methoxyphenoxy)butanoic acid and the mixture stirred overnight. The mixture was poured onto ice-water, and extracted with ether (3 times). The combined organic phase was washed with water and dried over anhydrous sodium sulfate. Evaporation of the organic phase afforded a light yellow oil in 10% yield: $^1$H NMR δ 7.33 (dd, 1H, J=4.4, 5.1 Hz), 7.03 (d, 2H, J=4.3 Hz), 4.31 (t, 2H, J=6.6 Hz), 3.90 (s, 3H), 2.90 (t, 2H, J=6.9 Hz), 2.22 (p, 2H, J=6.8 Hz).

4-(2-Methoxyphenoxy)butanoic acid. To the mixture of guaiacol (2-methoxyphenol, 1.0 equivalent) and γ-butyrolactone, cooled in an ice-water bath, was added potassium ethoxide in small portions. The reaction mixture was heated at 110° C. overnight, and then at 155° C. for an additional 10 hours. The mixture was then poured into ice water, basified to pH 9.5 with saturated sodium bicarbonate, and extracted with chloroform. The aqueous phase was separated, acidified to pH 2.5 with 2N HCl, and extracted with a mixture of chloroform:isopropyl alcohol (3:1). The organic phase was dried over anhydrous sodium sulfate and evaporated to afford 4-(2-methoxyphenoxy)butanoic acid as a light brown oil in 55% yield. The crude product was used for next reaction without further purification: $^1$H NMR δ 6.90 (m, 4H), 4.08 (t, 2H, J=6.2 Hz), 3.85 (s, 3H), 2.62 (t, 2H, J=7.2 Hz), 2.16 (p, 2H, J=6.6 Hz).

3-Bromo-2,3-dihydro-4H-chromen-4-one was obtained as a yellow oil in 100% yield from 4-chromanone and bromine. 1H NMR δ 7.93 (dd, 1H, J=1.5, 7.8 Hz), 7.53 (td, 1H, J=1.8, 7.8 Hz), 7.11–7.04 (m, 2H), 4.64 (m, 3H).

General Procedure for the Synthesis of Thioureas

A protected diamine such as N-Boc-1,4-diaminobutane or N-Boc-1,5-diaminopentane (1 equivalent) was dissolved in tetrahydrofuran and stirred at room temperature. Benzoyl thioisocyanate (1 equivalent) was added dropwise to the reaction mixture. The resulting mixture was stirred at room temperature for 24 hours, and the solvent was removed under reduced pressure to afford a yellow oil.

The yellow oil (1 equivalent) was then dissolved in methanol, an aqueous potassium carbonate (3 equivalents) solution added, and the mixture stirred for 48 hours. Water was added to the reaction mixture which was then extracted with 2×75 ml ethyl acetate. The combined extracts were washed with water, dried with anhydrous sodium sulfate, filtered and the solvent removed under reduced pressure to give the desired thiourea.

tert-Butyl 5-[(aminocarbothioyl)amino]pentylcarbamate was obtained as a light yellow wax from tert-butyl 5-{[(benzoylamino)carbothioyl]amino}-pentylcarbamate. $^1$H NMR (CD$_3$OD) δ 3.44 (m, 1H), 3.10 (m, 1H), 3.01 (t, 2H, J=6.7 Hz), 1.60–1.31 (m, 6H), 1.41 (s, 9H); 262 (ESMS, MH$^+$).

tert-Butyl 5-{[(benzoylamino)carbothioyl]amino}pentylcarbamate was obtained a light yellow solid in 79% yield from N-BOC-1,5-diaminopentate and benzoyl isothiocyanate; m.p. 90–93° C.; $^1$H NMR δ (17001-131-1)

tert-Butyl 4-[(aminocarbothioyl)amino]butylcarbamate was obtained as a light yellow wax from tert-butyl 4-{[(benzoylamino)carbothioyl]amino}-butylcarbamate. $^1$H NMR (CD$_3$OD) δ 3.48 (m, 1H), 3.10 (m, 1H), 3.05 (t, 2H, J=6.5 Hz), 1.60 (m, 4H), 1.42 (s, 9H); 248 (ESMS, MH$^+$).

tert-Butyl 4-{[(benzoylamino)carbothioyl]amino}butylcarbamate was obtained as a light brown oil in 93% yield from N-BOC-1,4-diaminobutane and benzoyl isothiocyanate.

trans-tert-Butyl-{4-[(aminocarbothioyl)amino]cyclohexyl}methylcarbamate was obtained as a light yellow wax from trans-tert-butyl (4-{[(benzoylamino)carbothioyl]amino}cyclohexyl)methylcarbamate. $^1$H NMR (CD$_3$OD) δ 3.92 (m, 1H), 2.86 (m, 2H), 2.00 (m, 2H), 1.76 (m, 2H), 1.41 (s, 9H), 1.37 (m, 1H), 1.06 (m, 4H); 288 (ESMS, MH$^+$).

trans-tert-Butyl (4-{[(benzoylamino)carbothioyl]amino}cyclohexyl)-methylcarbamate was obtained as a yellow solid in 97% yield from tert-butyl 4-aminocyclohexylmethylcarbamate and benzoyl isothiocyanate.

trans-tert-Butyl 4-aminocyclohexylmethylcarbamate was obtained in more than 95% yield by hydrogenation of benzyl 4-{[(tert-butoxycarbonyl)amino]methyl}cyclocarbamate.

Benzyl-4-[[[tert-butoxycarbonyl]amino]methyl]cyclohexylcarbamate: To a stirred suspension of 4-[[(tert-butoxycarbonyl)amino]methyl]cyclohexanecarboxylic acid (Maybridge Chemical Co., Ltd.) (45 g) and diphenylphosphoryl azide (44 ml) in toluene (600 ml) was added triethylamine (32 ml) over a period of 20 min whilst maintaining the internal temperature at −10–0° C. The mixture was slowly warmed and then stirred at 70° C. for 4 h. After cooling to 40° C., benzyl alcohol (36 ml) was added and the reaction mixture heated at reflux for 20 h. The cold reaction mixture was washed with water and brine and dried over anhydrous magnesium sulfate. Removal of the solvent and recrystallization of the organic residue from ethyl acetate and diethyl ether gave the title compound, benzyl-4-[[[tert-butoxycarbonyl]amino]methyl]cyclohexylcarbamate as a white solid, m.p. 129–131° C.

trans-tert-Butyl {4-[(aminocarbothioyl)amino]cyclohexyl}carbamate was obtained as a yellow solid from trans-tert-Butyl4-(benzoylamino)carbothioyl]amino}cyclohexyl)-carbamate: $^1$H NMR (CD$_3$OD) δ 3.94 (m, 1H), 3.30 (m, 1H), 2.00 (m, 2H), 1.90 (m, 2H), 1.41 (s, 9H), 1.26 (m, 4H); 274 (ESMS, MH$^+$).

trans-tert-Butyl-4-{[(benzoylamino)carbothioyl]amino}cyclohexyl)carbamate was obtained as a white soilid in 66% yield from tert-butyl 4-aminocyclohexylcarbamate and benzoyl isothiocyanate.

trans-tert-Butyl 4-aminocyclohexylcarbamate was obtained as a light yellow wax in more than 95% yield by hydrogenation of benzyl 4-[(tert-butoxycarbonyl)amino]cyclohexylcarbamate.

trans-Benzyl 4-{[(aminocarbothioyl)amino]methyl}cyclohexylcarbamate was obtained as a yellow solid in 71% yield from trans-Benzyl-4-{[(Benzoylamino)carbothioyl]-amino}methyl)-cyclohexylcarbamate; 322 (ESMS, MH+).

trans-Benzyl-4-({[(benzoylamino)carbothioyl]amino}methyl)-cyclohexylcarbamate was obtained as a yellow solid from benzyl 4-(aminomethyl)cyclohexylcarbamate and benzoyl isothiocyanate.

trans-Benzyl 4-(aminomethyl)cyclohexylcarbamate was obtained as a white solid in more than 95% yield by stirring benzyl-4-{[(tert-butoxycarbonyl)amino]methyl}cyclocarbamate in 2N HCl (made from 1:1 of EtOAc and 4N HCl in dioxane).

General Procedure for the Synthesis of Tricyclic Thiazoles

A mixture of a bromoketone such as 6-bromo-3-fluoro-6,7,8,9-tetrahydro-5H-benzo[a]cyclohepten-5-one (1.2 equivalent), thiourea (1 equivalent), and diisopropylethylamine (2 equivalents) in anhydrous ethanol was stirred and heated at reflux overnight. The solvent was evaporated and the brown residue dissolved in dichloromethane and washed with saturated aqueous sodium bicarbonate. The mixture was extracted with dichloromethane three times. The combined extracts were dried over anhydrous sodium sulfate and the solvent removed to afford a crude product which was purified by flash column chromatography (silica gel).

General Procedure for the Deprotection of BOC-Protected Amines:

The Boc protected amine was dissolved in $Et_2O$. The same volume of 4N HCl in dioxane was added to make a 2N solution of HCl. The reaction mixture was stirred at room temperature overnight, and the solvent removed under reduced pressure to afford the desired product as its HCl salt.

tert-Butyl-5-[(9-fluoro-5,6-dihydro-4H-benzo[6,7]cyclohepta[1,2-d][1,3]thiazol-2-yl)amino]pentylcarbamate was obtained as a light yellow oil in 80% yield from 6-bromo-3-fluoro-6,7,8,9-tetrahydro-5H-benzo[a]cyclohepten-5-one and tert-butyl 5-[(aminocarbothioyl)amino]-pentylcarbamate: $^1H$ NMR δ 7.70 (dd, 1H, J=2.7, 10.8 Hz), 7.05 (dd, 1H, J=6.0, 8.4 Hz), 6.83 (td, 1H, J=2.7, 8.4 Hz), 5.12 (m, 1H), 4.53 (m, 1H), 3.26 (q, 2H, J=5.7 Hz), 3.14 (m, 2H), 2.89 (t, 2H, J=6.9 Hz), 2.79 (m, 2H), 2.09 (m, 2H), 1.68 (m, 4H), 1.50 (m, 2H), 1.44 (s, 9H); 420 (ESMS, MH+).

N-(5-Aminopentyl)-N-(9-fluoro-5,6-dihydro-4H-benzo[6,7]cyclohepta[1,2-d][1,3]thiazol-2-yl)amine dihydrogen chloride was obtained as a yellow solid in more than 95% yield from deprotection of tert-butyl 5-[(9-fluoro-5,6-dihydro-4H-benzo[6,7]cyclohepta[1,2-d][1,3]thiazol-2-yl)amino]pentylcarbamate by using 2N HCl (made from 1:1 of ethyl acetate and 4N HCl in dioxane); $^1H$ NMR ($CD_3OD$) δ 7.38–7.31 (m, 2H), 7.10 (td, 1H, J=2.4, 8.4 Hz), 3.71 (m, 2H), 3.49 (t, 2H, J=6.9 Hz), 2.95 (m, 2H), 2.78 (m, 2H), 2.17 (m, 2H), 1.85–1.68 (m, 4H), 1.54 (m, 2H); 320 (ESMS, MH+). tert-Butyl-4-[(9-fluoro-5,6-dihydro-4H-benzo[6,7]cyclohepta[1,2-d][1,3]thiazol-2-yl)amino]butylcarbamate was obtained as a yellow oil in 31% yield from 6-bromo-3-fluoro-6,7,8,9-tetrahydro-5H-benzo[a]cyclohepten-5-one and tert-butyl 4-[(aminocarbothioyl)amino]-butylcarbamate: $^1H$ NMR δ 7.70 (dd, 1H, J=3.0, 10.8 Hz), 7.05 (dd, 1H, J=6.0, 8.4 Hz), 6.82 (td, 1H, J=3.0, 8.3 Hz), 5.14 (m, 1H), 4.59 (m, 1H), 3.30 (m, 2H), 3.18 (m, 2H), 2.86 (t, 2H, J=6.9 Hz), 2.79 (m, 2H), 2.10 (m, 2H), 1.74–1.53 (m, 4H), 1.44 (s, 9H).

N-(4-Aminobutyl)-N-(9-fluoro-5,6-dihydro-4H-benzo[6,7]cyclohepta[1,2-d][1,3]thiazol-2-yl)amine hydrogen chloride was obtained as a yellow solid in more than 95% yield by deprotection of tert-butyl 4-[(9-fluoro-5,6-dihydro-4H-benzo[6,7]cyclohepta[1,2-d][1,3]thiazol-2-yl)amino]butylcarbamate with 2N HCl (made from 1:1 of 4N HCl in dioxane and ethyl acetate): $^1H$ NMR ($CD_3OD$) δ 7.39–7.31 (m, 2H), 7.10 (td, 1H, J=3.0, 8.4 Hz), 3.54 (m, 2H), 2.97 (m, 2H), 2.79 (m, 4H), 2.18 (m, 2H), 1.83 (m, 4H). (no MS).

trans-tert-Butyl-{4-[(9-fluoro-5,6-dihydro-4H-benzo[6,7]cyclohepta-[1,2-d][1,3]thiazol-2-yl)amino]cyclohexyl}methylcarbamate was obtained as a yellow oil in 80% yield from 6-bromo-3-fluoro-6,7,8,9-tetrahydro-5H-benzo[a]cyclohepten-5-one and trans-tert-butyl {4-[(aminocarbothioyl)-amino]cyclohexyl}methylcarbamate: $^1H$ NMR δ 7.69 (dd, 1H, J=2.8, 10.8 Hz), 7.05 (dd, 1H, J=5.9, 8.4 Hz), 6.82 (td, 1H, J=2.7, 8.3 Hz), 4.87 (m, 1H), 4.61 (m, 1H), 3.28 (m, 1H), 3.00 (m, 1H), 2.85 (t, 2H, J=6.9 Hz), 2.79 (m, 2H), 2.22 (m, 2H), 2.08 (m, 2H), 1.85 (m, 2H), 1.74 (m, 1H), 1.44 (s, 9H), 1.45–1.02 (m, 4H); 446 (ESMS, MH+).

N-(4-Aminomethyl)cyclohexyl]-N-(9-fluoro-5,6-dihydro-4H-benzo[6,7]cyclohepta[1,2-d][1,3]thiazol-2-yl)amine hydrogen chloride was obtained as a yellow solid in more than 95% yield by deprotection of tert-butyl {4-[(9-fluoro-5,6-dihydro-4H-benzo[6,7]cyclohepta[1,2-d][1,3]thiazol-2-yl)amino]cyclohexyl}methylcarbamate: $^1H$ NMR ($CD_3OD$) δ 7.34 (td, d 2H, J=2.7, 9.6 Hz), 7.11 (m, 1H), 3.61 (m, 1H), 2.82–2.76 (m, 6H), 2.18 (m, 4H), 1.96 (m, 2H), 1.69 (m, 1H), 1.50 (m, 2H), 1.24 (m, 2H); 346 (ESMS, MH+).

trans-tert-Butyl-4-[(9-fluoro-5,6-dihydro-4H-benzo[6,7]cyclohepta-[1,2-d][1,3]thiazol-2-yl)amino]cyclohexylcarbamate was obtained as a yellow solid in 59% yield from 6-bromo-3-fluoro-6,7,8,9-tetrahydro-5H-benzo[a]cyclohepten-5-one and trans-tert-butyl {4-[(aminocarbothioyl)-amino]cyclohexyl}carbamate: $^1H$ NMR δ 7.69 (dd, 1H, J=2.7, 10.8 Hz), 7.04 (dd, 1H, J=6.0, 8.1 Hz), 6.82 (td, 1H, J=2.7, 8.2 Hz), 4.95 (m, 1H), 4.45 (m, 1H), 3.39 (m, 2H), 2.84 (t, 2H, J=6.9 Hz), 2.77 (m, 2H), 2.10 (m, 2H), 2.07 (m, 4H), 1.44 (s, 9H), 1.28 (m, 4H); 432 (ESMS, MH+).

N-(4-Aminocyclohexyl)-N-(9-fluoro-5,6-dihydro-4H-benzo[6,7]cyclohepta[1,2-d][1,3]thiazol-2-yl)amine hydrogen chloride was obtained as a yellow soilid in more than 95% yield by deprotection of tert-butyl 4-[(9-fluoro-5,6-dihydro-4H-benzo[6,7]cyclohepta[1,2-d][1,3]thiazol-2-yl)amino]-cyclohexyl carbamate with 2N HCl (made from 1:1 of ethyl acetate and 4N HCl in dioxane): $^1H$ NMR ($CD_3OD$) δ 7.35 (m, 2H), 7.12 (m, 1H), 3.68 (m, 1H), 3.17 (m, 1H), 2.76 (m, 4H), 2.25–2.13 (m, 6H), 1.59 (m, 4H); 332 (ESMS, MH+).

trans-tert-Butyl-{4-[(8-Methoxy-5,6-dihydro-4H-benzo[6,7]cyclohepta[1,2-d][1,3]thiazol-2-yl)amino]cyclohexyl}methylcarbamate was obtained as a light yellow oil in 46% yield from 6-bromo-2-methoxy-6,7,8,9-tetrahydro-5H-benzo[a]cyclohepten-5-one and trans-tert-butyl-{4-[(aminocarbothioyl)amino]cyclohexyl}methylcarbamate; 458 (ESMS, MH+).

N-[4-(Aminomethyl)cyclohexyl]-8-methoxy-5,6-dihydro-4H-benzo[6,7]cyclohepta[1,2-d][1,3]thiazol-2-amine hydrogen chloride was obtained as a yellow solid in more than 95% yield by deprotection of trans-tert-butyl-{4-[(8-methoxy-5,6-dihydro-4H-benzo[6,7]cyclohepta[1,2-d][1,3]thiazol-2-yl)amino]cyclohexyl}methylcarbamate) with 2N HCl (made from 1:1 of ethyl acetate and 4N HCl in dioxane): $^1$H NMR (CD$_3$OD) δ 7.48 (m, 1H), 6.91 (m, 2H), 3.81 (s, 3H), 3.54 (m, 1H), 2.83–2.70 (m, 6H), 2.10 (m, 4H), 1.95 (m, 2H), 1.70 (m, 1H), 1.50 (m, 2H), 1.24 (m, 2H); 358 (ESMS, MH$^+$).

Benzyl-{4-[(8-Methoxy-5,6-dihydro-4H-benzo[6,7]cyclohepta[1,2-d][1,3]thiazol-2-yl)amino]methyl}cyclohexylcarbamate was obtained as a light yellow oil in 60% yield from 6-bromo-2-methoxy-6,7,8,9-tetrahydro-5H-benzo[a]cyclohepten-5-one and trans-benzyl-4-{[(aminocarbothioyl)amino]methyl}cyclohexylcarbamate: $^1$H NMR δ 7.88 (d, 1H, J=8.6 Hz), 7.35 (m, 5H), 6.79 (dd, 1H, J=2.4, 8.8 Hz), 6.68 (d, 1H, J=2.6 Hz), 5.30 (m, 1H), 5.08 (s, 2H), 4.62 (m, 1H), 3.81 (s, 3H), 3.45 (m, 1H), 3.08 (m, 2H), 2.83 (t, 2H, J=7.0 Hz), 2.77 (m, 2H), 2.08 (m, 4H), 1.85 (m, 2H), 1.55 (m, 1H), 1.10 (m, 4H); 492 (ESMS, MH$^+$).

N-[4-(Aminocyclohexyl)methyl]-8-methoxy-5,6-dihydro-4H-benzo[6,7]cyclohepta[1,2-d][1,3]thiazol-2-amine trifluoroacetic acid salt was obtained as a brown syrup in more than 95% yield by refluxing benzyl {4-[(8-methoxy-5,6-dihydro-4H-benzo[6,7]cyclohepta[1,2-d][1,3]thiazol-2-yl)amino]methyl}cyclohexylcarbamate in TFA/H$_2$O (95:5) for 1 hour: $^1$H NMR (CD$_3$OD) δ 7.47 (d, 1H, J=8.4 Hz), 6.86 (m, 2H), 3.80 (s, 3H), 3.28 (m, 2H), 3.07 (m, 1H), 2.79–2.73 (m, 4H), 2.17–2.05 (m, 4H), 1.97 (m, 2H), 1.75 (m, 1H), 1.42 (m, 2H), 1.23 (m, 2H); 358 (ESMS, MH$^+$).

tert-Butyl {4-[(7-Methoxy-4,5-dihydro[1]benzoxepino[5,4-d][1,3]thiazol-2-yl)amino]cyclohexyl}methylcarbamate was obtained as a light yellow oil in 69% yield from 4-bromo-9-methoxy-3,4-dihydro-1-benzoxepin-5(2H)-one and trans-tert-butyl {4-[(aminocarbothioyl)amino]cyclohexyl}methylcarbamate: $^1$H NMR δ 7.85 (dd, 1H, J=1.5, 8.2 Hz), 7.02 (t, 1H, J=8.1 Hz), 6.81 (dd, 1H, J=1.4, 8.0 Hz), 4.83 (m, 1H), 4.60 (m, 1H), 4.40 (t, 2H, J=5.1 Hz), 3.88 (s, 3H), 3.29 (m, 1H), 3.18 (t, 2H, J=5.1 Hz), 3.00 (m, 2H), 2.24 (m, 2H), 1.85 (m, 2H), 1.60 (m, 1H), 1.45 (s, 9H); 460 (ESMS, MH$^+$).

N-[4-(Aminomethyl)cyclohexyl]-7-methoxy-4,5-dihydro[1]-benzoxepino[5,4-d][1,3]thiazol-2-amine hydrogen chloride was obtained as a yellow solid in more than 95% yield by stirring tert-butyl {4-[(7-methoxy-4,5-dihydro[1]benzoxepino[5,4-d][1,3]thiazol- 2-yl)amino]cyclohexyl}methylcarbamate in 2N HCl (made from 1:1 of ethyl acetate and 4N HCl in dioxane) for 3 hr: $^1$H NMR (CD$_3$OD) δ 7.25 (m, 1H), 7.20–7.06 (m, 2H), 4.32 (m, 2H), 3.85 (s, 3H), 3.56 (m, 1H), 3.19 (m, 2H), 2.86 (m, 2H), 2.21 (m, 2H), 1.94 (m, 2H), 1.73 (m, 1H), 1.55 (m, 2H), 1.27 (m, 2H); 360 (ESMS, MH$^+$).

tert-Butyl [4-(4H-Chromeno[4,3-d][1,3]thiazol-2-yiamino)cyclohexyl]-methylcarbamate was obtained as a light yellow oil from 3-Bromo-2,3-dihydro-4H-chromen-4-one and trans-tert-butyl {4-[(aminocarbothioyl)amino]cyclohexyl}methylcarbamate: $^1$H NMR δ 7.58 (dd, 1H, J=1.5, 7.5 Hz), 7.12 (m, 1H), 6.96 (m, 1H), 6.87 (dd, 1H, J=0.6, 8.1 Hz), 5.07 (m, 1H), 4.60 (m, 1H), 3.29 (m, 1H), 3.00 (m, 2H), 2.07 (m, 2H), 1.85 (m, 2H), 1.50 (m, 1H), 1.45 (s, 9H), 1.25 (m, 2H), 1.05 (m, 2H); 416 (ESMS, MH$^+$).

N-[4-(Aminomethyl)cyclohexyl]-4H-chromeno[4,3-d][1,3]thiazol-2-amine hydrogen chloride was obtained as a yellow solid in more than 95% yield by stirring tert-butyl [4-(4H-chromeno[4,3-d][1,3]thiazol-2-yiamino)cyclohexyl]methylcarbamate in 2N HCl (made from 1:1 of ethyl acetate and 4N HCl in dioxane) for 3 hr: $^1$H NMR (CD$_3$OD) δ 7.65 (dd, 1H, J=1.3, 7.8 Hz), 7.29 (td, 1H, J=1.5, 7.8 Hz), 7.06 (td, 1H, J=1.0, 7.7 Hz), 6.97 (dd, 1H, J=0.9, 8.4 Hz), 5.23 (s, 2H), 3.73 (m, 1H), 2.84 (m, 2H), 2.21 (m, 2H), 1.95 (m, 2H), 1.70 (m, 1H), 1.50 (m, 2H), 1.25 (m, 2H); 316 (ESMS, MH$^+$).

trans-N2-(4-(2-Methoxyethoxycarbonyl)aminomethyl) cyclohexyl-9-fluoro-5,6-dihydro-4H-benzo[6,7]cyclohepta-[d][1,3]-thiazol-2-amine:

a. t-Butyl-trans-N-(4-(Benzoylaminocarbothioylamino) cyclohexyl)methyl-carbamate: A solution of t-butyl trans-N-(4-aminocyclohexyl)methylcarbamate (4.683 g, 20.51 mmol) and benzoylisothiocyanate (3.77 g, 23.1 mmol) in THF (180 mL) was stirred at room temperature for 20 hours. The solvent was removed in vacuo to yield a golden viscous oil. The oil was triturated with hexane (250 mL) and the resulting solid was collected by filtration and washed with hexane to yield 91% (7.32 g) of the product as an off-white solid: $^1$H NMR (CDCl$_3$) δ 1.20 (6H, m), 1.44 (9H, s), 1.83 (2H, m), 2.25 (2H, m), 3.01 (2H, t, J=6.4 Hz), 4.20 (1H, m), 4.62 (1H, m), 7.51 (2H, t, J=7.9 Hz), 7.60 (1H, t, J=7.4 Hz), 7.81 (2H, d, J=7.2 Hz), 8.93 (1H, s); 392 (ESMS, MH$^+$).

b. t-Butyl trans-N-(4-(aminocarbothioylamino) cyclohexyl)methylcarbamate: To a solution of t-butyl trans-N-(4-(benzoylaminocarbothioylamino)cyclohexyl) methylcarbamate (7.30 g, 18.6 mmol) in MeOH (110 mL) was added a solution of potassium carbonate (5.15 g, 37.3 mmol) in water (50 mL). The solution was stirred at room temperature for 18 hours. The solvent was removed in vacuo and the residue was extracted several times with EtOH. The combined EtOH extracts were evaporated to dryness to yield 6.15 g of an off-white solid. The solid was dissolved in acetone (200 mL) and stirred for 20 minutes. The solution was filtered by suction to remove any insoluble salts and the filtrate evaporated to yield 98% (5.23 g) of the desired product as a slightly yellow solid: $^1$H NMR (CDCl$_3$) δ 1.10 (6H, m), 1.43 (9H, s), 1.80 (2H, m), 2.10 (2H, m), 2.95 (2H, t, J=6.4 Hz), 4.75 (1H, broad), 6.03 (2H, s), 6.64 (1H, broad); 288 (ESMS, MH$^+$).

c. 6-Bromo-3-fluoro-6,7,8,9-tetrahydro-5H-benzo[a] cyclohepten-5-one: To a solution of 8-fluoro-1-benzosuberone (20.00 g, 112.2 mmol) in glacial acetic acid (125 ml) was added bromine (5.8 mL, 112.6 mmol) dropwise. After addition was complete, the solution was poured into water (400 ml) and extracted with EtOAc (500 ml). The EtOAc layer was separated and washed with water (500 ml). The organic layer was dried over MgSO$_4$, filtered and evaporated to yield 100% (28.9 g) of the desired product as a viscous oil: $^1$H NMR (CDCl$_3$) δ 2.00 (2H, m), 2.33 (2H, m), 2.84 (1H, m), 3.00 (1H, m), 4.83 (1H, m), 7.13 (2H, m), 7.29 (1H, dd).

d. t-Butyl trans-N-(4-(9-fluoro-5,6-dihydro-4H-benzo[6,7]cyclohepta[d][1,3]-thiazol-2-ylamino)cyclohexyl) methylcarbamate: A solution of t-butyl trans-N-(4-(aminocarbothioylamino)cyclohexyl)methylcarbamate (22.4 g, 78.0 mmol), 6-bromo-3-fluoro-6,7,8,9-tetrahydro-5H-benzo[a]cyclohepten-5-one (20.05 g, 78.0 mmol) and N,N-diisopropylethylamine (22.5 ml) in absolute ethanol (260 ml) was heated at reflux for 3 hours. The solvent was removed in vacuo, and the resulting viscous golden oil was taken up in EtOAc (400 ml) and washed with water (600 ml). The EtOAc layer was separated and evaporated to yield 39.0 g of a viscous golden oil. The oil was chromatographed over silica gel eluting with EtOAc to yield 34.5 g of the desired product (99% yield): $^1$H NMR (CDCl$_3$) δ 1.18 (6H, h, J=12.2 Hz), 1.44 (9H, s), 1.81 (2H, m), 2.22 (2H, m), 2.79

(2H, m), 2.86 (2H, t, J=7.1 Hz), 3.00 (2H, t, J=6.3 Hz), 3.25 (1H, broad), 4.62 (1H, broad), 4.86 (1H, broad), 6.83 (1H, dt, J=2.9 Hz), 7.04 (1H, m), 7.70 (1H, dd, J=2.8 Hz).

e. trans-N2-(4-Aminomethyl)cyclohexyl-9-fluoro-5,6-dihydro-4H-benzo[6,7]cyclohepta[d][1,3]-thiazol-2-amine hydrochloride: A solution of t-butyl trans-N-(4-(9-fluoro-5,6-dihydro-4H-benzo[6,7]cyclohepta[d][1,3]thiazol-2-ylamino)cyclohexyl)-methylcarbamate (34.5 g, 77.0 mmol) in EtOAc (200 ml) and 4N HCl in dioxane (100 ml) was stirred at room temperature for 2 hours. The resulting solid was collected by filtration, washed with Et$_2$O and dried under vacuum to yield 25.9 g of the desired product as a slightly yellow solid. An additional 1.43 g of the product was obtained by allowing the filtrate to stand in a closed flask for several days. The overall yield was 85%: ESMS m/e=346 (MH$^+$); $^1$H NMR (CD$_3$OD) δ 1.25 (2H, m), 1.51 (2H, m), 1.70 (1H, broad), 1.95 (2H, m), 2.18 (4H, m), 2.80 (6H, m), 3.63 (1H, broad), 7.11 (1H, dt, J=2.5 Hz, 8.4 Hz), 7.36 (2H, m).

f. trans-N2-(4-(2-Methoxyethoxycarbonyl)aminomethyl)cyclohexyl-9-fluoro-5,6-dihydro-4H-benzo[6,7]cyclohepta[d][1,3]-thiazol-2-amine: A solution of trans-N2-(4-aminomethyl)cyclohexyl-9-fluoro-5,6-dihydro-4H-benzo[6,7]cyclohepta[d][1,3]thiazol-2-amine hydrochloride (0.30 g, 0.72 mmol) and triethylamine (1.0 ml) in anhydrous THF (3 ml) was treated dropwise with chloroformic acid 2-methoxyethyl ester (0.114 g, 0.82 mmol). The solution was stirred at room temperature for 2 hours. The solvent was removed in vacuo and the residue chromatographed over silica gel eluting with 1:1 EtOAc/Hexane to yield the desired product (80 mg, 25% yield) as a highly viscous colorless oil: 448 (ESMS, MH$^+$); $^1$H NMR (CDCl$_3$) δ 1.11 (4H, h, J=9.8 Hz), 1.42 (1H, broad), 1.80 (2H, m), 2.04 (2H, m), 2.20 (2H, m), 2.77 (2H, m), 2.84 (2H, t, J=6.9 Hz), 3.04 (2H, t, J=6.4 Hz), 3.24 (1H, broad), 3.38 (3H, s), 3.58 (2H, m), 4.22 (2H, m), 4.90 (1H, broad), 5.00 (1H, d), 6.81 (1H, dt, J=2.8 Hz), 7.03 (1H, m), 7.68 (1H, dd, J=2.7 Hz, 10.9 Hz).

Similarly prepared were:

N2-(5-Aminopent-1-yl)-9-fluoro-5,6-dihydro-4H-benzo[6,7]cyclohepta[d][1,3]thiazol-2-amine hydrochloride: Yellow solid; m.p. 220° C. (dec.); 320 (ESMS, MH$^+$); $^1$H NMR (CD$_3$OD) δ 7.34 (m, 2H), 7.10 (td, 1H, J=2.4, 8.4 Hz), 3.49 (t, 2H, J=7.0 Hz), 2.95 (t, 2H, J=7.7 Hz), 2.78 (m, 4H), 2.17 (m, 2H), 1.82–1.67 (m, 4H), 1.54 (m, 2H).

General Procedure for the Derivatization of Amines with Carboxylic Acid and Sulfonic Acid Derivatives An amine such as N-[4-(aminomethyl)cyclohexyl]-4H-chromeno[4,3-d][1,3]thiazol-2-amine (0.305 mmol) was dissolved in 2 ml CH$_2$Cl$_2$ with 1–3 equivalents of diisopropylethylamine. The appropriate sulfonyl chloride, acid chloride, isocyanate or carbamyl chloride (1–3 equivalents) was then added dropwise. The reaction solution was stirred at room temperature for 1–3 days, quenched with water and washed with 10% NaHCO$_3$, extracted with EtOAc, and then dried over Na$_2$SO$_4$. The crude product was purified using column chromatography or preparative TLC.

General Procedure for the Formation of Formamides

The following sequence for the preparation of formamides is typical:

N2-[4-(aminomethyl)phenyl]-9-fluoro-5,6-dihydro-4H-benzo[6,7]cyclohepta[d][1,3]thiazol-2-amine-tert-butyl N-(4-aminobenzyl)carbamate: To a stirred solution of 4-amino-benzylamine (7.5 g, 61.39 mmol) in anhydrous THF (100 ml) under N$_2$ was added, in portions, di-t-butyl dicarbonate (13.5 g, 61.9 mmol). The solution was stirred at room temperature under N$_2$ for 90 minutes. The solvent was removed in vacuo to yield 100% (13.7 g) of the Boc-protected amine as a white solid: m.p. 70–72° C. $^1$H-NMR (CDCl$_3$) δ 1.43 (9H, s), 3.62 (2H, broad), 4.18 (2H, d), 4.77 (1H, broad), 6.63 (2H, d), 7.06 (2H, d).

tert-butyl N-(4-{[(benzoylamino)carbothioyl]amino}benzyl)carbamate: To a stirred solution of N2-[4-(aminomethyl)phenyl]-9-fluoro-5,6-dihydro-4H-benzo[6,7]cyclohepta[d][1,3]thiazol-2-amine-tert-butyl N-(4-aminobenzyl)carbamate (6.00 g, 27.0 mmol) in anhydrous THF (50 ml) was added benzoylisothiocyanate (4.43 g, 27.0 mmol). The solution was stirred for 2 hours and the solvent removed in vacuo to yield 100% (10.4 g) of the protected thiourea as a yellow solid: m.p. 161–163° C. $^1$H-NMR (CDCl$_3$) δ 1.45 (9H, s), 4.33 (2H, d), 4.85 (1H, broad), 7.34 (2H, d), 7.60 (5H, m), 7.90 (2H, d), 9.13 (1H, s), 12.58 (1H, s); 386 (ESMS, MH$^+$).

tert-butyl N-{4-[(aminocarbothioyl)amino]benzyl}carbamate: To a stirred solution of tert-butyl N-(4-{[(benzoylamino)carbothioyl]amino}benzyl)carbamate 10.4 g, 27.0 mmol) in MeOH (150 ml) (not completely dissolved) was added a solution of K$_2$CO$_3$ (8.5 g, 61.5 mmol) in circa. 15 ml water. The solution was stirred at room temperature for 24 hours and filtered to remove a white precipitate. The filtrate was evaporated in vacuo to yield 100% (7.6 g) of an off-white solid.

tert-butyl N-{4-[(9-fluoro-5,6-dihydro-4H-benzo[6,7]cyclo-hepta[d][1,3]thiazol-2-yl)amino]benzyl}carbamate: A solution containing tert-butyl N-{4-[(aminocarbothioyl)amino]benzyl}carbamate (7.60 g, 27.0 mmol), 6-bromo-3-fluoro-6,7,8,9-tetrahydro-5H-benzo[a]cyclohepten-5-one (6.95 g, 27.0 mmol), and diisopropylethylamine (5.0 ml) in EtOH (60 ml) was heated at reflux for 2.5 hours. The solvent was removed in vacuo and the residue dissolved in EtOAc (125 ml). The resulting solution was filtered to remove the insoluble (i-pr)$_2$NEt·HBr. The filtrate was transferred to a 250 ml round bottom flask and 4N HCl in dioxane (35 ml) added with stirring. The solution was stirred for 90 minutes and filtered to collect the hydrochloride salt. The solid was washed with EtOAc and then with Et$_2$O. Upon drying, 86% (11.1 g) of the Boc-protected amine hydrochloride was obtained as a slightly yellow solid: $^1$H-NMR (d$_4$-MeOH) δ 1.43 (9H, s), 2.18 (2H, m), 2.80 (4H, m), 4.25 (2H, s), 7.12 (1H, dt), 7.33 (2H, m), 7.43 (4H, s).

2-(4-aminomethyl)anilino-1-aza-9-fluoro-4,5-dihydro-3-thia-benzo[e]azulene: To a stirred solution of tert-butyl N-{4-[(9-fluoro-5,6-dihydro-4H-benzo[6,7]cyclohepta[d][1,3]-thiazol-2-yl)amino]benzyl}carbamate (11.1 g, 23.3 mmol) in MeOH (150 ml) (partially dissolved) was added 4N HCl in dioxane (40 ml). The solution was brought to a brief gentle reflux and the solvent was then removed in vacuo. The resulting solid was re-suspended in Et$_2$O, filtered and dried to yield 90% (9.25 g) of the product dihydrochloride as a white solid: m.p. 236–239° C. $^1$H-NMR (CDCl$_3$) δ 1.75 (2H, broad), 2.06 (2H, m), 2.77 (2H, m), 2.83 (2H, t), 3.79 (2H, s), 6.82 (1H, t), 7.04 (1H, m), 7.22 (4H, m), 7.79 (1H, dd), 8.8 (1H, broad); 340 (ESMS, MH$^+$).

N1-{4-[(9-fluoro-5,6-dihydro-4H-benzo[6,7]cyclohepta[d][1,3]thiazol-2-yl)amino]benzyl}-2-methoxyacetamide: To a stirred solution of 2-(4-aminomethyl)anilino-1-aza-9-fluoro-4,5-dihydro-3-thia-benzo[e]azulene (1.50 g, 3.64 mmol) in anhydrous pyridine (10 ml) and diisopropylethylamine (5.0 ml) was added methoxyacetyl chloride (0.40 ml, 4.38 mmol) dropwise. The solution was stirred overnight, poured into water (200 ml), and extracted with EtOAc (200 ml). The EtOAc extract was evaporated to yield 1.8 g of a viscous golden oil. The oil was chromatographed on silica-gel eluting with EtOAc to yield 80% (1.2 g) of the desired product as a foam. The product was converted to its HCl salt in chloroform using 1M HCl in Et$_2$O: m.p. 175–178° C.; $^1$H-NMR (CDCl$_3$) δ 2.15 (2H, m), 2.86 (4H, m), 3.42 (3H, s), 3.96 (2H, s), 4.50 (2H, d, J=6.1 Hz), 7.00 (1H, t), 7.18–7.40 (7H, m), 7.61 (1H, dd, J=2.5 Hz, 9.5 Hz); 412 (ESMS, MH$^+$).

N-{4-[(9-fluoro-5,6-dihydro-4H-benzo[6,7]cyclohepta[d][1,3]thiazol-2-yl)amino]benzyl}-N-isopropylformamide:

N2-{4-[(isopropylamino)methyl]phenyl}-9-fluoro-5,6-dihydro-4H-benzo[6,7]cyclohepta[d][1,3]thiazol-2-amine: A solution of 2-(4-aminomethyl)anilino-1-aza-9-fluoro-4,5-dihydro-3-thia-benzo[e]azulene (free-base) (0.54 g, 1.59 mmol), anhydrous THF (8 ml), anhydrous DMF (4 ml) and 2-iodopropane (1.4 g, 8.24 mmol) was heated to reflux for 1 hour. The solution was then stirred at room temperature overnight. TLC (95% EtOAc/5% 2M NH$_3$ in MeOH) indicated a major product (R$_f$~0.4) and some starting material. The solution was poured into water (200 ml) and extracted with EtOAc. The EtOAc layer was evaporated to yield 99% (0.6 g) of the product as a viscous golden oil. $^1$H NMR spectrum showed the presence of an isopropyl group (δ 1.08, CDCl$_3$) as a doublet. The amine was not purified before the next step.

1-aza-9-fluoro-4,5-dihydro-2-(4-(n-(2-propyl) formamido)-methyl)anilino-3-thia-benzo[e]azulene: To a stirred solution of N2-{4-[(isopropylamino)methyl]phenyl}-9-fluoro-5,6-dihydro-4H-benzo[6,7]cyclohepta[d][1,3] thiazol-2-amine (0.60 g, 1.57 mmol) in anhydrous THF (10 ml) was added 1H-benzotriazole-1-carboxaldehyde (0.245 g, 1.67 mmol). The solution was stirred for 30 minutes at room temperature, poured into 2N NaOH (60 ml) and extracted with EtOAc. The EtOAc layer was again washed with 2N NaOH (60 ml) and evaporated to yield 0.55 g of a viscous golden oil. The oil was chromatographed on silica-gel eluting with 40% EtOAc/60% hexane to yield 23% (0.15 g) of the desired product as a viscous colorless oil. The oil was converted to its HCl salt in chloroform with 1N HCl in Et$_2$O. Upon evaporation of solvent and trituration with Et$_2$O, 104 mg of the desired HCl salt was isolated: m.p. 180–183° C. $^1$H-NMR (CDCl$_3$) δ 1.10 (1.5H, d, J=6.8 Hz), 1.20 (4.5H, d, 6.3 Hz), 2.10 (2H, m), 2.78 (2H, m), 2.83 (2H, m), 3.72 (1H, h), 4.30 (0.5H, s), 4.51 (1.5H, s), 6.82 (1H, m), 7.18 (3H, m), 7.34 (2H, m), 7.76 (1H, d), 8.23 (0.25H, s), 8.39 (1.75H, broad s); 410 (ESMS, MH$^+$).

EXAMPLE 1 trans-N2-(4-Dimethylaminosulfonylaminomethyl) yclohexyl-9-fluoro-5,6-dihydro-4H-benzo[6,7]cyclohepta[d][1,3]thiazol-2-amine a. trans-1-Aminocarbothioylamino-4-(dimethylaminosulfonyl-aminomethyl)-cyclohexane: 4-(Dimethylaminosulfonylamino-methyl)cyclohexylamine (500 mg, 2.12 mmol) was suspended in dry THF (8 mL), cooled in an ice water bath and treated dropwise with benzoylisothiocyanate (290 μL, 2.16 mmol). The yellow solution was stirred at room temperature overnight and then concentrated. The residual yellow solid was dissolved in chloroform and flash chromatographed over silica gel (49 g) eluting with EtOAc/hexane (2:3) to give a yellow solid (490 mg, 58%). This solid was suspended in MeOH (4 ml), cooled in a water bath and treated with potassium carbonate (170 mg, 1.23 mmol) in water (3 ml). The mixture was stirred at room temperature for 1 hour before more MeOH (2 ml) and water (1.5 ml) were added. After 3 hours, the organic solvent was evaporated and the aqueous layer extracted with dichloromethane and EtOAc. The combined extracts were dried (Na$_2$SO$_4$), filtered and concentrated to give a white foam (378 mg).

b. trans-N2-(4-Dimethylaminosulfonylaminomethyl) cyclohexyl-9-fluoro-5,6-dihydro-4H-benzo[6,7]cyclohepta[d][1,3]-thiazol-2-amine: 6-Bromo-3-fluoro-6,7,8,9-tetrahydro-5H-benzo[a]cyclohepten-5-one (69 mg, 0.27 mmol) and trans-1-aminocarbothioylamino-4-(dimethylaminosulfonylaminomethyl)-cyclohexane (119 mg, 0.40 mmol) were dissolved in EtOH (4 mL) and heated at reflux overnight. The solvent was evaporated and the residue partitioned between EtOAc and potassium carbonate solution. The organic phase was dried (Na$_2$SO$_4$), filtered and concentrated to give a light orange oil (179 mg) which was flash chromatographed over silica gel (14 g) eluting with EtOAc/hexane (2:3),o afford a pale yellow foam (105 mg, 86%): m.p. 60–65° C.; 453 (ESMS, MH$^+$); $^1$H NMR (CDCl$_3$) δ 1.15 (4H, m), 1.50 (1H, broad), 1.90 (2H, m), 2.07 (2H, m), 2.25 (2H, m), 2.80 (2H, m), 2.82 (6H, s), 2.86 (2H, t, J=6.9 Hz), 2.94 (2H, t, J=6.6 Hz), 3.33 (1H, broad), 4.18 (1H, m), 4.81 (1H, d, J=7.6 Hz), 6.83 (1H, m), 7.06 (1H, dd, J=6.0, 8.3 Hz), 7.69 (1H, dd, J=2.8, 10.8 Hz).

EXAMPLE 2

1-Aza-9-fluoro-4,5-dihydro-2-{5-(dimethylaminosulfonyl-amino)pentyl}amino-3-thia-benzo[e]azulene: 86% yield; 427 (ESMS, MH$^+$); $^1$H NMR (CDCl$_3$) δ 7.67 (dd, 1H, J=10.8, 3.0 Hz), 7.05 (dd, 1H, J=6.0, 8.2), 6.82 (apparent dt, 1H, J=2.8, 8.3 Hz), 5.74 (broad, 1H), 5.24 (t, 1H, J=5.7 Hz), 3.16 (q, 2H, J=4.2 Hz), 2.97 (q, 2H, J=6.3 Hz), 2.84 (t, 2H, J=6.9 Hz), 2.77 (s, 6H), 2.75 (masked m, 2H), 2.08 (m, 2H), 1.58 (p, 2H, J=6.75 Hz), 1.43 (p, 2H, J=6.9 Hz), 1.26 (p, 2H, J=7.2 Hz).

EXAMPLE 3

1-Aza-9-fluoro-2-(5-(2-fluorophenyl)sulfonylamino) pentylamino-4,5-dihydro-3-thia-benzo[e]azulene was obtained as a yellow oil in 36% yield; $^1$H NMR δ 7.89 (td, 1H, J=1.6, 7.5 Hz), 7.62 (dd, 1H, J=2.7, 10.8 Hz), 7.55 (m, 1H), 7.29–7.17 (m, 2H), 7.06 (dd, 1H, J=6.0, 8.1 Hz), 6.81 (td, 1H, J=3.0, 8.2 Hz), 5.44 (b, 2H), 3.16 (m, 2H), 2.95 (m, 2H), 2.84 (t, 2H, J=6.9 Hz), 2.08 (m, 2H), 1.58–1.25 (m, 6H); 478 (ESMS, MH$^+$); m.p. (HCl salt) 55–57° C.

EXAMPLE 4

1-Aza-9-fluoro-4,5-dihydro-2-(5-(1-naphthyl) sulfonylamino)-pentylamino-3-thia-benzo[e]azulene: was obtained as a yellow oil in 29% yield; $^1$H NMR δ 8.69 (d, 1H, J=8.7 Hz), 8.25 (dd, 1H, J=0.9, 7.2 Hz), 8.05 (d, 1H, J=8.4 Hz), 7.93 (d, 1H, J=8.1 Hz), 7.68–7.49 (m, 4H), 7.04 (dd, 1H, J=5.7, 8.1 Hz), 6.80 (td, 1H, J=2.9, 8.1 Hz), 5.52 (b, 1H), 5.41 (b, 1H), 3.01 (m, 2H), 2.89–2.74 (m, 6H), 2.07 (m, 2H), 1.39–1.12 (m, 6H); 510 (ESMS, MH$^+$).

EXAMPLE 5

1-Aza-9-fluoro-4,5-dihydro-2-(4-(methanesulfonylamino)-butyl)amino-3-thia-benzo[e] azulene was obtained as a yellow oil in 59% yield: $^1$H NMR δ 7.63 (dd, 1H, J=2.7, 10.8 Hz), 7.07 (dd, 1H, J=6.0, 8.4 Hz), 6.84 (td, 1H, J=2.9, 8.4 Hz), 5.61 (b, 1H), 5.34 (b, 1H), 3.22 (m, 2H), 3.09 (m, 2H), 2.94 (s, 3H), 2.86–2.76 (m, 4H), 2.09 (m, 2H), 1.60 (m, 6H); 384 (ESMS, MH$^+$).

EXAMPLE 6

1-Aza-9-fluoro-4,5-dihydro-2-(4-(dimethylaminosulfonyl-amino)butyl)amino-3-thia-benzo[e]azulene was obtained as a yellow oil in 75% yield: $^1$H NMR δ 7.65 (dd, 1H, J=2.4, 10.8 Hz), 7.06 (t, 1H, J=7.1 Hz), 6.83 (td, 1H, J=2.7, 8.1 Hz), 5.57 (b, 1H), 5.05 (b, 1H), 3.21 (m, 2H), 3.02 (q, 2H, J=5.7 Hz), 2.87–2.76 (m, 10H), 2.08 (m, 2H), 1.59 (m, 4H); 413 (ESMS, MH$^+$).

EXAMPLE 7

1-Aza-9-fluoro-2-(4-(2-fluorophenyl)sulfonylamino)butylamino-4,5-dihydro-3-thia-benzo[e]azulene was obtained as a light yellow oil in 81% yield: $^1$H NMR δ 7.88 (td, 1H, J=1.5, 9.0 Hz), 7.57 (m, 2H), 7.28–7.17 (m, 2H), 7.05 (dd, 1H, J=6.0, 8.1 Hz), 6.81 (td, 1H, J=2.7, 8.1 Hz), 5.64 (b, 2H), 3.14 (t, 2H, J=6.3 Hz), 2.95 (t, 2H, J=6.3 Hz), 2.83 (t, 2H, J=6.9 Hz), 2.76 (m, 2H), 2.06 (m, 2H), 1.52 (m, 4H); 464 (ESMS, MH$^+$).

EXAMPLE 8

1-Aza-9-fluoro-4,5-dihydro-2-(4-(1-naphthyl)sulfonylamino)butylamino-3-thia-benzo[e]azulene was obtained as a yellow oil in 78% yield: $^1$H NMR δ 8.68 (d, 1H, J=8.4 Hz), 8.24 (d, 1H, J=7.2 Hz), 8.05 (d, 1H, J=8.4 Hz), 7.93 (d, 1H, J=7.8 Hz), 7.66–7.50 (m, 4H), 7.05 (dd, 1H, J=6.0, 8.4 Hz), 6.80 (td, 1H, J=2.7, 8.1 Hz), 5.62 (b, 1H), 5.39 (b, 1H), 3.02 (m, 2H), 2.87–2.74 (m, 6H), 2.07 (m, 2H), 1.41 (m, 4H); 496 (ESMS, MH$^+$).

EXAMPLE 9

1-Aza-9-fluoro-4,5-dihydro-2-(4-((2(S)-methoxymethyl)-pyrrolidine-1-yl)sulfonyl)phenylamino-3-thia-benzo[e]azulene was obtained as a light yellow solid in 72% yield: m.p. 186–188° C. $^1$H NMR δ 7.94 (b, 1H), 7.76 (m, 3H), 7.57 (d, 2H, J=8.7 Hz), 7.11 (dd, 1H, J=6.0, 8.4 Hz), 3.75–3.64 (m, 2H), 3.45–3.32 (m, 2H), 3.38 (s, 3H), 3.11 (m, 1H), 2.94 (t, 2H, J=6.9 Hz), 2.83 (m, 2H), 2.15 (m, 2H), 1.84 (m, 2H), 1.60 (m, 2H); 488 (ESMS, MH$^+$).

The hydrogen chloride salt was obtained as a yellow solid: m.p. 151–155° C.

EXAMPLE 10

1-Aza-9-fluoro-4,5-dihydro-2-(5-(methylsulfonylamino)-pentyl)amino-3-thia-benzo[e]azulene (hydrogen chloride salt) was obtained as a yellow oil in 53% yield: $^1$H NMR (CD$_3$OD) δ 7.35 (dd, 1H, J=2.5, 9.9 Hz), 7.28 (dd, 1H, J=6.0, 8.4 Hz), 7.05 (td, 1H, J=2.5, 8.4 Hz), 3.42 (t, 2H, J=7.0 Hz), 3.06 (t, 2H, J=6.6 Hz), 2.90 (s, 3H), 2.78 (t, 4H, J=7.1 Hz), 2.14 (m, 2H), 1.74 (p, 2H, J=7.2 Hz), 1.63–1.47 (m, 4H); 398 (ESMS, MH$^+$).

EXAMPLE 11 trans-1-Aza-9-fluoro-4,5-dihydro-2-(4-(methylsulfonylamino-methyl)cyclohexyl)amino-3-thia-benzo[e]azulene: Anal. Calcd for C$_{20}$H$_{26}$FN$_3$O$_2$S$_2$+0.25H$_2$O: C, 56.12; H, 6.24; N, 9.82. Found: C, 56.15; H, 6.40; N, 9.52.

EXAMPLE 12

1-Aza-9-fluoro-4,5-dihydro-2-(5-(2,4-difluorophenyl)sulfonylamino)pentylamino-3-thia-benzo[e]azulene (hydrogen chloride salt) was obtained as a yellow syrup in 83% yield: $^1$H NMR (CD$_3$OD) δ 7.91 (m, 1H), 7.64 (dd, 1H, J=2.8, 10.8 Hz), 7.08–6.92 (m, 3H), 6.82 (td, 1H, J=2.8, 8.3 Hz), 5.23 (b, 2H), 3.21 (m, 2H), 2.97 (m, 2H), 2.86 (t, 2H, J=6.9 Hz), 2.78 (m, 2H), 2.07 (m, 2H), 1.63–1.34 (m, 6H); 496 (ESMS, MH$^+$).

EXAMPLE 13

1-Aza-9-fluoro-4,5-dihydro-2-(5-isopropylsulfonylamino)-pentylamino-3-thia-benzo[e]azulene (hydrogen chloride salt) was obtained as a yellow syrup in 12% yield: $^1$H NMR (free base) δ 7.69 (dd, 1H, JJ=3.0, 10.8 Hz), 7.05 (dd, 1H, J=5.9, 8.1 Hz), 6.82 (td, 1H, J=2.8, 8.1 Hz), 5.34 (b, 1H), 3.92 (t, 1H, J=6.0 Hz), 3.29–3.11 (m, 3H), 2.85 (t, 2H, J=6.9 Hz), 2.79 (m, 2H), 2.10 (m, 2H), 1.80 (s, 3H), 1.73 (s, 3H), 1.64 (m, 4H), 1.44 (m, 2H).

EXAMPLE 14

1-Aza-9-fluoro-4,5-dihydro-2-(5-(diethylaminosulfonyl-amino)pentyl)amino-3-thia-benzo[e]azulene (hydrogen chloride salt) was obtained as a yellow syrup in 12% yield: $^1$H NMR (free base) δ 7.67 (dd, 1H, J=2.7, 10.8 Hz), 7.06 (dd, 1H, J=6.0, 8.3 Hz), 6.83 (td, 1H, J=2.7, 8.3 Hz), 5.39 (b, 1H), 4.57 (t, 1H, J=6.1 Hz), 3.24 (m, 6H), 2.95 (q, 2H, J=6.7 Hz), 2.85 (t, 2H, J=6.9 Hz), 2.79 (m, 2H), 2.08 (m, 2H), 1.60 (m, 2H), 1.50 (m, 2H), 1.39 (m, 2H), 1.08 (t, 6H, J=7.1 Hz); 455 (ESMS, MH$^+$).

EXAMPLE 15

1-Aza-9-fluoro-4,5-dihydro-2-(5-(2-methoxy-5-methylphenyl)sulfonylamino)pentylamino-3-thia-benzo[e]azulene (hydrogen chloride salt) was obtained as a yellow syrup in 80% yield: $^1$H NMR (free base) δ 7.70 (m, 1H), 7.66 (dd, 1H, J=2.9, 10.8 Hz), 7.31 (dd, 1H, J=1.8, 8.4 Hz), 7.05 (dd, 1H, J=6.0, 8.1), 6.91 (d, 1H, J=8.4 Hz), 6.82 (td, 1H, J=2.8, 8.3 Hz), 5.26 (m, 1H), 5.10 (t, 1H, J=6.1 Hz), 3.93 (s, 3H), 3.18 (q, 2H, J=5.7 Hz), 2.85 (m, 4H), 2.78 (m, 2H), 2.33 (s, 3H), 2.09 (m, 2H), 1.58 (m, 2H), 1.48 (m, 2H), 1.34 (m, 2H); 504 (ESMS, MH$^+$).

EXAMPLE 16

1-Aza-2-(5-benzylsulfonylamino)pentylamino-9-fluoro-4,5-dihydro-3-thia-benzo[e]azulene was obtained as a yellow oil in 68% yield: $^1$H NMR δ 7.66 (dd, 1H, J=2.7, 10.8 Hz), 7.38 (m 5H), 7.06 (dd, 1H, J=6.0, 8.1 Hz), 6.84 (td, 1H, J=2.9, 8.3 Hz), 5.21 (m, 1H), 4.62 (m, 1H), 4.24 (s, 2H), 3.21 (q, 2H, J=6.2 Hz), 2.93 (q, 2H, J=6.4 Hz), 2.85 (t, 2H, J=6.9 Hz), 2.78 (m, 2H), 2.07 (m, 2H), 1.60 (m, 2H), 1.45 (m, 2H), 1.35 (m, 2H); 474 (ESMS, MH$^+$).

EXAMPLE 17

1-Aza-2-(5-(3,4-difluorophenyl)sulfonylamino)pentylamino-9-fluoro-4,5-dihydro-3-thia-benzo[e]azulene was obtained as a yellow oil in 78% yield: $^1$H NMR δ 7.73–7.61 (m, 2H), 7.56 (dd, 1H, J=2.9, 10.8 Hz), 7.34–7.25 (m, 1H), 7.06 (dd, 1H, J=2.9, 8.2 Hz), 6.82 (td, 1H, J=2.8, 8.2 Hz), 5.42 (b, 1H), 5.34 (b, 1H), 3.19 (m, 2H), 2.92 (m, 2H), 2.86 (t, 2H, J=7.0 Hz), 2.78 (m, 2H), 2.07 (m, 2H), 1.58 (m, 2H), 1.43 (m, 2H), 1.36 (m, 2H); 496 (ESMS, MH$^+$). The hydrogen chloride salt was obtained as a tan solid: m.p. 68–70° C.

EXAMPLE 18

1-Aza-9-fluoro-4,5-dihydro-2-(5-(4-methoxyphenyl)sulfonylamino)pentylamino-3-thia-benzo[e]azulene was obtained as a yellow oil in 73% yield: $^1$H NMR δ 7.79 (d, 2H, J=9.0 Hz), 7.62 (dd, 1H, J=2.9, 10.8 Hz), 7.06 (dd, 1H, J=6.0, 8.4 Hz), 6.97 (d, 2H, J=8.7 Hz), 6.82 (td, 1H, J=2.8, 8.3 Hz), 5.22 (m, 1H), 4.92 (m, 1H), 3.85 (s, 3H), 3.19 (q, 2H, J=5.7 Hz), 2.91 (m, 2H), 2.86 (t, 2H, J=6.9 Hz), 2.78 (m, 2H), 2.07 (m, 2H), 1.57 (p, 2H, J=7.2 Hz), 1.45 (m, 2H), 1.36 (m, 2H); 490 (ESMS, MH$^+$).

EXAMPLE 19

1-Aza-9-fluoro-4,5-dihydro-2-(5-(2-thienyl)sulfonylamino)-pentylamino-3-thia-benzo[e]azulene was obtained as a light yellow solid in 70% yield: m.p. 152–154° C.; $^1$H NMR δ 7.64–7.56 (m, 3H), 7.08 (m, 2H), 6.82 (td, 1H, J=2.8, 8.2 Hz), 5.25 (b, 1H), 5.16 (b, 1H), 3.20 (m, 2H), 3.01 (m, 2H), 2.86 (t, 2H, J=6.9 Hz), 2.77 (m, 2H), 2.07 (m, 2H), 1.58 (p, 2H, J=7.2 Hz), 1.47 (m, 2H), 1.36 (m, 2H); 466 (ESMS, MH$^+$).

EXAMPLE 20

1-Aza-9-fluoro-2-(5-(2-trifluoroethyl)sulfonylamino)pentylamino-4,5-dihydro-3-thia-benzo[e]azulene was obtained as a yellow oil in 25% yield: $^1$H NMR δ 7.65 (dd, 1H, J=2.9, 10.8 Hz), 7.07 (dd, 1H, J=5.9, 8.4 Hz), 6.84 (td, 1H, J=2.9, 8.3 Hz), 5.30 (b, 2H), 3.77 (q, 2H, J=9.1 Hz), 3.25 (t, 2H, J=6.6 Hz), 3.14 (t, 2H, J=6.6 Hz), 2.85 (t, 2H, J=6.9 Hz), 2.77 (m, 2H), 2.08 (m, 2H), 1.72–1.52 (m, 4H), 1.42 (m, 2H); 466 (ESMS, MH$^+$).

EXAMPLE 21

1-Aza-9-fluoro-2-(5-ethylsulfonylamino)pentylamino-4,5-dihydro-3-thia-benzo[e]azulene was obtained as a yellow oil in 72% yield: $^1$H NMR δ 7.65 (dd, 1H, J=2.7, 10.8 Hz), 7.06 (dd, 1H, J=6.0, 8.2 Hz), 6.83 (td, 1H, J=3.0, 8.2 Hz), 5.52 (m, 1H), 5.07 (m, 1H), 3.22 (m, 2H), 3.05 (m, 4H), 2.85 (t, 2H, J=7.0 Hz), 2.77 (m, 2H), 2.05 (m, 2H), 1.60 (m, 2H), 1.51 (m, 2H), 1.38 (m, 5H); 412 (ESMS, MH$^+$).

EXAMPLE 22

1-Aza-2-(4-diethylaminosulfonylamino)butylamino-9-fluoro-4,5-dihydro-3-thia-benzo[e]azulene was obtained as a yellow oil in 36% yield: $^1$H NMR δ 7.68 (dd, 1H, J=2.7, 10.8 Hz), 7.06 (dd, 1H, J=6.0, 8.3 Hz), 6.84 (td, 1H, J=2.4, 8.2 Hz), 5.18 (m, 1H), 4.36 (t, 1H, J=6.3 Hz), 3.26 (m, 6H), 3.01 (q, 2H, J=6.5 Hz), 2.86 (t, 2H, J=6.9 Hz), 2.08 (m, 2H), 1.67 (m, 4H), 1.18 (t, 6H, J=7.1 Hz).

EXAMPLE 23

1-Aza-9-fluoro-4,5-dihydro-2-(5-(1-methylimidazol-4-yl)sulfonylamino)pentylamino-3-thia-benzo[e]azulene was obtained as a yellow solid in 74% yield: m.p. 50–53° C.; $^1$H NMR δ 7.66 (dd, 1H, J=2.7, 10.8 Hz), 7.53 (s, 1H), 7.46 (s, 1H), 7.05 (dd, 1H, J=6.0, 8.2 Hz), 6.82 (td, 1H, J=2.7, 8.2 Hz), 5.96 (m, 1H), 5.47 (m, 1H), 3.71 (s, 3H), 3.18 (m, 2H), 2.96 (m, 2H), 2.85 (t, 2H, J=6.9 Hz), 2.06 (m, 2H), 1.56 (m, 2H), 1.48 (m, 2H), 1.37 (m, 2H).

EXAMPLE 24

1-Aza-9-fluoro-4,5-dihydro-2-(5-(3,5-dimethylisoxazol-4-yl)sulfonylamino)pentylamino-3-thia-benzo[e]azulene was obtained as a yellow oil in 80% yield: $^1$H NMR δ 7.63 (dd, 1H, J=2.7, 10.8 Hz), 7.06 (dd, 6.0, 8.3 Hz), 6.83 (dd, 1H, J=2.8, 8.2 Hz), 5.24 (b, 2H), 3.48 (m, 2H), 2.94 (m, 2H), 2.85 (t, 2H, J=7.0 Hz), 2.77 (m, 2H), 2.63 (s, 3H), 2.40 (s, 3H), 2.08 (m, 2H), 1.60 (p, 2H, J=7.5 Hz), 1.49 (m, 2H), 1.38 (m, 2H).

EXAMPLE 25

1-Aza-9-fluoro-4,5-dihydro-2-(5-aminosulfonylamino)pentylamino-3-thia-benzo[e]azulene was obtained as a yellow oil in 39% yield: $^1$H NMR δ 7.58 (dd, 1H, J=2.7, 10.8 Hz), 7.06 (dd, 1H, J=6.0, 8.3 Hz), 6.82 (td, 1H, J=2.7, 8.2 Hz), 5.30 (b, 2H), 5.18 (b, 2H), 3.19 (t, 2H, J=6.4 Hz), 3.09 (m, 2H), 2.82 (t, 2H, J=5.4 Hz), 2.76 (m, 2H), 2.07 (m, 2H), 1.85–1.47 (m, 4H), 1.43 (m, 2H).

EXAMPLE 26 trans-1-aza-9-fluoro-2-(4-(2-fluorophenyl)sulfonylamino-methyl)cyclohexylamino-4,5-dihydro-3-thia-benzo[e]-azulene: $^1$H NMR δ 7.89 (apparent td, 1H, J=1.4, 7.5 Hz), 7.62 (dd, 1H, J=2.7, 10.8 Hz), 7.59 (m, 1H), 7.25–7.19 (m, 2H), 7.04 (dd, 1H, J=6.0, 8.1 Hz), 6.81 (td, 1H, J=3.0, 8.2 Hz), 5.08 (broad m, 1H), 4.95 (m, 1H), 3.02 (m, 1H), 2.90–2.75 (m, 6H), 2.25–0.80 (m, 10H).

EXAMPLE 27 trans-1-Aza-9-fluoro-4,5-dihydro-2-{4-(4-methoxyphenyl)-sulfonylaminomethyl}cyclohexylamino-3-thia-benzo[e]azulene: 6.2% yield; $^1$H NMR (CDCl$_3$) δ 7.79 (d, 2H, J=8.7 Hz), 7.62 (dd, 1H, J=10.8, 2.7 Hz), 7.05 (dd, 1H, J=6.0, 8.3 Hz), 6.98 (d, 2H, J=8.7 Hz), 6.82 (apparent dt, 1H, J=2.8, 8.2 Hz), 4.95 (d, 1H, J=8 Hz), 4.66 (t, 1H, J=5.1 Hz), 3.85 (s, 3H), 3.24 (b, 1H), 2.90–0.80 (m, 17H).

EXAMPLE 28 trans-N2-(4-(2,6-Difluorophenylsulfonyl)aminomethyl)cyclohexyl-9-fluoro-5,6-dihydro-4H-benzo[6,7]cyclohepta-[d][1,3]-thiazol-2-amine: A solution of trans-N2-(4-aminomethyl)cyclohexyl-9-fluoro-5,6-dihydro-4H-benzo[6,7]-cyclohepta[d][1,3]thiazol-2-amine hydrochloride (200 mg, 0.52 mmol) and N,N-diisopropylethylamine (0.22 ml, 1.29 mmol) in dry THF (8 ml) was treated with 2,6-difluorobenzenesulfonyl chloride (117 mg, 0.55 mmol) in THF (2 ml). The mixture was stirred at room temperature overnight. The solvent was evaporated. The residue was dissolved in dichloromethane. The solution was then washed with 5% HCl solution, dried (MgSO$_4$), filtered and concentrated. The product was purified by preparative TLC (EtOAc/hexane 1:1) to give a tan solid (53% yield): $^1$H NMR (CDCl$_3$) δ 1.10 (4H, m), 1.42 (1H, m), 1.80 (2H, m), 2.10 (2H, m), 2.20 (2H, m), 2.80 (2H, m), 2.84 (2H, t, J=6.9 Hz), 2.92 (2H, m), 3.23 (1H, m), 5.05 (1H, broad), 5.55 (1H, broad), 6.80 (1H, m), 7.05 (3H, m), 7.50 (1H, m), 7.65 (1H, m).

Similarly prepared were:

EXAMPLE 29 trans-1-Aza-2-{4-benzylsulfonylaminomethyl}cyclohexylamino-9-fluoro-4,5-dihydro-3-thia-benzo[e]azulene: 23.6% yield; $^1$H NMR (CDCl$_3$) δ 7.62 (dd, 1H, J=10.8, 2.7 Hz), 7.50–7.20 (m, 5H), 7.05 (dd, 1H, J=6.0, 8.3 Hz), 6.81 (apparent dt, 1H, J=2.8, 8.2 Hz), 4.95 (m, 1H), 4.30 (m, 1H), 4.24 (m, 2H), 4.10 (m, 2H), 3.25 (broad, 1H), 2.90–0.80 (m, 15H).

EXAMPLE 30 trans-N2-(4-(2-Thienylsulfonyl)aminomethyl)cyclohexyl-9-fluoro-5,6-dihydro-4H-benzo[6,7]cyclohepta[d][1,3]thiazol-2-amine: $^1$H NMR (CDCl$_3$) δ 1.15 (4H, m), 1.45 (1H, m), 1.80 (2H, m), 2.07 (2H, m), 2.20 (2H, m), 2.82 (6H, m), 3.25 (1H, m), 5.00 (2H, m), 6.82 (1H, m), 7.05 (1H, m), 7.10 (1H, t, J=4.4 Hz), 7.62 (3H, m).

EXAMPLE 31 trans-N2-(4-Ethylsulfonylaminomethyl)cyclohexyl-9-fluoro-5,6-dihydro-4H-benzo[6,7]cyclohepta[d][1,3]thiazol-2-amine: $^1$H NMR (CDCl$_3$) δ 1.15 (4H, m), 1.38 (3H, t, J=7.4 Hz), 1.45 (1H, m), 1.90 (2H, m), 2.10 (2H, m), 2.25 (2H, m), 2.80 (2H, m), 2.86 (2H, t, J=6.9 Hz), 2.97 (2H, t, J=6.6 Hz), 3.05 (2H, q, J=7.4 Hz), 3.30 (1H, broad), 4.50 (1H, m), 4.97 (1H, m), 6.83 (1H, m), 7.07 (1H, m), 7.66 (1H, m).

EXAMPLE 32 trans-1-Aza-9-fluoro-4,5-dihydro-2-{4-(1-methylimidazolyl-4-yl)sulfonylaminomethyl}cyclohexylamino-3-thia-benzo[e]azulene in 33% yield: $^1$H NMR (CDCl$_3$) δ 7.67 (dd, 1H, J=10.8, 3.0 Hz), 7.52 (s, 1H), 7.48 (s, 1H), 7.05 (dd, 1H, J=6.0, 8.2 Hz), 6.82 (apparent dt, 1H, J=2.8, 8.3 Hz), 5.43 (broad, 1H), 5.01 (d, 1H, J=8.0 Hz), 3.76 (s, 3H), 3.22 (m, 1H), 2.90–2.70 (m, 5H), 2.30–0.80 (m, 9H).

EXAMPLE 33 trans-1-Aza-9-fluoro-4,5-dihydro-2-{4-(3,5-dimethylisoxazol-4-yl)sulfonylaminomethyl}cyclohexylamino-3-thia-benzo[e]azulene in 87% yield: $^1$H NMR (CDCl$_3$) δ 7.55 (dd, 1H, J=10.8, 3.0 Hz), 7.05 (dd, 1H, J=6.0, 8.2 Hz), 6.81 (apparent dt, 1H, J=2.8, 1.3 Hz), 5.95 (broad, 1H), 5.30 (broad, 1H), 3.20–2.70 (m, 5H), 2.61 (s, 3H), 2.38 (s, 3H), 2.20–0.80 (m, 9H).

EXAMPLE 34 trans-1-Aza-9-fluoro-4,5-dihydro-2-(4-methylsulfonylamino)-cyclohexylamino-3-thia-benzo[e]azulene was obtained as a white solid in 41% yield: m.p. 179–181° C.; $^1$H NMR δ 7.67 (dd, 1H, J=2.8, 10.8 Hz), 7.07 (dd, 1H, J=6.0, 8.2 Hz), 6.84 (td, 1H, J=2.8, 8.2 Hz), 4.96 (b, 1H), 4.52 (b, 1H), 3.32 (b, 2H), 3.00 (s, 3H), 2.86 (t, 2H, J=6.9 Hz), 2.79 (m, 2H), 2.26 (m, 2H), 2.17 (m, 4H), 1.35 (m, 4H); 410 (ESMS, MH$^+$).

EXAMPLE 35 trans-1-Aza-9-fluoro-4,5-dihydro-2-(4-diethylaminosulfonylamino)cyclohexylamino-3-thia-benzo[e]azulene was obtained as a tan solid in 13% yield: m.p. 172–174° C.; $^1$H NMR δ 7.68 (dd, 1H, J=2.8, 10.8 Hz), 7.06 (dd, 1H, J=5.8, 8.3 Hz), 6.84 (td, 1H, J=2.7, 8.2 Hz), 4.82 (m, 1H), 3.96 (d, 1H, J=7.5 Hz), 3.38 (m, 1H), 3.27 (q, 4H, J=7.1 Hz), 3.17 (m, 1H), 2.86 (t, 2H, J=6.9 Hz), 2.80 (m, 2H), 2.27–2.03 (m, 6H), 1.32 (m, 2H), 1.20 (t, 6H, J=7.1 Hz); 467 (ESMS, MH$^+$).

EXAMPLE 36 trans-1-Aza-9-fluoro-4,5-dihydro-2-(4-(4-methoxyphenyl)sulfonylamino)cyclohexylamino-3-thia-benzo[e]azulene was obtained as a yellow syrup in 50% yield: $^1$H NMR δ 7.82 (d, 2H, J=8.9 Hz), 7.65 (dd, 1H, J=2.8, 10.8 Hz), 7.05 (dd, 1H, J=6.0, 8.2 Hz), 6.98 (d, 2H, J=8.9 Hz), 6.82 (td, 1H, J=2.9, 8.3 Hz), 4.83 (d, 1H, J=7.7 Hz), 4.55 (d, 1H, J=7.5 Hz), 3.88 (s, 3H), 3.27 (m, 1H), 3.10 (m, 1H), 2.84 (t, 2H, J=6.9 Hz), 2.78 (m, 2H), 2.16–2.02 (m, 4H), 1.89 (m, 2H), 1.24 (m, 4H); 502 (ESMS, MH$^+$).

EXAMPLE 37 trans-1-Aza-9-fluoro-4,5-dihydro-2-(4-(2-thienyl)sulfonyl-amino)cyclohexylamino-3-thia-benzo[e]azulene was obtained as a tan solid in 36% yield: m.p. 230–231° C.; $^1$H NMR δ 7.67–7.58 (m, 3H), 7.10–7.03 (m, 2H), 6.81 (td, 1H, J=2.8, 8.3 Hz), 4.87 (m, 1H), 4.79 (m, 1H), 3.26 (m, 2H), 2.84 (t, 2H, J=6.9 Hz), 2.77 (m, 2H), 2.18–2.02 (m, 4H), 1.93 (m, 2H), 1.28 (m, 4H); 478 (ESMS, MH$^+$).

EXAMPLE 38 trans-1-Aza-9-fluoro-4,5-dihydro-2-(4-(2,2,2-trifluoroethyl)sulfonylamino)cyclohexylamino-3-thia-benzo[e]azulene was obtained as a yellow solid in 32% yield: m.p. 89–91° C.; $^1$H NMR δ 7.68 (dd, 1H, J=2.7, 10.8 Hz), 7.07 (dd, 1H, J=6.0, 8.2 Hz), 6.84 (td, 1H, J=2.8, 8.3 Hz); 4.78 (m, 1H), 4.72 (m, 1H), 3.82 (q, 2H, J=8.9 Hz), 3.38 (m, 2H), 2.89–2.81 (m, 4H), 2.28 (m, 2H), 2.10 (m, 4H), 1.47–1.30 (m, 4H); 478 (ESMS, MH$^+$).

EXAMPLE 39

1-Aza-9-fluoro-4,5-dihydro-2-(4-(2,2,2-trifluoroethyl)-sulfonylamino)butylamino-3-thia-benzo[e]azulene (TFA salt) was obtained as a white solid in 35% yield: m.p. 140–141° C.; 452 (ESMS, MH$^+$).

EXAMPLE 40 trans-1-Aza-9-fluoro-2-{4-(3,4-difluorophenyl)sulfonyl-aminomethy}cyclohexylamino-4,5-dihydro-3-thia-benzo[e]azulene: 522 (ESMS, MH$^+$); $^1$H NMR (CDCl$_3$) δ 7.74–7.63 (m, 2H), 7.60 (dd, 1H, J=2.7, 10.8 Hz), 7.32 (apparent dq, 1H, J=7.6, 1.0), 7.06 (dd, 1H, J=6.0, 8.3 Hz), 6.82 (apparent dt, 1H, J=2.8, 8.2 Hz), 5.05–4.95 (m, 2H), 3.25 (m, 1H), 2.95–2.60 (m, 6H), 2.05 (m, 2H), 2.01 (ABm, 4H), 1.62 (broad, 1H), 1.41 (m, 1H), 1.30–0.80 (m, 4H).

EXAMPLE 41 trans-1-Aza-9-fluoro-2-{4-trifluoromethylsulfonylaminomethyl}cyclohexylamino-4,5-dihydro-3-thiabenzo[e]-azulene in 17% yield: 446 (ESMS, MH$^+$); $^1$H NMR (CDCl$_3$) δ 7.69 (dd, 1H, J=2.7, 10.8 Hz), 7.05 (dd, 1H, J=6.0, 8.3 Hz), 6.82 (apparent dt, 1H, J=2.8, 8.2 Hz), 4.87 (d, 1H, J=8.0 Hz), 4.61 (m, 1H), 3.29 (m, 1H), 3.00 (t, 2H, J=9.2 Hz), 2.86 (t, 2H, J=6.9 Hz), 2.83–2.77 (m, 2H), 2.06 (m, 2H), 2.01 (ABm, 4H), 1.80–1.00 (m, 6H).

EXAMPLE 42 trans-1-Aza-9-fluoro-2-{4-(2-fluoro)phenylsulfonylamino}-cyclohexylmethylamino-4,5-dihydro-3-thia-benzo[e]azulene in 100% yield: 504 (ESMS, MH$^+$); $^1$H NMR (CDCl$_3$) δ 7.90 (apparent dt, 1H, J=1.1 average, 7.7 Hz), 7.63 (dd, 1H, J=2.8, 10.7 Hz), 7.57 (apparent dq, 1H, J=1.1, 3.5 Hz), 7.56–7.17 (m, 2H), 7.04 (dd, 1H, J=6.0, 8.3 Hz), 6.82 (apparent dt, 1H, J=2.8, 8.3 Hz), 5.46 (broad, 1H), 4.94 (d, 1H, J=5.7 Hz), 3.15 (m, 1H), 3.05 (m, 2H), 2.83 (t, 2H, J=6.9 Hz), 2.05–0.75 (m, 12H).

EXAMPLE 43 trans-N2-(4-Methylsulfonylamino)cyclohexylmethyl-9-fluoro-5,6-dihydro-4H-benzo[6,7]cyclohepta[d][1,3]thiazol-2-amine: A mixture of trans-N2-(4-amino)cyclohexylmethyl-9-fluoro-5,6-dihydro-4H-benzo[6,7]cyclohepta[d][1,3]thiazol-2-amine dihydrochloride (418 mg, 1.0 mmol) and triethylamine (1.25 mL) in THF (6 ml) was cooled in an ice water bath and treated with methanesulfonyl chloride dropwise (0.10 ml). The mixture was stirred at room temperature for 30 minutes and then poured into water (60 ml). The product was extracted into chloroform and purified by flash chromatography over silica gel (EtOAc/hexane 1:1) to afford a yellow solid (227 mg, 54% yield): CIMS m/e=424 (MH$^+$); $^1$H NMR (300 MHz, CDCl$_3$) δ 1.0–1.3 (4H, m), 1.4–1.6 (1H, m), 1.84 (2H, d, J=12.3 Hz), 2.0–2.2 (4H, m), 2.77 (2H, t, J=5.4 Hz), 2.84 (2H, t, J=6.9 Hz), 2.97 (3H, s), 3.07 (2H, t, J=6.1 Hz), 3.1–3.30 (1H, m), 4.66 (1H, d, J=7.6 Hz), 5.52 (1H, t, J=4.5 Hz), 6.83 (1H, dt, J=2.8, 8.2 Hz), 7.06 (1H, dd, J=5.9, 8.2 Hz), 7.65 (1H, dd, J=2.7, 10.7 Hz).

EXAMPLE 44 trans-N2-(4-Aminosulfonylamino)cyclohexylmethyl-9-fluoro-5,6-dihydro-4H-benzo[6,7]cyclohepta[d][1,3]thiazol-2-amine a. trans-1-Aminomethyl-4-(benzyloxycarbonylamino)cyclohexane: To a solution of trans-1-(t-butyloxycarbonylaminomethyl)-4-(benzyloxycarbonylamino)-cyclohexane (20 g, 55.2 mmol) in EtOAc (790 mL) was added 4N HCl in dioxane (200 mL). The mixture was stirred overnight and then concentrated to give a white solid: $^1$H NMR (300 MHz, CD$_3$OD) δ 1.0–1.3 (4H, m), 1.50–1.67 (1H, m), 1.83 (2H, d, J=12.3 Hz), 1.96 (2H, d, J=10.3 Hz), 2.77 (2H, d, J=7.0 Hz), 3.20–3.40 (1H, m), 5.03 (1H, s), 7.20–7.40 (5H, m).

b. trans-1-Aminocarbothioylaminomethyl-4-(benzyloxycarbonylamino)cyclohexane: trans-1-Aminomethyl-4-(benzyl-oxycarbonylamino) cyclohexane (55.2 mmol) was dissolved in a mixture of chloroform (350 ml) and triethylamine (16 mL), cooled in an ice water bath and treated with benzoylisothiocyanate (10 ml, 74.4 mmol). The mixture was stirred for 6 hours before it was allowed to slowly warm to room temperature overnight. The solvent was evaporated and the residue triturated with MeOH (800 ml) and potassium carbonate (70 g) solution in water (800 ml). The mixture was heated at reflux for 10 min. and then additional aqueous potassium carbonate solution (34 g/140 ml) was added. The mixture was cooled to 8° C. The resulting precipitate was collected by filtration and washed with water and ether (200 mL) to give the desired product as a white solid (12.02 g, 68%): m.p. 155–158° C.; $^1$H NMR (300 MHz, CD$_3$OD) δ 0.9–1.3 (4H, m), 1.4–1.55 (1H, m), 1.79 (2H, d, J=9.5 Hz), 1.92 (2H, d, J=10.0 Hz), 2.95 (1H, d, J=6.0 Hz), 3.20–3.40 (2H, m), 5.03 (2H, s), 7.20–7.40 (5H, m).

c. trans-N2-(4-Benzyloxycarbonylamino)cyclohexylmethyl-9-fluoro-5,6-dihydro-4H-benzo[6,7]cyclohepta[d][1,3]thiazol-2-amine: A mixture of trans-1-aminocarbothioylaminomethyl-4-(benzyloxycarbonylamino)cyclohexane (4.46 g, 13.9 mmol), 2-bromo-8-fluoro-1-benzosuberone (4.08 g, 15.9 mmol), and N,N-diisopropylethylamine (4.6 mL) in ethanol (95 ml) was heated at reflux for 6 hours The solvent was evaporated and the residue washed with water (200 ml). Ether (10 ml) was then added and the suspension filtered. The solid was washed with ether (10 ml) to give a white solid (5.55 g, 83%): CIMS m/e=480 (MH$^+$); $^1$H NMR (300 MHz, CDCl$_3$) δ 1.0–1.2 (4H, m), 1.40–1.55 (1H, m), 1.89 (2H, d, J=7.7 Hz), 2.00–2.16 (4H, m), 2.77 (2H, t, J=5.4 Hz), 2.86 (2H, t, J=6.9 Hz), 3.13 (2H, t, J=6.4 Hz), 3.4–3.6 (1H, m), 4.30 (1H, d, J=6 Hz), 5.05 (1H, m), 5.09 (2H, s), 6.8 (1H, dt, J=2.8, 8.4 Hz), 7.06 (1H, dd, J=5.7, 8.4 Hz), 7.35 (5H, m), 7.69 (1H, dd, J=2.8, 10.8 Hz).

d. trans-N2-(4-Amino)cyclohexylmethyl-9-fluoro-5,6-dihydro-4H-benzo[6,7]cyclohepta[d][1,3]thiazol-2-amine: trans-N2-(4-Benzyloxycarbonylamino)cyclohexylmethyl-9-fluoro-5,6-dihydro-4H-benzo[6,7]cyclohepta[d][1,3]thiazol-2-amine (5.55 g) was heated at reflux in a mixture of trifluoroacetic acid (50 ml) and water (5 ml) for 30 min. Most of the solvent was evaporated and the residue poured into water (150 ml). Potassium carbonate was added until the pH reached 10. The product was extracted into chloroform and converted to the hydrochloride salt which was isolated as an off-white solid: $^1$H NMR of the free base (300 MHz, CDCl$_3$) δ 1.1–1.6 (4H, m), 1.3–1.7 (4H, m), 1.80–2.00 (4H, m), 2.00–2.20 (2H, m), 2.30 (1H, m), 2.79 (2H, t, J=5.5 Hz), 2.86 (2H, 5, J=6.9 Hz), 3.12 (2H, t, J=6.2 Hz), 5.07 (1H, t), 6.82 (1H, dt, J=2.8 Hz), 7.05 (1H, dd, J=5.9, 8.3 Hz), 7.70 (1H, dd, J=2.8, 10.8 Hz).

e. trans-N2-(4-Aminosulfonylamino)cyclohexylmethyl-9-fluoro-5,6-dihydro-4H-benzo[6,7]cyclohepta[d][1,3]thiazol-2-amine: A mixture of trans-N2-(4-amino)cyclohexylmethyl-9-fluoro-5,6-dihydro-4H-benzo[6,7]cyclohepta[d][1,3]-thiazol-2-amine dihydrochloride (524 mg, 1.25 mmol), sulfamide (371 mg) and triethylamine (1 mL) in THF (7 ml), methanol (5 mL) and water (7 ml) was heated at reflux for 18 hours. Most of the solvent was evaporated and then water (50 ml) was added. The product was extracted into chloroform and then purified by flash chromatography over silica gel (EtOAc/hexane 5:4) to give the desired product as a yellow solid (238 mg, 56%): m.p. 180–182° C.; CIMS m/e=425 (MH$^+$); $^1$H NMR (300 MHz, CDCl$_3$) δ 1.00–1.30 (4H, m), 1.40–1.60 (1H, m), 1.81 (2H, d, J=12.0 Hz), 2.00–2.20 (4H, m), 2.75 (2H, t, J=5.3 Hz), 2.82 (2H, t, J=6.9 Hz), 3.02 (2H, d, J=6.4 Hz), 3.20 (1H, m), 4.85 (1H, d, J=6.7 Hz), 5.20 (2H, s), 5.85 (1H, s), 6.83 (1H, dt, J=2.8, 8.2 Hz), 7.05 (1H, dd, J=5.9, 8.3 Hz), 7.58 (1H, dd, J=2.8, 10.7 Hz).

EXAMPLE 45

9-Fluoro-5,6-dihydro-4H-benzo[6,7]cyclohepta[d][1,3]thiazol-2-amine: 6-Bromo-3-fluoro-6,7,8,9-tetrahydro-5H-benzo[a]cyclohepten-5-one (1.0 g, 3.89 mmole) was mixed with thiourea (355 mg, 4.66 mmole) in 20 ml of ethanol and heated at reflux temperature for 16 hours. The reaction mixture was cooled and filtered to give a solid (m.p. 270° C.). The filtrate was concentrated and then partitioned between ethyl acetate and saturated sodium carbonate solution. The organic extract was concentrated and chromatographed (silica, ethyl acetate/hexanes) to give the desired product as a yellow solid (m.p. 142–144° C., 34%).

N1-(9-Fluoro-5,6-dihydro-4H-benzo[6,7]cyclohepta[d][1,3]thiazol-2-yl)-5-bromopentanamide:

9-Fluoro-5,6-dihydro-4H-benzo[6,7]cyclohepta[d][1,3]thiazol-2-amine (150 mg, 0.640 mmole) was dissolved in 3 ml of dry THF, mixed with triethylamine (135 μl, 0.970 mmole), cooled in an ice bath and treated with 5-bromovaleryl chloride (90 μl, 0.67 mmole). The mixture was stirred at room temperature for 3 days. TLC analysis of the mixture showed 50% completion. Hence, a catalytic amount of DMAP was added and stirring was continued for 16 hours. There was no change in the TLC of the mixture. 5-Bromovaleryl chloride (90 μl) was added and stirred for 3 days. The reaction mixture was partitioned between ethyl acetate and saturated sodium carbonate and the aqueous phase separated and extracted with 2×3 ml ethyl acetate. The combined ethyl acetate extracts were washed with saturated sodium chloride solution, concentrated and chromatographed (silica, Ethyl acetate/hexanes) to give 179 mg of the desired product as a white foam (70%): 397, 399 (ESMS, MH+).

1-5-[(9-Fluoro-5,6-dihydro-4H-benzo[6,7]cyclohepta[d][1,3]-thiazol-2-yl)amino]-5-oxopentyl-1,2-triazadien-2-ium:

N1-(9-Fluoro-5,6-dihydro-4H-benzo[6,7]cyclohepta[d][1,3]thiazol-2-yl)-5-bromopentanamide (179 mg, 0.45 mmole) was dissolved in 1.5 ml of dry DMSO and treated with 72 mg of ammonium chloride (1.35 mmole) and 59 mg of sodium azide (0.91 mmole). After 5 hours, the mixture was heated at 60° C. for 16 hours. The reaction mixture was cooled, quenched with ice-water, extracted with ethyl acetate (3×3 ml), and the combined ethyl acetate extracts washed with water, and concentrated to give 145 mg of a yellow solid (90%): 360 (ESMS, MH$^+$).

N1-(9-fluoro-5,6-dihydro-4H-benzo[6,7]cyclohepta[d][1,3]thiazol-2-yl)-5-aminopentanamide:

3907-50-2 1-5-[(9-Fluoro-5,6-dihydro-4H-benzo[6,7]cyclohepta[d][1,3]thiazol-2-yl)amino]-5-oxopentyl-1,2-triazadien-2-ium (145 mg, 0.40 mmole) was dissolved in 2 ml of THF and treated with P(CH$_3$)$_3$ in THF (1M, 0.80 ml, 0.8 mmol) and water (22 μL, 1.22 mmole). The resulting mixture was stirred at room temperature for 16 hours and the solvent evaporated. The residue was dissolved in ethyl acetate and chromatographed over silica gel (14 g) eluting with ethyl acetate and then with EtOAc/7M NH$_3$ in MeOH (20:3) to give an oil (115 mg).

N1-(9-fluoro-5,6-dihydro-4H-benzo[6,7]cyclohepta[d][1,3]thiazol-2-yl)-5-[(methylsulfonyl)amino]pentanamide:

N1-(9-fluoro-5,6-dihydro-4H-benzo[6,7]cyclohepta[d][1,3]thiazol-2-yl)-5-aminopentanamide (115 mg, 0.34 mmole) was dissolved in 2 ml of dry THF, cooled with an ice bath, triethylamine was added (96 μl, 0.69 mmole) followed by addition of 27 μl of methane sulfonyl chloride (0.35 mmole). The reaction mixture was stirred at room temperature for 6 hours, quenched with saturated sodium carbonate solution and extracted with 3×3 ml of ethyl acetate. The combined ethyl acetate extracts were washed with saturated sodium chloride solution, concentrated and chromatographed (12 g of silica gel, EtOAc/hexanes/7N NH$_3$ in MeOH, 50:50:2) to give 53 mg of the desired product as a white solid (38%): m.p. 145–147° C.; 412 (ESMS, MH$^+$).

EXAMPLE 46 trans-N2-(4-Aminosulfonylaminomethyl)cyclohexyl-4,5-dihydro-benzo[2,3]oxepino[4,5-d][1,3]thiazol-2-amine a. 2,3,4,5-Tetrahydro-1-benzoxepin-5-one To a solution of P$_2$O$_5$ (62 g) in methanesulfonic acid (415 ml) was added a solution of 4-phenoxybutyric acid (16 g) in methanesulfonic acid (120 ml) in 4 portions every 2 hours. After the last addition, the mixture was allowed to stand for another 2 hours before it was poured onto ice (3 Kg). The mixture was neutralized with 50% NaOH solution and the product extracted into chloroform. Purification by flash chromatography over silica gel (EtOAc/hexane 1:10) afforded an oil (5.06 g, 35%): $^1$H NMR (300 MHz, CDCl$_3$) δ 2.22 (2H, m), 2.91 (2H, t, J=7.0 Hz), 4.25 (2H, t, J=6.6 Hz), 7.10 (2H, m), 7.43 (1H, dt, J=1.8, 7.5 Hz), 7.77 (1H, dd, J=1.6, 7.7 Hz).

b. 4-Bromo-2,3,4,5-tetrahydro-1-benzoxepin-5-one: To a solution of 2,3,4,5-tetrahydro-1-benzoxepin-5-one (5.06 g, 31.2 mmol) in acetic acid (50 ml) cooled by an ice water bath was added bromine (1.75 ml) dropwise. The solvent was evaporated to give the product as a brown oil: $^1$H NMR (300 MHz, CDCl$_3$) δ 2.40–2.60 (1H, m), 2.90–3.00 (1H, m), 4.08–4.18 (1H, m), 4.42–4.49 (1H, m), 4.99 (1H, dd, J=8.1, 7.0 Hz), 7.07 (1H, d, J=8.3 Hz), 7.12 (1H, t, J=7.5 Hz), 7.45 (1H, dt, J=1.6, 7.7 Hz), 7.75 (1H, dd, J=1.7, 7.8 Hz).

c. trans-N2-(4-(t-Butyloxycarbonylaminomethyl)cyclohexyl-4,5-dihydro-benzo[2,3]oxepino[4,5-d][1,3]thiazol-2-amine: A mixture of 4-bromo-2,3,4,5-tetrahydro-1-benzoxepin-5-one (7.6 mmol), trans-1-(aminocarbothioylamino)-4-(t-butyloxycarbonylaminomethyl)cyclohexane (6.9 mmol) and N,N-diisopropylethylamine (2.5 mL) in ethanol (48 ml) was heated at reflux for 6 hours. The solvent was evaporated and the residue flash chromatographed over silica gel (EtOAc/hexane 1:3) to give a yellow solid (1.97 g, 66%): $^1$H NMR (300 MHz, CDCl$_3$) δ 1.00–1.15 (4H, m), 1.44 (10H, s), 1.82 (2H, d, J=11.8 Hz), 2.21 (2H, d, J=11.9 Hz), 2.99 (2H, t, J=6.4 Hz), 3.14 (2H, t, J=5.1 Hz), 3.2–3.25 (1H, m), 4.32 (2H, t, J=5.2 Hz), 4.64 (1H, t, J=4.7 Hz), 4.94 (1H, d, J=8.0 Hz), 6.98 (1H, dd, J=1.3, 7.8 Hz), 7.07 (1H, dt, J=1.4, 7.5 Hz), 7.14 (1H, dt, J=1.8, 7.5 Hz), 8.24 (1H, dd, J=1.8, 7.8 Hz).

d. trans-N2-(4-Aminomethyl)cyclohexyl-4,5-dihydrobenzo[2,3]oxepino[4,5-d][1,3]thiazol-2-amine dihydrochloride: trans-N2-(4-(t-butyloxycarbonylaminomethyl)cyclohexyl-4,5-dihydro-benzo[2,3]oxepino[4,5-d][1,3]thiazol-2-amine (1.97 g, 4.58 mmol) in EtOAc (50 mL) and 4M HCl in dioxane (12 ml) was stirred at room temperature overnight. The solvent was evaporated to give a yellow solid (1.85 g, 99%): m.p. 245° C. (dec.); $^1$H NMR (300 MHz, CD$_3$OD) δ 1.20–1.30 (2H, m), 1.45–1.60 (2H, m), 1.70 (1H, m), 1.95 (2H, d, J=9.8 Hz), 2.21 (2H, d, J=10.8 Hz), 2.83 (2H, d, J=6.9 Hz), 3.17 (2H, t, J=5.4 Hz), 3.50–3.70 (1H, m), 4.33 (2H, t, J=5.5 Hz), 7.11 (1H, d, J=8.1 Hz), 7.21 (1H, t, J=7.5 Hz), 7.36 (1H, t, J=8.1 Hz), 7.70 (1H, d, J=7.8 Hz).

e. trans-N2-(4-Aminosulfonylaminomethyl)cyclohexyl-4,5-dihydro-benzo[2,3]oxepino[4,5-d][1,3]thiazol-2-amine: A mixture of trans-N2-(4-aminomethyl)cyclohexyl-4,5-dihydro-benzo[2,3]oxepino-[4,5-d][1,3]thiazol-2-amine dihydrochloride (402 mg, 1 mmol), sulfamide (288 mg, 3 mmol) and triethylamine (0.56 ml) in ethanol (2.5 ml) and water (2.5 ml) was heated at reflux for 3 hours before it was poured into water (50 ml). The product was extracted into chloroform and then purified by flash chromatography over silica gel (EtOAc/hexane 2:1) to afford the desired product as a white solid (362 mg, 89%): m.p. 170–173° C.; CIMS m/e=409 (MH$^+$); $^1$H NMR (300 MHz, CDCl$_3$) δ 1.0–1.3 (4H, m), 1.5–1.7 (1H, m), 1.89 (2H, d, J=12.3 Hz), 2.26 (2H, d, J=11.5 Hz), 3.01 (2H, t, J=6.5 Hz), 3.15 (2H, t, J=5.2 Hz), 3.20–3.40 (1H, m), 4.33 (2H, t, J=5.1 Hz), 4.43 (1H, t, J=6.1 Hz), 4.59 (1H, s, broad), 4.92 (1H, s, broad), 6.99 (1H, d, J=7.9 Hz), 7.08 (1H, t, J=7.4 Hz), 7.16 (1H, dt, J=1.7, 7.2 Hz), 8.23 (1H, dd, J=1.7, 7.8 Hz).

EXAMPLE 47 trans-N2-(4-Methylsulfonylaminomethyl)cyclohexyl-4,5-dihydro-benzo[2,3]oxepino[4,5-d][1,3]thiazol-2-amine: A mixture of trans-N2-(4-aminomethyl)cyclohexyl-4,5-dihydro-benzo[2,3]oxepino[4,5-d][1,3]thiazol-2-amine dihydrochloride (345 mg, 0.87 mmol) and triethylamine (1.1 ml) in THF (5 ml) was cooled in an ice water bath and treated with methanesulfonyl chloride (0.087 ml). After stirring for 30 minutes at room temperature, the mixture was poured into water (50 ml) containing potassium carbonate (1 g). The product was extracted into chloroform and purified by flash chromatography (EtOAc/hexane 2:1) to give a yellow solid (308 mg, 88% yield): m.p. 67–69° C.; CIMS m/e=408 (MH$^+$); $^1$H NMR (300 MHz, CDCl$_3$) δ 0.90–1.40 (5H, m), 1.76 (2H, d, J=11.7 Hz), 2.15 (2H, d, J=10.5 Hz), 2.80–3.00 (5H, m), 3.14 (3H, m), 4.30 (2H, t, J=4.7 Hz), 5.25 (1H, t, J=4.7 Hz), 5.35 (1H, d, J=7.9 Hz), 6.98 (1H, d, J=7.8 Hz), 7.06 (1H, t, J=7.5 Hz), 7.14 (1H, t, J=7.4 Hz), 8.19 (1H, d, J=7.6 Hz).

EXAMPLE 48 trans-1-Aza-4,5-dihydro-2-{4-(2-methoxy-5-methyl)phenyl-sulfonylaminomethyl}cyclohexylamino-6-oxa-3-thia-benzo[e]azulene: 91% yield; 514 (ESMS, MH$^+$); $^1$H NMR (CDCl$_3$) δ 8.20 (dd, 1H, J=1.6, 7.8 Hz), 7.68 (d, 1H, J=2.1 Hz), 7.30 (dd, 1H, J=2.1, 8.4 Hz), 7.10 (apparent dt, 1H, J=1.1, 7.4 Hz), 7.01 (apparent dt, 1H, J=1.1, 7.5 Hz), 6.96 (d, 1H, J=7.1 Hz), 6.90 (d, 1H, J=8.5 Hz), 5.27 (t, 2H, J=3.8 Hz), 4.29 (t, 2H, 5.2 Hz), 3.90 (s, 3H), 3.18 (m, 1H), 3.11 (t, 2H, J=5.1 Hz), 2.66 (t, 2H, J=6.5 Hz), 2.31 (s, 3H), 1.95 (ABm, 4H), 1.40–0.80 (m, 8H); m.p. (HCl salt) 100–105° C. (decomp.)

EXAMPLE 49

N1-(9-Fluoro-5,6-dihydro-4H-benzo[6,7]cyclohepta[d][1,3]-thiazol-2-yl)-5-[(2-methoxy-5-methylphenyl)sulfonyl]-aminopentanamide N1-(9-fluoro-5,6-dihydro-4H-benzo[6,7]cyclohepta[d][1,3]-thiazol-2-yl)-5-aminopentanamide (42 mg, 0.13 mmole) was dissolved in 2 ml of dry THF, cooled in an ice bath, triethylamine was added (36 μl, 0.26 mmole) followed by addition of 9 mg of o-methoxy-m-toluenesulfonyl chloride (0.13 mmole). The reaction mixture was stirred at room temperature for 6 hours, quenched with saturated sodium carbonate solution and extracted with 3×3 ml of ethyl acetate. The combined ethyl acetate extracts were washed with saturated sodium chloride solution, concentrated and chromatographed (13 g of silica gel, EtOAc/hexanes/7N NH$_3$ in MeOH, 50:50:2) to give the desired product: m.p. 70–75° C.; 518 (ESMS, MH$^+$).

EXAMPLE 50 trans-N2-(4-Methylsulfonylamino)cyclohexylmethyl-4,5-dihydro-benzo[2,3]oxepino[4,5-d][1,3]thiazol-2-amine as a yellow solid: m.p. 64–67° C.; 408 (ESMS, MH$^+$); $^1$H NMR (300 MHz, CDCl$_3$) δ 1.0–1.4 (4H, m), 1.92 (2H, d, J=12.7 Hz), 2.12 (2H, d, J=11.7 Hz), 2.98 (3H, s), 3.16 (4H, m), 3.25 (1H, m), 4.12 (1H, d, J=7.5 Hz), 4.33 (2H, t, J=5.0 Hz), 5.1 (1H, broad), 7.07 (1H, d, J=7.2 Hz), 7.11 (1H, t, J=7.9 Hz), 7.16 (1H, t, J=7.0 Hz), 8.24 (1H, d, J=7.5 Hz).

EXAMPLE 51 trans-1-Aza-4,5-dihydro-2-{4-(2-methoxy-5-methylphenyl)-sulfonylamino}cyclohexylmethylamino-6-oxa-3-thia-benzo[e]azulene in 41% yield: m.p. 220–224° C.; 514 (ESMS, MH$^+$); $^1$H NMR (CDCl$_3$) δ 8.22 (dd, 1H, J=1.6, 7.8 Hz), 7.71 (d, 1H, J=2.1 Hz), 7.32 (dd, 1H, J=2.1, 8.4 Hz), 7.18 (apparent dt, 1H, J=1.1, 7.4 Hz), 7.05 (apparent dt, 1H, J=1.1, 7.5 Hz), 6.97 (d, 1H, J=7.1 Hz), 6.91 (d, 1H, J=8.5 Hz), 5.13 (t, 1H, J=6.0 Hz), 4.83 (d, 1H, J=7.2 Hz), 4.31 (t, 2H, J=5.2 Hz), 3.93 (s, 3H), 3.13 (t, 2H, J=5.2 Hz), 3.05 (t, 2H, J=6.3 Hz), 3.02 (m, 1H), 2.34 (s, 3H), 1.90–0.80 (m, 12H).

EXAMPLE 52 trans-N2-(4-Ethylsulfonylamino)cyclohexylmethyl-9-fluoro-5,6-dihydro-4H-benzo[6,7]cyclohepta[d][1,3]thiazol-2-amine as a white solid: m.p. 140–142 ° C.; CIMS m/e=424 (MH$^+$); $^1$H NMR (300 MHz, CDCl$_3$) δ 1.00–1.40 (4H, m), 1.37 (3H, t, J=7.4 Hz), 1.91 (2H, d, J=12.5 Hz), 2.00–2.20 (4H, m), 2.79 (2H, t, J=5.5 Hz), 2.86 (2H, t, J=6.9 Hz), 3.04 (2H, q, J=7.4 Hz), 3.13 (2H, t, J=6.3 Hz), 3.10–3.30 (1H, m), 4.04 (1H, d, J=7.8 Hz), 5.09 (1H, broad), 6.84 (1H, dt, J=2.8, 8.2 Hz), 7.06 (1H, dd, J=5.9, 8.3 Hz), 7.68 (1H, dd, J=2.8, 10.8 Hz).

EXAMPLE 53 trans-1-Aza-9-fluoro-4,5-dihydro-2-{4-isopropylsulfonylamino}cyclohexylmethylamino-3-thia-benzo[e]azulene in 15% yield: 452 (ESMS, MH$^+$); $^1$H NMR (CDCl$_3$) δ 7.76 (dd, 1H, J=2.7, 10.6 Hz), 7.05 (dd, 1H, J=6.0, 8.2 Hz); 6.82 (apparent dt, 1H, J=2.8, 8.3 Hz), 5.69 (m, 1H), 4.56 (d, 1H, J=8.4 Hz), 3.20–2.90 (m, 4H); 2.83 (t, 2H, J=7.0 Hz), 2.78 (m, 2H), 2.20–0.80 (m, 12H), 1.48 (d, 6H, J=7.0 Hz).

EXAMPLE 54 trans-1-Aza-9-fluoro-4,5-dihydro-2-(4-(3-pyridylsulfonylamino)cyclohexyl)amino-3-thia-benzo[e]azulene (hydrogen chloride salt) was obtained as a white solid in 65% yield: m.p. (HCl salt) 165–167° C.; $^1$H NMR (CD$_3$OD) δ 9.27 (s, 1H), 9.02 (m, 1H), 8.86 (d, 1H, J=8.0 Hz), 8.15 (m, 1H), 7.34 (m, 2H), 7.09 (td, 1H, J=2.3, 8.6 Hz), 3.58 (b, 1H), 3.27 (b, 1H), 2.76 (m, 4H), 2.21–2.07 (m, 4H), 1.92 (m, 2H), 1.47 (m, 4H); 473 (ESMS, MH$^+$).

EXAMPLE 55

1-Aza-9-fluoro-4,5-dihydro-2-(5-(3-pyridyl)sulfonylamino)pentylamino-3-thia-benzo[e]azulene (hydrogen chloride salt) was obtained as a white solid in 66% yield: m.p. (HCl salt) 84–86° C.; $^1$H NMR (free base, CD$_3$OD) δ 9.25 (broad, 1H), 9.05 (b, 1H), 8.85 (d, 1H, J=8.1 Hz), 8.18 (m, 1H), 7.36 (m, 2H), 7.09 (td, 1H, J=2.4, 8.4 Hz), 3.47 (t, 2H, J=6.9 Hz), 3.02 (t, 2H, J=6.6 Hz), 2.78 (m, 4H), 2.17 (m, 2H), 1.75 (m, 2H), 1.64–1.48 (m, 4H); 461 (ESMS, MH$^+$).

EXAMPLE 56

1-Aza-9-fluoro-4,5-dihydro-2-(4-(3-pyridyl)sulfonylamino)butylamino-3-thia-benzo[e]azulene (hydrogen chloride salt) was obtained as a light yellow solid in 56% yield: m.p. (HCl salt) 101–103° C.; $^1$H NMR (free base, CD$_3$OD) δ 9.13 (m, 1H), 8.91 (m, 1H), 8.59 (m, 1H), 7.94 (m, 1H), 7.36 (m, 2H), 7.10 (td, 1H, J=2.7, 8.4 Hz), 3.48 (t, 2H, J=6.9 Hz), 3.02 (t, 2H, J=6.5 Hz), 2.78 (m, 4H), 2.19 (m, 2H), 1.80 (m, 2H), 1.65 (m, 2H); 447 (ESMS, MH$^+$).

EXAMPLE 57

1-Aza-9-fluoro-4,5-dihydro-2-{2-(2-methylsulfonylamino)ethoxy}ethylamino-3-thia-benzo[e]azulene in 76% yield: m.p. 159–162° C.; $^1$H NMR (CDCl$_3$) δ 7.75 (dd, 1H, J=2.5, 10.7 Hz), 7.06 (dd, 1H, J=6.0, 8.1 Hz), 6.83 (apparent dt, 1H, J=2.8, 8.3 Hz), 5.42 (broad, 1H), 5.14 (b, 1H), 3.69 (t, 2H, J=4.9 Hz), 3.61 (t, 2H, J=4.8 Hz), 3.51 (broad q, 2H, J=4.3 Hz), 3.31 (q, 2H, J=4.8 Hz), 2.98 (s, 3H), 2.86 (t, 2H, J=6.9 Hz), 2.07 (m, 2H).

EXAMPLE 58

1-Aza-9-fluoro-4,5-dihydro-2-{2-[2-(2-methoxy-5-methylphenyl)sulfonylamino]ethoxy}ethylamino-3-thia-benzo[e]azulene in 87% yield: 506 (ESMS, MH$^+$); $^1$H NMR (CDCl$_3$) δ 7.73–7.68 (m, 2H), 7.34 (dd, 1H, J=2.1, 10.1 Hz), 6.94 (d, 1H, J=8.4 Hz), 6.84 (apparent dt, 1H, J=2.8, 8.2 Hz), 5.43 (t, 1H, J=6.0 Hz), 5.23 (m, 1H), 3.94 (s, 3H), 3.51–3.43 (m, 4H), 3.09 (q, 2H, J=5.5 Hz), 2.87 (t, 2H, J=6.9 Hz), 2.82–2.78 (m, 2H), 2.12–2.00 (m, 2H); m.p. (HCl salt) 56–60° C.

EXAMPLE 59 trans-1-Aza-9-fluoro-4,5-dihydro-2-(4-(3-pyridyl)sulfonylaminomethyl)cyclohexylamino-3-thia-benzo[e]azulene (hydrogen chloride salt) was obtained as a light yellow solid in 69% yield: m.p. (HCl salt) 127–129° C.; $^1$H NMR (free base, CD$_3$OD) δ 9.08 (d, 1H, J=1.9 Hz), 8.81 (d, 1H, J=4.8 Hz), 8.15 (m, 1H), 7.47 (m, 2H), 7.05 (dd, 1H, J=6.0, 8.2 Hz), 6.80 (td, 1H, J=2.7, 8.2 Hz), 5.98 (m, 1H), 5.33 (m, 1H), 3.14 (m, 1H), 2.83 (t, 2H, J=6.9 Hz), 2.76 (m, 4H), 2.10 (m, 4H), 1.73 (m, 2H), 1.23 (m, 1H), 1.10 (m, 2H), 0.95 (m, 2H); 487 (ESMS, MH$^+$).

EXAMPLE 60 trans-N2-(4-Ethylsulfonylamino)cyclohexylmethyl-8-methoxy-4,5-dihydro-benzo[2,3]oxepino[4,5-d][1,3]thiazol-2-amine as a yellow solid: m.p. 170–172° C.; 452 (ESMS, MH$^+$); $^1$H NMR δ 1.20 (4H, m), 1.37 (3H, t, J=7.4 Hz), 1.90 (2H, m), 2.10 (2H, m), 3.04 (2H, q, J=7.4 Hz), 3.13 (4H, m), 3.25 (1H, broad), 3.80 (3H, s), 3.96 (1H, d, J=7.7 Hz), 4.33 (2H, t, J=5.1 Hz), 5.02 (1H, broad), 6.55 (1H, d, J=2.5 Hz), 6.66 (1H, dd, J=2.6, 8.6 Hz), 8.15 (1H, d, J=8.8 Hz).

EXAMPLE 61 trans-1-Aza-4,5-dihydro-8-methoxy-2-{4-methylsulfonyl-amino)cyclohexylmethylamino-6-oxa-3-thia-benzo[e]azulene in 59% yield: m.p. 65–70° C.; 438 (ESMS, MH$^+$); $^1$H NMR (CDCl$_3$) δ 8.15 (d, 1H, J=8.9 Hz), 6.66 (dd, 1H, J=2.5, 8.8 Hz), 6.66 (d, 1H, J=2.5 Hz), 5.08 (b, 1H), 4.33 (t, 2H, J=5.1 Hz), 4.08 (d, 1H, J=7.3 Hz), 3.80 (s, 3H), 3.25 (m, 1H), 3.13 (q, 2H, J=5.3 Hz), 2.98 (s, 3H), 2.02–1.00 (m, 9H).

EXAMPLE 62 trans-1-Aza-9-fluoro-4,5-dihydro-2-{4-(3-pyridyl)sulfonylamino}cyclohexylmethylamino-3-thia-benzo[e]azulene in 63% yield: m.p. 158–160° C.; 487 (ESMS, MH$^+$); $^1$H NMR (CDCl$_3$) δ 9.10 (d, 1H, J=2.2 Hz), 8.81 (dd, 1H, J=1.5, 4.8 Hz), 8.18 (apparent dt, 1H, J=4.1, 1.5 Hz), 7.65 (dd, 1H, J=2.8, 10.8 Hz), 7.48 (dd, 1H, J=4.8, 5.4 Hz), 7.05 (dd, 1H, J=5.9, 8.3 Hz), 6.83 (apparent dt, 1H, J=2.8, 8.2 Hz), 5.06 (b, 1H), 4.59 (d, 1H, J=7.7 Hz), 3.19–3.00 (m, 1H), 3.10 (t, 2H, J=6.1 Hz), 2.85 (t, 2H, J=3.4 Hz), 2.80–2.76 (m, 2H), 2.10–0.80 (m, 9H).

EXAMPLE 63 trans-1-Aza-4,5-dihydro-9-methoxy-2-{4-methylsulfonyl-amino}cyclohexylmethylamino-6-oxa-3-thia-benzo[e]azulene in 54% yield: 438 (ESMS, MH$^+$); $^1$H NMR (CDCl$_3$) δ 7.80 (d, 1H, J=3.2 Hz), 6.92 (d, 1H, J=8.7 Hz), 6.72 (dd, 1H, J=3.2, 8.8 Hz), 5.04 (broad m, 1H), 4.28 (t, 2H, J=5.1 Hz), 4.12 (q, 2H, J=7.2 Hz), 4.11 (m, 1H), 3.83 (s, 3H), 3.40–3.13 (m, 5H), 2.99 (s, 3H), 2.20–1.00 (m, 9H); m.p. (HCl salt) 200–215° C.

EXAMPLE 64 trans-N2-(4-Ethylsulfonylamino)cyclohexylmethyl-9-methoxy-4,5-dihydro-benzo[2,3]oxepino[4,5-d][1,3]thiazol-2-amine as a gray solid: m.p. 165–170° C.; 452 (ESMS, MH$^+$); $^1$H NMR δ 1.1–1.3 (4H, m), 1.37 (3H, t, J=7.4 Hz), 1.92 (2H, m), 2.12 (2H, m), 3.04 (2H, q, J=7.4 Hz), 3.14 (4H, t, J=5.2 Hz), 3.25 (1H, m), 3.83 (3H, s), 3.95 (1H, d, J=8.1 Hz), 4.28 (2H, t, J=5.2 Hz), 5.07 (1H, broad), 6.72 (1H, dd, J=3.1, 8.7 Hz), 6.92 (1H, d, J=8.7 Hz), 7.79 (1H, d, J=3.1 Hz).

EXAMPLE 65 trans-N2-(4-Methylsulfonylamino)cyclohexylmethyl-7-methoxy-4,5-dihydro-benzo[2,3]oxepino[4,5-d][1,3]thiazol-2-amine hydrochloride as a beige solid: m.p. 225–230° C.; 438 (ESMS, MH$^+$); $^1$H NMR (free base) δ 1.10–1.30 (4H, m), 1.93 (2H, m), 2.15 (2H, m), 2.98 (3H, s), 3.16 (4H, m), 3.28 (1H, m), 3.88 (3H, s), 4.40 (2H, t, J=5.2 Hz), 5.02 (1H, broad), 6.82 (1H, dd, J=1.5, 8.0 Hz), 7.02 (1H, t, J=8.1 Hz), 7.85 (1H, dd, J=1.5, 8.1 Hz).

EXAMPLE 66 trans-1-Aza-4,5-dihydro-7-methoxy-2-{4-dimethylaminosulfonylamino}cyclohexylmethylamino-6-oxa-3-thia-benzo[e]azulene in 27% yield: 467 (ESMS, MH$^+$); $^1$H NMR (CDCl$_3$) δ 7.84 (dd, 1H, J=1.4, 8.1 Hz), 7.02 (apparent t, 1H, J=8.1 Hz), 6.82 (dd, 1H, J=1.4, 8.0 Hz), 5.11 (m, 1H), 4.41–4.33 (m, 4H), 3.96 (d, 1H, J=8.0 Hz), 3.88 (s, 3H), 3.19–3.10 (m, 4H), 2.78 (s, 6H), 2.20–1.00 (m, 8H); m.p. (HCl salt) 206–208° C.

EXAMPLE 67 trans-N2-(4-Dimethylphosphonylamino)cyclohexylmethyl-9-fluoro-5,6-dihydro-4H-benzo[6,7]cyclohepta[d][1,3]thiazol-2-amine as a yellow solid: m.p. 58–62° C.; CIMS m/e=454 (MH$^+$); $^1$H NMR (300 MHz, CDCl$_3$) δ 1.04 (4H, m), 1.48 (1H, broad), 1.80 (2H, m), 2.00 (2H, m), 2.10 (2H, m), 2.80 (6H, m), 3.04 (2H, m), 3.67 (3H, s), 3.71 (3H, s), 5.62 (1H, broad), 6.81 (1H, m), 7.04 (1H, m), 7.66 (1H, dd, J=2.6, 10.8 Hz).

EXAMPLE 68 trans-N2-(4-Ethoxycarbonylamino)cyclohexylmethyl-9-fluoro-5,6-dihydro-4H-benzo[6,7]cyclohepta[d][1,3]thiazol-2-amine hydrochloride as a white solid: m.p. (HCl salt) 94–97° C.; $^1$H NMR (free base, 300 MHz, CDCl$_3$) δ 1.10 (4H, m), 1.23 (3H, t, J=7.3 Hz), 1.57 (1H, m), 1.86 (2H, m), 2.04 (4H, m), 2.79 (2H, m), 2.86 (2H, t, J=6.9 Hz), 3.11 (2H, t, J=6.2 Hz), 3.44 (1H, m), 4.11 (2H, q, J=7.2 Hz), 4.50 (1H, broad), 5.24 (1H, broad), 6.83 (1H, dt, J=2.8, 8.2 Hz), 7.06 (1H, dd, J=5.9, 8.3 Hz), 7.69 (1H, dd, J=2.8, 10.8 Hz).

EXAMPLE 69

1-Aza-9-fluoro-4,5-dihydro-2-(2-(2-isopropylsulfonylamino)-ethoxy)ethylamino-3-thia-benzo[e]azulene in 60% yield: m.p. (HCl salt) 50–55° C.; $^1$H NMR (300 MHz, CDCl$_3$) δ 1.00 1.37 (d, 6H, J=6.9 Hz), 2.08 (m, 2H), 2.75–2.90 (m, 4H), 3.18 (septet, 1H, J=6.9 HZ), 3.33 (apparent q, 2H, J=5.0 Hz), 3.53 (apparent q, 2H, J=5.0 Hz), 3.61 (t, 2H, J=5.0 Hz), 3.71 (t, 2H, J=4.8 Hz), 4.68 (t, 1H, d, J=5.5 Hz), 5.38 (1H, broad), 6.84 (1H, dt, J=2.8, 8.2 Hz), 7.07 (1H, dd, J=5.9, 8.3 Hz), 7.70 (1H, dd, J=2.8, 10.8 Hz).

EXAMPLE 70

2-(4-Methylsulfonylaminomethyl)cyclohexylamino-4H-chromeno[4,3-d]thiazole (hydrogen chloride salt) was obtained as a blue-green solid in 64% yield: m.p. (HCl salt) 140–144° C.; $^1$H NMR (CDCl$_3$) δ 7.56 (dd, 1H, J=1.3, 7.6 Hz), 7.13 (m, 1H), 6.96 (td, 1H, J=0.9, 7.4 Hz), 6.88 (d, 1H, J=7.4 Hz), 5.31 (m, 3H), 4.78 (t, 1H, J=6.5 Hz), 3.27 (m, 1H), 2.99 (t, 2H, J=6.6 Hz), 2.97 (s, 3H) 2.23 (m, 2H), 1.87 (m, 2H), 1.49 (m, 1H), 1.30–1.06 (m, 4H); 394 (ESMS, MH$^+$).

EXAMPLE 71 trans-1-Aza-4,5-dihydro-8-methoxy-2-(4-methylsulfonyl-amino)cyclohexylmethylamino-3-thia-benzo[e]azulene (hydrogen chloride salt) was obtained as a yellow solid in 50% yield: m.p. (hydrogen chloride salt)

94–97° C.; $^1$H NMR (CD$_3$OD) δ 7.88 (d, 1H, J=8.6 Hz), 6.78 (dd, 1H, J=2.7, 8.8 Hz), 6.68 (d, 1H, J=2.6 Hz), 5.21 (m, 1H), 4.23 (m, 1H), 3.81 (s, 3H), 3.25 (m, 1H), 3.11 (m, 2H), 2.98 (s, 3H), 2.83 (t, 2H, J=7.0 Hz), 2.81 (m, 2H), 2.10 (m, 4H), 1.89 (m, 2H), 1.59 (m, 1H), 1.31–1.07 (m, 4H); 436 (ESMS, MH$^+$).

EXAMPLE 72 trans-1-Aza-4,5-dihydro-8-methoxy-2-(4-methylsulfonylamino-methyl)cyclohexylamino-3-thia-benzo[e]azulene was obtained as a yellow solid in 20% yield: m.p. 224–225° C.; $^1$H NMR δ 7.87 (d, 1H, J=8.7 Hz), 6.78 (dd, 1H, J=2.7, 8.5 Hz), 6.68 (d, 1H, J=2.5 Hz), 4.94 (m, 1H), 4.44 (m, 1H), 3.81 (s, 3H), 3.26 (m, 1H), 2.98 (m, 2H), 2.96 (s, 3H), 2.83 (m, 4H), 2.27 (m, 2H), 2.10 (m, 2H), 1.88 (m, 2H), 1.51 (m, 1H), 1.27–1.04 (m, 4H); 436 (ESMS, MH$^+$).

EXAMPLE 73 trans-1-Aza-4,5-dihydro-2-(4-isopropylsulfonylaminomethyl)-cyclohexylamino-8-methoxy-3-thia-benzo[e]-azulene (hydrogen chloride salt) was obtained as a light brown solid in 3.4% yield: m.p. (HCl salt) 87–89° C.; $^1$H NMR (free base, CDCl$_3$) δ 7.87 (d, 1H, J=8.4 Hz), 6.8 (dd, 1H, J=2.7, 8.4 Hz), 6.69 (d, 1H, J=2.7 Hz), 5.10 (b, 1H), 4.19 (m, 1H), 3.81 (s, 3H), 3.29–3.12 (m, 2H), 2.98 (t, 2H, J=6.6 Hz), 2.82 (m, 4H), 2.25 (m, 2H), 2.09 (m, 2H), 1.91 (m, 2H), 1.50 (m, 1H), 1.38 (d, 6H, J=6.6 Hz), 1.30–1.03 (m, 4H); 464 (ESMS, MH$^+$).

EXAMPLE 74 trans-1-Aza-4,5-dihydro-2-(4-methylsulfonylaminomethyl)-cyclohexylamino-7-methoxy-3-thia-benzo[e]azulene was obtained as a light yellow solid in 59% yield: $^1$H NMR δ 7.75 (dd, 1H, J=1.2, 8.0 Hz), 7.01 (t, 1H, J=8.1 Hz), 6.81 (dd, 1H, J=1.2, 7.0 Hz), 4.81 (m, 1H), 4.40 (t, 2H, J=5.1 Hz), 4.34 (m, 1H), 3.88 (s, 3H), 3.34 (m, 1H), 3.18 (t, 2H, J=5.0 Hz), 3.03 (t, 2H, J=7.0 Hz), 2.97 (s, 3H), 2.28 (m, 2H), 1.91 (m, 2H), 1.50 (m, 1H), 1.30–1.08 (m, 4H); 438 (ESMS, MH$^+$).

EXAMPLE 75 trans-1-Aza-4,5-dihydro-2-(4-ethylcarbonylaminomethyl)-cyclohexylamino-9-fluoro-3-thia-benzo[e]azulene was obtained as a light yellow solid in 87% yield: $^1$H NMR δ 7.69 (dd, 1$_1$, J=2.7, 10.8 Hz), 7.06 (dd, 1H, J=5.9, 8.4 Hz), 6.83 (td, 1H, J=2.8, 8.2 Hz), 5.50 (m, 1H), 4.82 (m, 1H), 3.29 (m, 1H), 3.15 (t, 2H, J=6.5 Hz), 2.86 (t, 2H, J=6.9 Hz), 2.79 (m, 2H), 2.21 (m, 4H), 2.07 (m, 2H), 1.84 (m, 2H), 1.51 (m, 1H), 1.29–1.03 (m, 4H), 1.17 (t, 3H, J=7.5 Hz); 402 (ESMS, MH$^+$).

EXAMPLE 76 trans-1-Aza-9-fluoro-4,5-dihydro-2-(4-(4-morpholinyl)-sulfonylaminomethyl)cyclohexylamino-3-thia-benzo[e]azulene (hydrogen chloride salt) was obtained as a light yellow solid in 28% yield: $^1$H NMR (free base) δ 7.67 (dd, 1H, J=2.8, 10.8 Hz), 7.06 (dd, 1H, J=5.9, 8.0 Hz), 6.83 (td, 1H, J=2.7, 8.1 Hz), 4.96 (d, 1H, J=8.0 Hz), 4.59 (t, 1H, J=6.1 Hz), 3.74 (m, 4H), 3.23 (m, 5H), 2.93 (t, 2H, J=4.8 Hz), 2.86 (t, 2H, J=6.9 Hz), 2.79 (m, 2H), 2.24 (m, 2H), 2.07 (m, 2H), 1.84 (m, 2H), 1.46 (m, 1H), 1.30–1.02 (m, 4H); 495 (ESMS, MH$^+$).

EXAMPLE 77 trans-1-Aza-9-fluoro-4,5-dihydro-2-(4-(2-methoxy)ethoxycarbonylaminomethyl)cyclohexylamino-3-thia-benzo[e]azulene 2-methoxyethyl N-(t4-[(9-fluoro-5,6-dihydro-4H-benzo[6,7]-cyclohepta[d][1,3]thiazol-2-yl)amino]cyclohexyl}methyl)-carbamate:

tert-butyl N-[(4-{[(benzoylamino)carbothioyl]amino}cyclo-hexyl)methyl]carbamate: A solution of tert-butyl N-[(4-aminocyclohexyl)methyl]carbamate (4.683 g, 20.5 mmol) and benzoyl isothiocyanate (3.77 g, 23.1 mmol) in 180 ml THF was stirred at room temperature for 20 hours. The solvent was removed in vacuo to yield a golden viscous oil. The oil was triturated with 250 ml hexane and the resulting solid was collected by filtration and washed with hexane. The off-white solid was washed several times with hexane and was dried under vacuum to yield 91% (7.32 g) of the desired product as an off-white solid: $^1$H-NMR (CDCl$_3$) δ 1.20 (6H, m), 1.44 (9H, s), 1.83 (2H, m), 2.25 (2H, m), 3.01 (2H, t, J=6.4 Hz), 4.20 (1H, m), 4.62 (1H, m), 7.51 (2H, t, J=7.9 Hz), 7.60 (1H, t, J=7.4 Hz), 7.81 (2H, d, J=7.2 Hz), 8.93 (1H, s); 392 (ESMS, MH$^+$).

tert-butyl-N-({4-[(aminocarbothioyl)amino]cyclohexyl}-methyl)carbamate: A solution of tert-butyl-N-[(4-{[(benzoylamino)carbothioyl]amino}- cyclohexyl)methyl]carbamate (7.30 g, 18.6 mmol) in 110 ml MeOH was prepared. Then, a solution of potassium carbonate (5.15 g, 37.3 mmol) in 50 ml water was added to the stirred solution. The solution was stirred at room temperature for 18 hours. The solvent was removed in vacuo and the residue was extracted several times with EtOH. The combined EtOH extracts were evaporated to dryness to yield 6.15 g of an off-white solid. The solid was re-dissolved in 200 ml acetone and stirred for 20 minutes. The solution was filtered by suction to remove the insoluble salts and the filtrate was evaporated to yield 98% (5.23 g) of the desired product as a slightly yellow solid: $^1$H-NMR (CDCl$_3$) δ 1.10 (6H, m), 1.43 (9H, s), 1.80 (2H, m), 2.10 (2H, m), 2.95 (2H, t, J=6.4 Hz), 4.75 (1H, broad), 6.03 (2H, s), 6.64 (1H, broad); 288 (ESMS, MH$^+$).

6-Bromo-3-fluoro-6,7,8,9-tetrahydro-5H-benzo[a]cyclohepten-5-one: A solution of 8-fluoro-1-benzosuberone (20.00 g, 112.2 mmol) in 125 ml glacial acetic acid was prepared. Bromine (5.80 ml, 113 mmol) was added dropwise with stirring. After addition was complete, the solution was poured into 400 ml water and extracted with EtOAc (500 ml). The EtOAc layer was separated and washed with 500 ml water. The organic layer was dried over MgSO$_4$, filtered and evaporated to yield 100% (28.9 g) of the desired product as a viscous oil: $^1$H-NMR (CDCl$_3$) δ 2.00 (2H, m), 2.33 (2H, m), 2.84 (1H, m), 3.00 (1H, m), 4.83 (1H, m), 7.13 (2H, m), 7.29 (1H, dd).

tert-Butyl-N-({4-[(9-fluoro-5,6-dihydro-4H-benzo[6,7]-cyclohepta-[d][1,3]thiazol-2-yl)amino]cyclohexyl}methyl)-carbamate: A solution of tert-butyl-N-({4-[(aminocarbothioyl)amino]cyclohexyl}methyl)carbamate (22.4 g, 78.0 mmol), 6-bromo-3-fluoro-6,7,8,9-tetrahydro-5H-benzo[a]cyclohepten-5-one (20.1 g, 78.0 mmol), and 22.5 ml diisopropylethylamine in 260 ml absolute ethanol was heated at reflux for 3 hours. The solvent was removed in vacuo with gentle heating (~40 C). The resulting viscous golden oil was taken up into 400 ml EtOAc and washed with water (600 ml). The EtOAc layer was separated and evaporated to yield 39.0 g of a viscous golden oil. The oil was chromatographed on silica-gel eluting with EtOAc to yield 34.5 g of the desired product (99% yield): $^1$H-NMR (CDCl$_3$) δ 1.18 (6H, h, J=12.2 Hz), 1.44 (9H, s), 1.81 (2H, m), 2.22 (2H, m), 2.79 (2H, m), 2.86 (2H, t, J=7.1 Hz), 3.00 (2H, t, J=6.3 Hz), 3.25 (1H, broad), 4.62 (1H, broad), 4.86 (1H, broad), 6.83 (1H, dt, J=2.9 Hz), 7.04 (1H, m), 7.70 (1H, dd, J=2.8 Hz).

trans-N2-[4-(Aminomethyl)cyclohexyl]-9-fluoro-5,6-dihydro-4H-benzo[6,7]cyclohepta[d][1,3]thiazol-2-amine: A solution of trans-tert-butyl N-({4-[(9-fluoro-5,6-dihydro-4H-benzo[6,7]cyclohepta[d][1,3]thiazol-2-yl)amino]cyclohexyl}-methyl)carbamate (34.5 g, 77.0 mmol) in 200 ml EtOAc and 100 ml 4N HCl in dioxane was stirred at room temperature for 2 hours. The resulting solid was collected by filtration and the solid product washed with $Et_2O$ and dried under vacuum to yield 25.9 g of the desired product as a pale yellow solid. An additional 1.43 g of the product was obtained by allowing the filtrate to stand in a closed flask for several days. The overall yield was 85%: $^1$H-NMR ($CD_3OD$) δ 1.25 (2H, m), 1.51 (2H, m), 1.70 (1H, broad), 1.95 (2H, m), 2.18 (4H, m), 2.80 (6H, m), 3.63 (1H, broad), 7.11 (1H, dt, J=2.5 Hz, 8.4 Hz), 7.36 (2H, m); 346 (ESMS, $MH^+$).

trans-1-Aza-9-fluoro-4,5-dihydro-2-(4-(2-methoxy)ethoxy-carbonylaminomethyl)cyclohexylamino-3-thiabenzo[e]azulene 2-methoxyethyl N-({4-[(9-fluoro-5,6-dihydro-4H-benzo[6,7]cyclohepta[d][1,3]thiazol-2-yl)amino]cyclohexyl}-methyl)carbamate: A solution trans-N2-[4-(aminomethyl)-cyclohexyl]-9-fluoro-5,6-dihydro-4H-benzo[6,7]cyclohepta-[d][1,3]thiazol-2-amine (0.30 g, 0.72 mmol) in anhydrous THF (3 ml) and triethylamine (1.0 ml) was flushed with nitrogen. The solution was stirred for 5 minutes and 0.095 ml chloroformic acid 2-methoxyethyl ester (0.114 g, 0.82 mmol) was added dropwise to the stirring solution via syringe. The solution was stirred at room temperature for 2 hours. The solvent was removed in vacuo and the residue was chromatographed on silica-gel eluting with 1:1 EtOAc/Hexane to yield 25% (80 mg) of the desired product as a colorless viscous oil: $^1$H-NMR ($CDCl_3$) δ 1.11 (4H, septet, J=9.8 Hz), 1.42 (1H, broad), 1.80 (2H, m), 2.04 (2H, m), 2.20 (2H, m), 2.77 (2H, m), 2.84 (2H, t, J=6.9 Hz), 3.04 (2H, t, J=6.4 Hz), 3.24 (1H, broad), 3.38 (3H, s), 3.58 (2H, m), 4.22 (2H, m), 4.90 (1H, broad), 5.00 (1H, d), 6.81 (1H, dt, J=2.8 Hz), 7.03 (1H, m), 7.68 (1H, dd, J=2.7 Hz, 10.9 Hz); 448 (ESMS, $MH^+$).

EXAMPLE 78 trans-N2-(4-(1-Morpholinylsulfonylaminomethyl)cyclohexyl-8-methoxy-5,6-dihydro-4H-benzo[6,7]cyclohepta[d][1,3]thiazol-2-amine hydrochloride:

Prepared from trans-N2-(4-aminomethyl)cyclohexyl-8-methoxy-5,6-dihydro-4H-benzo[6,7]cyclohepta[d][1,3]thiazol-2-amine and 1-morpholinylsulfonyl chloride as a light brown solid: m.p. 130–132° C.; 507 (ESMS, $MH^+$); $^1$H NMR (free base) δ 7.88 (dd, 1H, J=0.4, 8.7 Hz), 6.78 (dd, 1H, J=2.4, 8.8 Hz), 6.68 (d, 1H, J=2.3 Hz), 4.85 (m, 1H), 4.25 (m, 1H), 3.81 (s, 3H), 3.73 (m, 4H), 3.30 (m, 1H), 3.25 (m, 4H), 2.96 (m, 2H), 2.81 (m, 4H), 2.26 (m, 2H), 2.10 (m, 2H), 1.87 (m, 2H), 1.49 (m, 1H), 1.30–1.03 (m, 4H).

EXAMPLE 79

3-({4-[(9-fluoro-5,6-dihydro-4H-benzo[6,7]cyclohepta[d][1,3]thiazol-2-yl)amino]cyclohexyl}methyl)-1,3-oxazolan-2-one:

2-chloroethyl-N-({4-[(9-fluoro-5,6-dihydro-4H-benzo[6,7]-cyclohepta[d][1,3]thiazol-2-yl)amino]cyclohexyl}methyl)-carbamate: A solution of trans-N2-[4-(aminomethyl)cyclohexyl]-9-fluoro-5,6-dihydro-4H-benzo-[6,7]cyclohepta[d][1,3]thiazol-2-amine (5.00 g, 11.95 mmol), 20 ml anhydrous pyridine, and 8 ml diisopropylethylamine was stirred under $N_2$. Then 2-chloroethyl chloroformate (1.40 ml, 13.6 mmol) was added dropwise to the stirring solution. The solution was stirred at room temperature for 2 hours and then poured into 250 ml water and extracted with 250 ml EtOAc. The extract was separated and evaporated to yield 100% (5.40 g) of the desired product as a highly viscous golden oil: $^1$H-NMR ($CDCl_3$) δ 1.13 (3H, m), 1.43 (1H, m), 1.82 (2H, m), 2.06 (2H, m), 2.22 (2H, m), 2.81 (4H, m), 3.06 (2H, t, J=6.4 Hz), 3.25 (1H, m), 3.70 (3H, m), 4.31 (2H, t, J=5.7 Hz), 4.89 (2H, m), 6.82 (1H, t, J=2.8 Hz), 7.04 (1H, m), 7.70 (1H, dd, J=2.7, 10.8 Hz); 452 (ESMS, $MH^+$).

3-({4-[(9-Fluoro-5,6-dihydro-4H-benzo[6,7]cyclohepta[d][1,3]thiazol-2-yl)amino]cyclohexyl}methyl)-1,3-oxazolan-2-one: To a stirred solution of 2-chloroethyl-N-({4-[(9-fluoro-5,6-dihydro-4H-benzo[6,7]-cyclohepta[d][1,3]thiazol-2-yl)amino]cyclohexyl}methyl)carbamate (5.4 g, 11.95 mmol) in 100 ml anhydrous DMF was added NaH (60% in mineral oil) (0.6 g, 15.0 mmol). TLC (EtOAc) indicated that the reaction had proceeded to approximately 40% completion after 15 minutes. An additional 0.58 g (14.5 mmol) NaH (60% in mineral oil) was added and the solution was stirred at room temperature for another 15 minutes. TLC indicated the reaction was complete. The solution was poured into water (500 ml) and was extracted with EtOAc. The extract was separated and evaporated to yield a dark viscous oil. The oil was chromatographed on silica-gel eluting with 2:1 EtOAc/hexane to yield a white solid. The solid was dissolved in 40 ml $CHCl_3$ and 10 ml 1N HCl in $Et_2O$ was added to the solution. The volatiles were removed and the resulting solid was triturated with $Et_2O$. The solution was filtered and the slightly tan solid washed with ether and dried to yield 52% (2.83 g) of the desired product as the HCl salt: $^1$H-NMR (Free-base) ($CDCl_3$) δ 1.16 (4H, m), 1.60 (1H, m), 1.80 (2H, m), 2.05 (2H, m), 2.22 (2H, m), 2.81 (4H, m), 3.12 (2H, d, J=7.3 Hz), 3.27 (1H, m), 3.57 (2H, t, J=8.2 Hz), 4.33 (2H, t, J=8.0 Hz), 5.05 (1H, d, J=7.7 Hz), 6.83 (1H, dt, J=2.7, 8.2 Hz), 7.05 (1H, m), 7.68 (1H, dd, J=2.7, 10.8 Hz). m.p. (HCl salt) 223–225° C. Anal. Calcd. For $C_{22}H_{27}N_3ClFO_2S$: C, 58.5; H, 6.0; N, 9.3. Found: C, 58.43; H, 6.06; N, 9.38; 416 (ESMS, $MH^+$).

EXAMPLE 80

N1-({4-[(9-fluoro-5,6-dihydro-4H-benzo[6,7]cyclohepta-[d][1,3]thiazol-2-yl)amino]cyclohexyl}methyl)-2-methoxyacetamide: To a stirred, septum capped solution of trans-N2-[4-(aminomethyl)cyclohexyl]-9-fluoro-5,6-dihydro-4H-benzo[6,7]cyclohepta[d][1,3]thiazol-2-amine (5.00 g, 11.95 mmol) in anhydrous pyridine (20 ml) and diisopropylethylamine (10 ml) was added methoxyacetyl chloride (1.20 ml, 13.1 mmol) dropwise. The solution was stirred at room temperature for 2 hours and was then poured into 250 ml water and extracted with 250 ml EtOAc. The extract was evaporated to yield a golden viscous oil which was chromatographed on silica-gel eluting with EtOAc to yield 88% (4.40 g) of the desired product as a slightly yellow solid. A small portion of the product was recrystallized from EtOAc (m.p. 95–97° C.). The free-base was dissolved in 60 ml $CHCl_3$ and converted to its HCl salt by adding 14.0 ml 1.0 N HCl in ether followed by evaporation of the solvent. The resulting foam was stirred with ether (75 ml), filtered and washed with ether to yield the HCl salt as a solid: $^1$H-NMR (Free-base) ($CDCl_3$) δ 1.12 (4H, m), 1.45 (1H, m), 1.81 (2H, m), 2.05 (2H, m), 2.21 (2H, m), 2.80 (4H, m), 3.16 (2H, t, J=6.5 Hz), 3.25 (1H, m), 3.41 (3H, s), 3.89 (2H, s), 5.03 (1H, d, J=8.0 Hz), 6.62 (1H, broad t), 6.81 (1H, dt, J=2.9, 8.3 Hz), 7.03 (1H, m), 7.69 (1H, dd, J=2.8, 10.8 Hz). m.p. 63–65° C. Anal. Calcd. For $C_{22}H_{29}N_3O_2SFCl$+ 0.5$CHCl_3$: C, 52.61; H, 5.79; N, 8.18. Found: C, 52.61; H, 5.92; N, 8.08; 418 (ESMS, $MH^+$).

EXAMPLE 81

N1-({4-[(9-fluoro-5,6-dihydro-4H-benzo[6,7]-cyclohepta-[d][1,3]thiazol-2-yl)amino]cyclohexyl}methyl)

acetamide: To a stirred, septum capped solution of trans-N2-[4-(aminomethyl)cyclohexyl]-9-fluoro-5,6-dihydro-4H-benzo-[6,7]cyclohepta[d][1,3]thiazol-2-amine (0.165 g, 0.394 mmol) in 3.0 ml anhydrous pyridine was added 0.034 ml (0.038 g, 0.48 mmol) acetyl chloride dropwise. Stirring at room temperature was continued for 90 minutes and the solution was then poured into 50 ml water and extracted with EtOAc (2×50 ml). The combined extracts were evaporated to yield 0.126 g of the crude product as a viscous golden oil. The oil was chromatographed on preparative TLC eluting with EtOAc to yield 28% (0.042 g) of the desired product as a white solid: $^1$H-NMR (CDCl$_3$) δ 1.13 (4H, m), 1.43 (1H, m), 1.80 (2H, m), 1.98 (3H,s), 2.05 (2H, m), 2.21 (2H, m), 2.80 (4H, m), 3.10 (2H, t, J=6.5 Hz), 3.24 (1H, m), 5.00 (1H, d, J=7.8 Hz), 5.75 (1H, m), 6.81 (1H, dt, J=2.8, 8.2 Hz), 7.04 (1H, m), 7.69 (1H, dd, J=2.7, 10.8 Hz); m.p. 88–91° C.

EXAMPLE 82 trans-1-Aza-9-fluoro-4,5-dihydro-2-(4-(N-propylformamido)-methyl)cyclohexylamino-3-thia-benzo[e]azulene (hydrogen chloride salt) was obtained as a yellow solid in 54% yield: $^1$H NMR (free base) δ 8.10 (s, 0.5H), 8.00 (s, 0.5H), 7.68 (m, 1H), 7.04 (m, 1H), 6.83 (m, 1H), 5.07 (m, 1H), 3.31–3.02 (m, 5H), 2.85 (m, 4H), 2.23 (m, 2H), 2.05 (m, 2H), 1.77 (m, 2H), 1.58 (m, 3H), 1.26–0.87 (m, 7H); 416 (ESMS, MH$^+$).

EXAMPLE 83 trans-1-Aza-9-fluoro-4,5-dihydro-2-(4-(N-isopropylformamido)methyl)cyclohexylamino-3-thia-benzo[e]azulene (hydrogen chloride salt) was obtained as a yellow solid in 48% yield: m.p. (HCl salt) 106–107° C.; $^1$H NMR (CD$_3$OD) δ 8.22 (s, 0.6H), 7.98 (s, 0.4H), 7.37 (m, 2H), 7.12 (m, 1H), 4.18 (m, 0.4H), 3.73 (m, 0.6H), 3.60 (m, 1H), 3.17 (m, 2H), 2.78 (m, 4H), 2.19 (m, 4H), 1.86 (m, 2H), 1.74 (m, 1H), 1.41 (m, 2H), 1.32 (d, 4H), 1.31 (d, 2H), 1.17 (m, 2H); 416 (ESMS, MH$^+$).

EXAMPLE 84

N1-{4-[(4,5-dihydrobenzo[2,3]oxepino[4,5-d][1,3]thiazol-2-ylamino)methyl]cyclohexyl}-2-methoxyacetamide:

Benzyl-N-[4-({[(benzoylamino)carbothioyl]amino}methyl)-cyclohexyl]carbamate: A solution of benzyl N-[4-(aminomethyl)cyclohexyl]carbamate HCl (3.46 g, 11.6 mmol) and diisopropylethylamine (6.0 ml) in anhydrous THF (90 ml) was stirred at room temperature for 20 minutes. To this solution was added benzoylisothiocyanate (2.00 g, 12.3 mmol) and the reaction mixture stirred at room temperature for 14 hours. The solution was poured into water (200 ml) and extracted with Et$_2$O (2×150 ml). The organic layer was dried over MgSO$_4$, filtered and evaporated to yield a solid. The solid was triturated with hexane and filtered to yield 99% (5.023 g) of the desired product.

Benzyl-N-(4-{[(aminocarbothioyl)amino]methyl}cyclohexyl)-carbamate: To a solution of benzyl N-[4-({[(benzoyl-amino)carbothioyl]amino}methyl)cyclohexyl]carbamate (5.023 g, 11.4 mmol) in MeOH (110 ml) was added a solution of K$_2$CO$_3$ (3.5 g, 25.3 mmol) in water (30 ml). The solution was stirred for 24 hours at room temperature and the solvent was removed in vacuo with repeated additions of MeOH to azeotropically remove water. The resulting solid was treated with acetone (60 ml) and filtered. The filtrate was evaporated to yield 95% (3.47 g) of a yellow solid.

Benzyl-N-{4-[(4,5-dihydrobenzo[2,3]oxepino[4,5-d][1,3]-thiazol-2-ylamino)methyl]cyclohexyl}carbamate: A solution containing benzyl N-(4-{[(aminocarbothioyl)amino]methyl}-cyclohexyl)carbamate (3.45 g, 10.73 mmol), 4-bromo-2,3,4,5-tetrahydro-1-benzoxepin-5-one (2.60 g, 10.78 mmol), diisopropylethylamine (2.50 ml) and EtOH (50 ml) was heated at reflux for 4 hours. The solvent was removed and the residue was chromatographed on silica-gel eluting with 1:3 EtOAc/Hexane to yield 65% (3.2 g) of the product as a white solid: m.p. 124–127° C.; $^1$H-NMR (CDCl$_3$) δ 1.09 (4H, pentet, J=10.4 Hz), 1.55 (1H, broad), 1.83 (2H, m), 2.04 (2H, broad), 3.10 (2H, t, J=6.2 Hz), 3.15 (2H, t, J=5.2 Hz), 3.43 (1H, broad) 4.33 (2H, t, J=5.2 Hz), 4.62 (1H, d, J=8.0 Hz), 5.08 (2H, s), 5.31 (1H, m), 7.00 (1H, dd, J=1.2 Hz, 7.8 Hz), 7.12 (2H, m), 7.35 (5H, s), 8.25 (1H, dd, J=1.7 Hz, 7.8 Hz); 464 (ESMS, MH$^+$).

N2-[(4-aminocyclohexyl)methyl]-4,5-dihydrobenzo[2,3]oxepino[4,5-d][1,3]thiazol-2-amine: A solution containing benzyl-N-{4-[(4,5-dihydrobenzo[2,3]oxepino[4,5-d]-[1,3]-thiazol-2-ylamino)methyl]cyclohexyl}carbamate (3.00 g, 6.47 mmol), glacial acetic acid (50 ml) and conc. HCl (20 ml) was heated to a gentle reflux for 45 minutes. The solvent was removed on the rotor-vap with gentle heating and the residue diluted with 150 ml water. The resulting solution was made basic with NaOH (pH~11) At this point, much of the product precipitated out of solution and stuck to the sides of the flask. EtOAc (200 ml) was added and the solution was shaken vigorously. The phases were separated and the aqueous phase extracted with EtOAc. The combined extracts were washed with water and evaporated to yield 2.30 g of a brown viscous oil. The oil was taken up into 40 ml EtOAc and 5 ml 4M HCl in dioxane added. The resulting dihydrochloride salt was obtained by filtration and washed with EtOAc and then several times with ether. Upon drying, 100% (2.6 g) of the salt was obtained as a slightly tan free-flowing solid: $^1$H-NMR (d$_4$-MeOH) δ 1.21 (2H, m), 1.43 (2H, m), 1.79 (1H, m), 1.99 (2H, m), 2.10 (2H, m), 3.09 (1H, m), 3.18 (2H, t, J=5.0 Hz), 3.35 (2H, d, J=6.7 Hz), 4.32 (2H, t, J=5.3 Hz), 7.12 (1H, dd, J=1.1, 8.0 Hz), 7.22 (1H, m), 7.33 (1H, m), 7.70 (1H, dd, J=1.3, 8.0 Hz); 330 (ESMS, MH$^+$).

To a stirred solution of N2-[(4-aminocyclohexyl)methyl]-4,5-dihydrobenzo[2,3]oxepino[4,5-d][1,3]thiazol-2-amine (0.600 g, 1.49 mmol), anhydrous pyridine (3 ml), and diisopropylethylamine (3 ml) was added methoxyacetyl chloride (0.163 ml, 1.78 mmol) dropwise. The solution was stirred for 30 minutes at room temperature and then poured into water (60 ml) and extracted with EtOAc. The extract was evaporated and the residue chromatographed on silica-gel eluting with EtOAc to yield 79% (470 mg) of the product as a white solid. The product was dissolved in chloroform and converted to its HCl salt with 1N HCl in Et$_2$O to yield 522 mg of the salt as a white solid: m.p. (HCl salt) 234–237° C.; $^1$H-NMR (free base, CDCl$_3$) δ 1.20 (4H, m), 1.80 (2H, broad), 2.00 (4H, m), 3.13 (4H, t, J=5.0 Hz), 3.40 (3H, s), 3.79 (1H, broad), 3.86 (2H, s), 4.34 (2H, t, J=5.1 Hz), 6.35 (1H, d), 7.05 (1H, dd, J=1.3 Hz, 7.7 Hz), 7.28 (2H, m), 7.99 (1H, d, J=8.3 Hz); 402 (ESMS, MH$^+$).

EXAMPLE 85

N-{[4-(4,5-Dihydrobenzo[2,3]oxepino[4,5-d][1,3]thiazol-2-ylamino)cyclohexyl]methyl}-N-propylformamide:

N1-{[4-(4,5-Dihydrobenzo[2,3]oxepino[4,5-d][1,3]thiazol-2-ylamino)methyl]}propanamide: To a stirred solution of N2-[4-(aminomethyl)cyclohexyl]-4,5-dihydrobenzo[2,3]oxepino[4,5-d][1,3]thiazol-2-amine (0.600 g, 1.49 mmol) in anhydrous pyridine (3 ml) and diisopropylethylamine (3 ml) was added propionyl chloride (0.144 ml, 1.66 mmol) dropwise. The solution was stirred for 20 minutes at room temperature and then poured into water (50 ml) and extracted with EtOAc. The solvent was removed and the residue chromatographed on silica-gel eluting with EtOAc to yield 70% (402 mg) of the product as a light yellow solid: $^1$H-NMR (CDCl$_3$) δ 1.12 (6H, m), 1.50 (1H, m), 1.65 (1H, m), 1.85 (2H, d, J=12.1 Hz), 2.22 (4H, m), 3.16 (4H, t, J=5.3 Hz), 3.32 (1H, m), 4.33 (2H, t, J=5.2 Hz), 4.81 (1H, m), 5.49 (1H, m), 7.00 (1H, d, J=8.5 Hz), 7.15 (2H, m), 8.25 (1H, d, J=8.1 Hz). m.p. 56–60° C. FAB+m/z=386 (MH$^+$).

N2-{4-[(Propylamino)methyl]cyclohexyl}-4,5-dihydrobenzo-[2,3]oxepino[4,5-d][1,3]thiazol-2-amine: To a solution of N1-{[4-(4,5-dihydrobenzo[2,3]oxepino[4,5-d][1,3]thiazol-2-ylamino)cyclohexyl]methyl}propanamide (0.380 g, 0.944 mmol) in anhydrous THF (7 ml) was added 1M BH$_3$ in THF (2.0 ml, 2.0 mmol). The solution was stirred for several hours at room temperature. TLC (EtOAc) indicated reaction to be incomplete and an additional 2.5 ml 1M BH$_3$ in THF was added to the solution which was then stirred overnight. 4N HCl (25 ml) was slowly added to the stirred solution and the solution was washed with EtOAc. The aqueous layer was made basic by addition of 20% NaOH. The resulting solution was extracted with EtOAc and the extract washed with water. Upon removal of the solvent, 72% (254 mg) of the product was obtained as a white solid: $^1$H-NMR (CDCl$_3$) δ 0.88 (3H, t, J=7.3 Hz), 1.12 (4H, m), 1.43 (3H, m), 1.75 (2H, m), 2.14 (2H, m), 2.41 (2H, d, J=6.6 Hz), 2.51 (2H, t, J=7.4 Hz), 2.60 (1H, m), 3.10 (2H, t, J=5.0 Hz), 3.22 (1H, m), 4.27 (2H, t, J=5.0 Hz), 5.35 (1H, m), 6.95 (1H, d, J=7.6 Hz), 7.06 (2H, m), 8.20 (1H, d, J=7.3 Hz); 372 (ESMS, MH$^+$).

N-{[4-(4,5-dihydrobenzo[2,3]oxepino[4,5-d][1,3]thiazol-2-ylamino)cyclohexyl]methyl}-N-propylformamide: To a solution of N2-{4-[(propylamino)methyl]cyclohexyl}-4,5-dihydrobenzo[2,3]oxepino[4,5-d][1,3]thiazol-2-amine (0.254 g, 0.68 mmol) in anhydrous THF (4 ml) was added 1H-benzotriazole-1-carboxaldehyde (0.110 g, 0.75 mmol). The solution was stirred at room temperature for 1 hour and then poured into 2N NaOH (50 ml) and extracted with EtOAc (60 ml). The extract was separated and evaporated to yield 295 mg of a viscous oil. Chromatography on silica-gel eluting with 1:1 EtOAc/hexane yielded 56% (152 mg) of the product as a white solid: $^1$H-NMR (CDCl$_3$) δ 0.90 (3H, m), 1.14 (4H, m), 1.58 (2H, m), 1.78 (2H, m), 2.23 (2H, m), 3.20 (8H, m), 4.32 (2H, t, J=4.9 Hz), 5.03 (1H, m), 6.99 (1H, m), 7.12 (2H, m), 8.01 (0.5H, s), 8.11 (0.5H, s), 8.22 (1H, d); m.p. 53–55° C.; 400 (ESMS, MH$^+$).

EXAMPLE 86

N-{4-[(4,5-dihydrobenzo[2,3]oxepino[4,5-d][1,3]thiazol-2-ylamino)methyl]cyclohexyl}-N-(2-methoxyethyl)formamide N2-({4-[(2-methoxyethyl)amino]cyclohexyl}methyl)-4,5-dihydrobenzo[2,3]oxepino[4,5-d][1,3]thiazol-2-amine: To a stirred solution of N1-{4-[(4,5-dihydrobenzo[2,3]oxepino[4,5-d][1,3]thiazol-2- ylamino)-methyl]cyclohexyl}-2-methoxyacetamide (free-base) (0.450 g, 1.12 mmol) in anhydrous THF (5 ml) was added 5.0 ml 1M BH$_3$ in THF (5.0 mmol). The solution was stirred at room temperature for 26 hours. 4N HCl (12 ml) was slowly added to the stirred solution and stirred continued for 1 hour. The solution was made basic with 2N NaOH (pH~9) and was extracted with EtOAc. Upon evaporation of the solvent, 90% (390 mg) of the desired amine was obtained as a highly viscous colorless oil. The compound was converted to its dihydrochloride salt in chloroform with 1N HCl in Et$_2$O. Evaporation of the solvent gave 460 mg of the salt as a slightly hygroscopic white solid: m.p. 243–245° C. (dec); $^1$H-NMR (CDCl$_3$) δ 1.08 (4H, t, J=10.8 Hz), 1.6 (2H, broad), 1.91 (4H, m), 2.41 (1H, broad), 2.80 (2H, t, J=4.9 Hz), 3.15 (4H, m), 3.35 (3H, s), 3.49 (2H, t, J=5.3 Hz), 4.32 (2H, t, J=5.4 Hz), 5.13 (1H, broad t), 6.98 (1H, dd, J=1.3 Hz, 7.7 Hz), 7.12 (2H, m), 8.24 (1H, dd, J=1.6 Hz, 7.9 Hz); 388 (ESMS, MH$^+$).

N-{4-[(4,5-dihydrobenzo[2,3]oxepino[4,5-d][1,3]thiazol-2-ylamino)methyl]cyclohexyl}-N-(2-methoxyethyl)formamide: To a stirred solution of N2-({4-[(2-methoxyethyl)amino]cyclohexyl}methyl)-4,5-dihydrobenzo-[2,3]oxepino[4,5-d][1,3]thiazol-2-amine (free-base) (0.356 g, 0.92 mmol) in anhydrous THF (4 ml) was added 1H-benzotriazole-1-carboxaldehyde (0.144 g, 0.98 mmol). The solution was stirred for 5 minutes at room temperature and TLC (EtOAc) indicated reaction to be complete. The solution was poured into 2N NaOH (50 ml) and extracted with EtOAc (60 ml). The extract was evaporated to yield 420 mg of the crude product as a white solid. The product was chromatographed on silica-gel eluting with 3:1 EtOAc/hexane to yield 78% (300 mg) of a white solid. The material was converted to its HCl salt in chloroform with 1M HCl in Et$_2$O. Upon evaporation of the solvent, a white hygroscopic solid was obtained. The solid was triturated with hexane, filtered and dried to yield 330 mg of a non-hygroscopic free flowing white solid: m.p. 164–166° C.; $^1$H-NMR (CDCl$_3$) δ 1.11 (2H, p), 1.53 (3H, m), 1.90 (5H, m), 3.14 (4H, m), 3.32 (3H, s), 3.43 (4H, m), 4.34 (2H, t), 5.43 (1H, broad), 7.00 (1H, d), 7.12 (2H, m), 8.08 (0.4H, s), 8.18 (0.6H, s), 8.24 (1H, dd); 416 (ESMS, MH$^+$).

EXAMPLE 87 trans-1-Aza-2-(4-(n-(ethyl)formamido)cyclohexyl)methyl-amino-4,5-dihydro-6-oxa-3-thia-benzo[e]azulene:

trans-2-(4-Acetamido)cyclohexylmethylamino-1-aza-4,5-dihydro-6-oxa-3-thia-benzo[e]azulene:

Benzyl-N-[4-({[(benzoylamino)carbothioyl]amino}methyl)-cyclohexyl]carbamate: A solution of benzyl N-[4-(aminomethyl)cyclohexyl]carbamate HCl (3.46 g, 11.58 mmol) and diisopropylethylamine (6.0 ml) in anhydrous THF (90 ml) was stirred at room temperature for 20 minutes. To this solution was added benzoylisothiocyanate (2.00 g, 12.3 mmol). The solution was stirred at room temperature for 14 hours, poured into water (200 ml) and then extracted with Et$_2$O (2×150 ml). The organic layer was dried over MgSO$_4$, filtered and evaporated to yield a solid. The solid was triturated with hexane and filtered to yield 99% (5.023 g) of the desired product.

Benzyl-N-(4-{[(aminocarbothioyl)amino]methyl}cyclohexyl)-carbamate: To a solution of benzyl N-[4-({[(benzoylamino)carbothioyl]amino}methyl)cyclohexyl]carbamate (5.02 g, 11.4 mmol) in MeOH (110 ml) was added a solution of K$_2$CO$_3$ (3.5 g, 25.3 mmol) in water (30 ml) The solution was stirred for 24 hours at room temperature. The solvent was removed in vacuo with repeated additions of MeOH to azeotropically remove water. The resulting solid was treated with acetone (60 ml) and filtered. The filtrate was evaporated to yield 95% (3.47 g) of a yellow solid.

Benzyl-N-{4-[(4,5-dihydrobenzo[2,3]oxepino[4,5-d][1,3]-thiazol-2-ylamino)methyl]cyclohexyl}carbamate: A solution containing benzyl N-(4-{[(aminocarbothioyl)amino]methyl}-cyclohexyl)carbamate (3.45 g, 10.73 mmol), 4-bromo-2,3,4,5-tetrahydro-1-benzoxepin-5-one (2.60 g, 10.78 mmol), and diisopropylethylamine (2.50 ml) in EtOH (50 ml) was heated at reflux for 4 hours. The solvent was removed and the residue was chromatographed on silica gel eluting with 1:3 EtOAc/hexane to yield 65% (3.2 g) of the product as a white solid: m.p. 124–127° C.; $^1$H-NMR (CDCl$_3$) δ 1.09 (4H, pentet, J=10.4 Hz), 1.55 (1H, broad), 1.83 (2H, m), 2.04 (2H, broad), 3.10 (2H, t, J=6.2 Hz), 3.15 (2H, t, J=5.2 Hz), 3.43 (1H, broad) 4.33 (2H, t, J=5.2 Hz), 4.62 (1H, d, J=8.0 Hz), 5.08 (2H, s), 5.31 (1H, m), 7.00 (1H, dd, J=1.2 Hz, 7.8 Hz), 7.12 (2H, m), 7.35 (5H, s), 8.25 (1H, dd, J=1.7 Hz, 7.8 Hz). ESIMS m/z=464 (MH$^+$).

N2-[(4-aminocyclohexyl)methyl]-4,5-dihydrobenzo[2,3]-oxepino[4,5-d][1,3]thiazol-2-amine: A solution of benzyl-N-{4-[(4,5-dihydrobenzo-[2,3]oxepino-[4,5-d][1,3]-thiazol-2-ylamino)methyl]cyclohexyl}carbamate (3.00 g, 6.47 mmol) in glacial acetic acid (50 ml) and conc. HCl (20 ml) was heated to a gentle reflux for 45 minutes. The solvent was removed on the rotor-vap with gentle heating and the residue diluted with water (150 ml). The resulting solution was made basic with NaOH (pH~11). EtOAc (200 ml) was added and the solution was shaken vigorously. The phases were separated and the aqueous phase was extracted with EtOAc. The combined extract was washed with water and evaporated to yield 2.30 g of a brown viscous oil. The oil was taken up into 40 ml EtOAc and 5 ml 4N HCl in dioxane was added. The resulting dihydrochloride salt was obtained by filtration and washed with EtOAc and ether. Upon drying, 100% (2.6 g) of the salt was obtained as a tan solid: $^1$H-NMR (d$_4$-MeOH) δ 1.21 (2H, m), 1.43 (2H, m), 1.79 (1H, m), 1.99 (2H, m), 2.10 (2H, m), 3.09 (1H, m), 3.18 (2H, t, J=5.0 Hz), 3.35 (2H, d, J=6.7 Hz), 4.32 (2H, t, J=5.3 Hz), 7.12 (1H, dd, J=1.1, 8.0 Hz), 7.22 (1H, m), 7.33 (1H, m), 7.70 (1H, dd, J=1.3, 8.0 Hz). ESIMS m/z=330 (MH$^+$).

N1-{4-[(4,5-dihydrobenzo[2,3]oxepino[4,5-d][1,3]-thiazol-2-ylamino)methyl]cyclohexyl}acetamide: To a stirred solution of N2-[(4-aminocyclohexyl)methyl]-4,5-dihydrobenzo[2,3]oxepino[4,5-d][1,3]thiazol-2-amine (0.600 g, 1.49 mmol) in anhydrous pyridine (3 ml) and diisopropylethylamine was added acetyl chloride (0.130 ml, 1.83 mmol) dropwise. The solution was stirred for 30 minutes at room temperature and then poured into water (60 ml). The mixture was extracted with EtOAc, and the organic phase evaporated to afford a residue that was chromatographed on silica-gel eluting with EtOAc to yield 72% (400 mg) of the desired product as a light yellow solid: m.p. 69–72° C. $^1$H-NMR (CDCl$_3$) δ 1.11 (4H, m), 1.60 (1H, broad), 1.73 (1H, broad), 1.83 (2H, m), 1.95 (3H, s), 2.05 (2H, m), 3.14 (4H, m), 3.73 (1H, broad), 4.33 (2H, t, J=4.9 Hz), 5.30 (1H, broad), 7.00 (1H, dd, J=0.9 Hz, 7.7 Hz), 7.12 (2H, m), 8.24 (1H, dd, J=0.9 Hz, 7.8 Hz). ESIMS m/z=372 (MH$^+$).

N2-{[4-(Ethylamino)cyclohexyl]methyl}-4,5-dihydrobenzo-[2,3]oxepino[4,5-d][1,3]thiazol-2-amine: To a stirred solution of N1-{4-[(4,5-dihydrobenzo[2,3]oxepino[4,5-d][1,3]thiazol-2-ylamino)methyl]cyclohexyl}acetamide (0.380 g, 1.02 mmol) in anhydrous THF (4 ml) was added 1M BH$_3$ in THF (5.0 ml, 5.0 mmol). The solution was stirred at room temperature overnight. 4N HCl (12 ml) was added slowly and stirring continued for 15 minutes. The resulting solution was made basic (pH~9) with 2N NaOH. The cloudy solution was extracted with EtOAc and the organic layer washed with water. Removal of the solvent in vacuo, gave 69% (252 mg) of the product as a solid which was used without further purification: $^1$H-NMR (CDCl$_3$) δ 0.96 (4H, m), 1.08 (3H, t, J=7.1 Hz), 1.47 (1H, m), 1.76 (2H, d, J=12.1 Hz), 1.90 (2H, m), 2.37 (2H, m), 2.63 (2H, q, J=7.0 Hz), 3.05 (2H, t, J=5.7 Hz), 3.11 (2H, t, J=5.1 Hz), 4.28 (2H, t, J=5.2 Hz), 5.73 (1H, broad t), 6.96 (1H, dd, J=0.9 Hz, 7.7 Hz), 7.10 (2H, m), 8.22 (1H, dd, J=1.3 Hz, 7.6 Hz); 358 (ESMS, MH$^+$).

N-{4-[(4,5-Dihydrobenzo[2,3]oxepino[4,5-d][1,3]thiazol-2-ylamino)methyl]cyclohexyl}-N-ethylformamide: To a stirred solution of N2-{[4-(ethylamino)cyclohexyl]methyl}-4,5-dihydrobenzo[2,3]-oxepino-[4,5-d][1,3]-thiazol-2-amine (0.252 g, 0.70 mmol) in anhydrous THF (3.5 ml) was added 1H-benzotriazole-1-carboxaldehyde (0.112 g, 0.76 mmol). The solution was stirred at room temperature for 1 hour and then poured into 2N NaOH (60 ml). The mixture was extracted with EtOAc and evaporated to afford 268 mg of the desired crude product as a solid. The product was chromatographed on silica-gel eluting with 70% EtOAc/30% hexane to yield 56% (150 mg) of a white solid. The compound was dissolved in chloroform and converted to its HCl salt by addition of 1N HCl in ether. The solvents were removed in vacuo and the residue triturated with hexane/ether and filtered to afford the product as a white solid: m.p. 210–213° C.; $^1$H-NMR (CDCl$_3$) δ 1.13 (4H, m), 1.59 (2H, m), 1.88 (6H, m), 3.17 (4H, m), 3.24 (3H, m), 4.32 (2H, t), 5.40 (1H, broad), 7.00 (1H, d), 7.13 (2H, m), 8.09 (0.4H, s), 8.12 (0.6H, s), 8.23 (1H, dd); 386 (ESMS, MH$^+$).

EXAMPLE 88

N-(4-[(4,5-Dihydrobenzo[2,3]oxepino[4,5-d][1,3]thiazol-2-ylamino)methyl]cyclohexyl}-N-propylformamide:

N1-{4-[(4,5-Dihydrobenzo[2,3]oxepino[4,5-d][1,3]thiazol-2-ylamino)methyl]cyclohexyl}propanamide: To a stirred solution of N2-[(4-aminocyclohexyl)methyl]-4,5-dihydrobenzo[2,3]oxepino[4,5-d][1,3]thiazol-2-amine (0.600 g, 1.49 mmol) in anhydrous pyridine (3 ml) and diisopropylethylamine (3 ml) was added propionyl chloride (0.155 ml, 1.78 mmol) dropwise. The solution was stirred for 1 hour at room temperature and poured into water (60 ml). The solution was extracted with EtOAc and the solvent removed in vacuo to yield a viscous golden oil. The oil was chromatographed on silica-gel eluting with 70% EtOAc/30% hexane to yield 74% (425 mg) of an orange solid: m.p. 70–73° C. $^1$H-NMR (CDCl$_3$) δ 1.10 (6H, m), 1.60 (1H, broad), 1.83 (3H, m), 2.00 (3H, m), 2.17 (2H, q, J=7.6 Hz), 3.13 (4H, q, J=5.1 Hz), 3.73 (1H, broad), 4.32 (2H, t, J=5.3 Hz), 5.32 (1H, broad), 7.00 (1H, dd, J=6.4 Hz). ESIMS m/z=386 (MH$^+$).

N2-{[4-(propylamino)cyclohexyl]methyl}-4,5-dihydrobenzo-[2,3]oxepino[4,5-d][1,3]thiazol-2-amine: To a stirred solution of N1-{4-[(4,5-dihydrobenzo[2,3]oxepino[4,5-d][1,3]thiazol-2-ylamino)methyl] cyclohexyl}propanamide (0.405 g, 1.05 mmol) in anhydrous THF (4 ml) was added 1M BH$_3$ in THF (5.5 ml, 5.5 mmol). The solution was stirred at room temperature for 52 hours. 4N HCl (12 ml) was added slowly and stirring continued for 30 minutes thereafter. The solution was poured into 2N NaOH (60 ml) and extracted with EtOAc. The extract was washed with 10% brine, separated and evaporated to yield 77% (300 mg) of the amine as a viscous golden oil: $^1$H-NMR (CDCl$_3$) δ 0.88 (3H, t), 1.06 (2H, m), 1.38 (2H, m), 1.49 (2H, m), 1.80 (6H, m), 2.40 (1H, m), 2.58 (2H, t), 3.15 (2H, m), 3.63 (2H, t), 4.30 (2H, t), 5.12 (1H, m), 6.98 (1H, d), 7.11 (2H, m), 8.23 (1H, dd); 400 (ESMS, MH$^+$).

N-{4-[(4,5-Dihydrobenzo[2,3]oxepino[4,5-d][1,3]thiazol-2-ylamino)methyl]cyclohexyl}-N-propylformamide: To a stirred solution of N2-{[4-(propylamino)cyclohexyl]methyl}-4,5-dihydrobenzo[2,3]-oxepino[4,5-d][1,3]thiazol-2-amine (0.300 g, 0.81 mmol) in anhydrous THF (4 ml) was added 1H-benzotriazole-1-carboxaldehyde (0.126 g, 0.86 mmol). The solution was stirred for 1 hour at room temperature and poured into 2N NaOH (50 ml). The mixture was extracted with EtOAc (60 ml). The extract was evaporated to yield 320 mg of the crude product as a viscous yellow oil. The oil was chromatographed on silica-gel eluting with 70% EtOAc/30% hexane to afford 125 mg of the product as a colorless oil. The oil was dissolved in chloroform and converted to its HCl salt with 1N HCl in Et$_2$O. Upon evaporation of the solvent, a solid was obtained. The solid was triturated with EtOAc, filtered and washed with hexane to give 25% (87 mg) of the desired product as a white solid: m.p. (HCl salt) 195–197° C.; $^1$H-NMR (CDCl$_3$) δ 0.89 (3H, t), 1.05 (2H, p), 1.50 (5H, m), 1.79 (4H, m), 3.10 (6H, m), 4.30 (2H, m), 5.93 (2H, m), 7.06 (3H, m), 8.02 (0.4H, s), 8.10 (0.6H, s), 8.22 (1H, dd); 400 (ESMS, MH$^+$).

EXAMPLE 89

N1-{4-[(9-fluoro-5,6-dihydro-4H-benzo[6,7]cyclohepta[d][1,3]thiazol-2-yl)amino]benzyl}-2-methoxyacetamide: To a stirred solution of N2-[4-(aminomethyl)phenyl]-9-fluoro-5,6-dihydro-4H-benzo[6,7]cyclohepta[d][1,3]thiazol-2-amine (See example 90) (1.50 g, 3.64 mmol) in anhydrous pyridine (10 ml) and diisopropylethylamine (5.0 ml) was added methoxyacetyl chloride (0.40 ml, 4.38 mmol) dropwise. The solution was stirred overnight, poured into water (200 ml) and extracted with EtOAc (200 ml). The extract was evaporated to yield 1.8 g of a viscous golden oil. The oil was chromatographed on silica-gel eluting with EtOAc to yield 80% (1.2 g) of the desired product as a foam. The product was converted to its HCl salt in chloroform using 1M HCl in Et$_2$O: m.p. (HCl salt) 175–178° C.; $^1$H-NMR (CDCl$_3$) δ 2.15 (2H, m), 2.86 (4H, m), 3.42 (3H, s), 3.96 (2H, s), 4.50 (2H, d, J=6.1 Hz), 7.00 (1H, t), 7.18–7.40 (7H, m), 7.61 (1H, dd, J=2.5 Hz, 9.5 Hz); 412 (ESMS, MH$^+$).

EXAMPLE 90

N-{4-[(9-Fluoro-5,6-dihydro-4H-benzo[6,7]cyclohepta[d][1,3]thiazol-2-yl)amino]benzyl}methanesulfonamide:

N2-[4-(Aminomethyl)phenyl]-9-fluoro-5,6-dihydro-4H-benzo[6,7]cyclohepta[d][1,3]thiazol-2-amine:

6-Bromo-3-fluoro-6,7,8,9-tetrahydro-5H-benzo[a]cyclohepten-5-one: To a stirred solution of 8-fluoro-1-benzosuberone (20.00 g, 112.2 mmol) in glacial acetic acid (125 ml) was added bromine (5.8 ml, 112.6 mmol) dropwise. Once the addition was complete, the solution was poured into water (400 ml) and extracted with EtOAc (500 ml). The extract was separated and washed with water (500 ml). The organic layer was dried over MgSO$_4$, filtered and evaporated to yield 100% (28.9 g) of the desired product as a viscous oil: $^1$H-NMR (CDCl$_3$) δ 2.00 (2H, m), 2.33 (2H, m), 2.84 (1H, m), 3.00 (1H, m), 4.83 (1H, m), 7.13 (2H, m), 7.29 (1H, dd).

tert-Butyl N-(4-Aminobenzyl)carbamate: To a stirred solution of 4-amino-benzylamine (7.5 g, 61.39 mmol) in anhydrous THF (100 ml) under N$_2$ was added di-t-butyl dicarbonate (13.5 g, 61.9 mmol) in portions. The solution was stirred at room temperature under N$_2$ for 90 minutes. The solvent was removed in vacuo to yield 100% (13.7 g) of the Boc-protected amine as a white solid: m.p. 70–72° C.; $^1$H-NMR (CDCl$_3$) δ 1.43 (9H, s), 3.62 (2H, broad), 4.18 (2H, d), 4.77 (1H, broad), 6.63 (2H, d), 7.06 (2H, d).

tert-Butyl N-(4-{[(Benzoylamino)carbothioyl]amino}benzyl)-carbamate: To a stirred solution of tert-butyl N-(4-aminobenzyl)carbamate (6.00 g, 27.0 mmol) in anhydrous THF (50 ml) was added benzoylisothiocyanate (4.43 g, 27.0 mmol). The solution was stirred for 2 hours and the solvent removed in vacuo to yield 100% (10.4 g) of the protected thiourea as a yellow solid: m.p. 161–163° C.; $^1$H-NMR (CDCl$_3$) δ 1.45 (9H, s), 4.33 (2H, d), 4.85 (1H, broad), 7.34 (2H, d), 7.60 (5H, m), 7.90 (2H, d), 9.13 (1H, s), 12.58 (1H, s); 386 (ESMS, MH$^+$).

tert-Butyl N-{4-[(Aminocarbothioyl)amino]benzyl}carbamate: To a stirred near solution of tert-butyl N-(4-{[(benzoylamino)carbothioyl]amino}benzyl) carbamate (10.4 g, 27.0 mmol) in MeOH (150 ml) was added a solution of K$_2$CO$_3$ (8.5 g, 61.5 mmol) in 15 ml water. The solution was stirred at room temperature for 24 hours and filtered to remove a white precipitate. The filtrate was evaporated in vacuo to yield 100% (7.6 g) of the desired product as an off-white solid.

tert-Butyl N-{4-[(9-Fluoro-5,6-dihydro-4H-benzo[6,7]cyclohepta[d][1,3]thiazol-2-yl)amino]benzyl}carbamate: A solution containing tert-butyl N-{4-[(aminocarbothioyl)-amino]benzyl}carbamate (7.60 g, 27.0 mmol), 6-bromo-3-fluoro-6,7,8,9-tetrahydro-5H-benzo[a]cyclohepten-5-one (6.95 g, 27.0 mmol) and diisopropylethylamine (5.0 ml) in EtOH (60 ml) was heated at reflux for 2.5 hours. The solvent was removed in vacuo and the residue dissolved in EtOAc (125 ml). The resulting solution was filtered to remove the insoluble (i-pr)$_2$NEt·HBr. The filtrate was transferred to a 250 ml round bottom flask and 4N HCl in dioxane (35 ml) was added with stirring. The solution was stirred for 90 minutes and then filtered to collect the hydrochloride salt. The solid was washed with EtOAc and then with Et$_2$O. Upon drying, 86% (11.1 g) of the Boc-protected amine hydrochloride was obtained as a pale yellow solid: $^1$H-NMR (d$_4$-MeOH) δ 1.43 (9H, s), 2.18 (2H, m), 2.80 (4H, m), 4.25 (2H, s), 7.12 (1H, dt), 7.33 (2H, m), 7.43 (4H, s).

N2-[4-(aminomethyl)phenyl]-9-fluoro-5,6-dihydro-4H-benzo[6,7]cyclohepta[d][1,3]thiazol-2-amine: To a stirred near solution of tert-butyl [4-(4H-chromeno[4,3-d][1,3]thiazol-2-yiamino)cyclohexyl]methylcarbamate (11.1 g, 23.3 mmol) in MeOH (150 ml) was added 4N HCl in dioxane (40 ml). The solution was brought to a brief gentle reflux and the solvent then removed in vacuo. The resulting solid was re-suspended in Et$_2$O, filtered and dried to yield 90% (9.25 g) of the desired di-hydrochloride salt as a white solid: m.p. 236–239° C.; $^1$H-NMR (CDCl$_3$) δ 1.75 (2H, broad), 2.06 (2H, m), 2.77 (2H, m), 2.83 (2H, t), 3.79 (2H, s), 6.82 (1H, t), 7.04 (1H, m), 7.22 (4H, m), 7.79 (1H, dd), 8.8 (1H, broad); 340 (ESMS, MH$^+$).

To a stirred solution of N2-[4-(aminomethyl)phenyl]-9-fluoro-5,6-dihydro-4H-benzo[6,7]cyclohepta[d][1,3]thiazol-2-amine (1.50 g, 3.64 mmol) in anhydrous pyridine (10 ml) and diisopropylethylamine (5.0 ml) was added methanesulfonyl chloride (0.38 ml, 4.91 mmol) dropwise. The solution was stirred at room temperature overnight, poured into water (250 ml) and extracted with EtOAc. The extract was evaporated to yield 1.7 g of the crude product as a viscous orange oil. The oil was chromatographed on silica-gel eluting with EtOAc (R$_f$ of product ~0.9) to yield 66% (1.0 g) of the desired product as a solid. The solid was triturated with Et$_2$O/hexane (1:1) and filtered to give 0.93 g of the product as a pale yellow solid: m.p. 148–150° C.; $^1$H-NMR (CDCl$_3$) δ 2.13 (2H, m), 2.79 (2H, m), 2.89 (3H, s), 2.91 (2H, m), 4.24 (2H, d, J=4.3 Hz), 5.06 (1H, m), 6.88 (1H, t), 7.13 (1H, t), 7.30 (4H, m), 7.48 (1H, m), 7.72 (1H, dd, J=2.7 Hz, 10.6 Hz); 418 (ESMS, MH$^+$).

II. Synthetic Methods for General Structures

The examples described in Section I are merely illustrative of the methods used to synthesize tricyclic compounds.

Further compounds may be obtained utilizing methods shown in Schemes 1–6. The substituents in Schemes 1–6 are described in the Detailed Description.

It may be necessary to incorporate protection and deprotection strategies for substituents such as amino, amido, carboxylic acid, and hydroxyl groups in the synthetic methods described above to form tricyclic derivatives. Methods for protection and deprotection of such groups are well-known in the art, and may be found, for example in Green, T. W. and Wuts, P. G. M. (1991) *Protection Groups in Organic Synthesis*, $2^{nd}$ Edition John Wiley & Sons, New York.

III. Oral Compositions

As a specific embodiment of an oral composition of a compound of this invention , 100 mg of one of the compounds described herein is formulated with sufficient finely divided lactose to provide a total amount of 580 to 590 mg to fill a size O hard gel capsule.

IV. Pharmacological Evaluation of Compounds at Cloned Neuropeptide Y-type Receptors The pharmacological properties of the compounds of the present invention were evaluated at one or more of the cloned human neuropeptide Y-type receptors Y1, Y2, Y4, and Y5, using protocols described below.

Cell Culture

COS-7 cells were grown on 150 mm plates in D-MEM with supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of COS-7 cells were trypsinized and split 1:6 every 3–4 days. Human embryonic kidney 293 cells were grown on 150 mm plates in D-MEM with supplements (minimal essential medium) with Hanks' salts and supplements (Dulbecco's Modified Eagle Medium with 10% bovine calf serum, 4 mM glutamine, 100 units/ml penicillin/100 μg/ml streptomycin) at 37° C., 5% $CO_2$. Stock plates of 293 cells were trypsinized and split 1:6 every 3–4 days. Mouse fibroblast LM(tk-) cells were grown on 150 mm plates in D-MEM with supplements (Dulbecco's Modified Eagle Medium with 10% bovine calf serum, 4 mM glutamine, 100 units/mL penicillin/100 μg/mL streptomycin) at 37° C., 5% $CO_2$. Stock plates of LM(tk-) cells were trypsinized and split 1:10 every 3–4 days.

LM(tk-) cells stably transfected with the human Y5 receptor were routinely converted from an adherent monolayer to a viable suspension. Adherent cells were harvested with trypsin at the point of confluence, resuspended in a minimal volume of complete DMEM for a cell count, and further diluted to a concentration of $10^6$ cells/ml in suspension media (10% bovine calf serum, 10% 10x Medium 199 (Gibco), 9 mM $NaHCO_3$, 25 mM glucose, 2 mM L-glutamine, 100 units/ml penicillin/100 μg/ml streptomycin, and 0.05% methyl cellulose). The cell suspension was maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/ml) followed by incubation at 37° C., 5% $CO_2$ for 24 hours. Cells prepared in this manner yielded a robust and reliable NPY-dependent response in cAMP radio-immunoassays as further described hereinbelow.

Mouse embryonic fibroblast NIH-3T3 cells were grown on 150 mm plates in Dulbecco's Modified Eagle Medium (DMEM) with supplements (10% bovine calf serum, 4 mM glutamine, 100 units/ml penicillin/100 μg/ml streptomycin) at 37° C., 5% $CO_2$. Stock plates of NIH-3T3 cells were trypsinized and split 1:15 every 3–4 days. Sf9 and Sf21 cells were grown in monolayers on 150 mm tissue culture dishes in TMN-FH media supplemented with 10% fetal calf serum, at 27° C., no $CO_2$. High Five insect cells were grown on 150 mm tissue culture dishes in Ex-Cell 400™ medium supplemented with L-Glutamine, also at 27° C., no $CO_2$.

Transient Transfection

All receptor subtypes studied (human and rat Y1, human and rat Y2, human and rat Y4, human and rat Y5) were transiently transfected into COS-7 cells by the DEAE-dextran method, using 1 μg of DNA/$10^6$ cells (Cullen, 1987). The human Y1receptor was prepared using known methods (Larhammar, et al., 1992).

Stable Transfection

Human Y1, human Y2, and rat Y5 receptors were co-transfected with a G-418 resistant gene into the human embryonic kidney 293 cell line by a calcium phosphate transfection method (Cullen, 1987). Stably transfected cells were selected with G-418. Human Y4 and human Y5 receptors were similarly transfected into mouse fibroblast LM(tk-) cells and NIH-3T3 cells.

Binding of the compounds of the present invention to human Y1, Y2, Y4, and Y5 receptors was evaluated using stably transfected 293 or LM(tk-) cells as described above. Stably transfected cell lines which may be used for binding assays include, for example, for the human Y1 receptor, 293-hY1-5 (deposited Jun. 4, 1996, under ATCC Accession No. CRL-12121), for the human Y2 receptor, 293-hY2-10 (deposited Jan. 27, 1994, under ATCC Accession No. CRL-11537), for the human Y4 receptor, L-hY4-3 (deposited Jan. 11, 1995, under ATCC Accession No. CRL-11779), and for human Y5 receptor, L-hY5-7 (deposited Nov. 15, 1995, under ATCC Accession No. CRL-11995). These cell lines were deposited with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure.

Membrane Harvest

Membranes were harvested from COS-7 cells 48 hours after transient transfection. Adherent cells were washed twice in ice-cold phosphate buffered saline (138 mM NaCl, 8.1 mM $Na_2HPO_4$, 2.5 mM KCl, 1.2 mM $KH_2PO_4$, 0.9 mM $CaCl_2$, 0.5 mM $MgCl_2$, pH 7.4) and lysed by sonication in ice-cold sonication buffer (20 mM Tris-HCl, 5 mM EDTA, pH 7.7). Large particles and debris were cleared by low speed centrifugation (200×g, 5 min, 4° C.). Membranes were collected from the supernatant fraction by centrifugation (32,000×g, 18 min, 4° C.), washed with ice-cold hypotonic buffer, and collected again by centrifugation (32,000×g, 18 min, 4° C.). The final membrane pellet was resuspended by sonication into a small volume of ice-cold binding buffer (~1 ml for every 5 plates: 10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (Bradford, 1976) using Bio-Rad Reagent, with bovine serum albumin as a standard. Membranes were held on ice for up to one hour and used fresh, or flash-frozen and stored in liquid nitrogen.

Membranes were prepared similarly from 293, LM(tk-), and NIH-3T3 cells. To prepare membranes from baculovirus infected cells, $2\times10^7$ Sf21 cells were grown in 150 mm tissue culture dishes and infected with a high-titer stock of hY5BB3. Cells were incubated for 2–4 days at 27° C., no $CO_2$ before harvesting and membrane preparation as described above.

Membranes were prepared similarly from dissected rat hypothalamus. Frozen hypothalami were homogenized for 20 seconds in ice-cold sonication buffer with the narrow probe of a Virtishear homogenizer at 1000 rpm (Virtis, Gardiner, N.Y.). Large particles and debris were cleared by centrifugation (200×g, 5 min, 4° C.) and the supernatant fraction was reserved on ice. Membranes were further extracted from the pellet by repeating the homogenization and centrifugation procedure two more times. The supernatant fractions were pooled and subjected to high speed centrifugation (100,000×g, 20 min. 4° C.). The final membrane pellet was resuspended by gentle homogenization into a small volume of ice-cold binding buffer (1 mL/gram wet weight tissue) and held on ice for up to one hour, or flash-frozen and stored in liquid nitrogen.

Radioligand Binding to Membrane Suspensions

Membrane suspensions were diluted in binding buffer supplemented with 0.1% bovine serum albumin to yield an optimal membrane protein concentration so that $^{125}$I-PYY (or alternative radioligand such as $^{125}$I-NPY, $^{125}$I-PYY$_{3-36}$, or $^{125}$I-[Leu$^{31}$Pro$^{34}$]PYY) bound by membranes in the assay was less than 10% of $^{125}$I-PYY (or alternative radioligand) delivered to the sample (100,000 dpm/sample=0.08 nM for competition binding assays). $^{125}$I-PPY (or alternative radioligand) and peptide competitors were also diluted to desired concentrations in supplemented binding buffer. Individual samples were then prepared in 96-well polypropylene microtiter plates by mixing $^{125}$I-PYY (25 μL) (or alternative radioligand), competing peptides or supplemented binding buffer (25 μL), and finally, membrane suspensions (200 μL). Samples were incubated in a 30° C. water bath with constant shaking for 120 min. Incubations were terminated by filtration over Whatman GF/C filters (pre-coated with 1% polyethyleneimine and air-dried before use), followed by washing with 5 mL of ice-cold binding buffer. Filter-trapped membranes were impregnated with MeltiLex solid scintillant (Wallac, Turku, Finland) and counted for $^{125}$I in a Wallac Beta-Plate Reader. Alternatively, incubations were carried out in GF/C filter plates (pre-coated with 1% polyethyleneimine and air-dried before use), followed by vacuum filtration and three washes of 300 μL of ice-cold binding buffer. 50 μL of UltimaGold (Packard) scintillant were added and counted for $^{125}$I in a Wallac MicroBeta Trilux. Non-specific binding was defined by 300 nM human NPY for all receptors except the Y4 subtypes; 100 nM human PP was used for the human Y4 and 100 nM rat PP for the rat Y4. Specific binding in time course and competition studies was typically 80%; most non-specific binding was associated with the filter. Binding data were analyzed using nonlinear regression and statistical techniques available in the GraphPAD Prism package (San Diego, Calif.).

Functional Assay: Radioimmunoassay of cAMP

Stably transfected cells were seeded into 96-well microtiter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1% bovine serum albumin plus 5 mM theophylline and pre-equilibrated in the same solution for 20 min at 37° C. in 5% $CO_2$. Cells were then incubated 5 min with 10 μM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microtiter plate (Millipore, Bedford, Mass.). Filters were punched and counted for $^{125}$I in a Packard gamma counter. Binding data were analyzed using nonlinear regression and statistical techniques available in the GraphPAD Prism package (San Diego, Calif.).

Functional Assay: Intracellular Calcium Mobilization

The intracellular free calcium concentration was measured by microspectroflourometry using the fluorescent indicator dye Fura-2/AM. Stably transfected cells were seeded onto a 35 mm culture dish containing a glass coverslip insert. Cells were washed with HBS and loaded with 100 μl of Fura-2/AM (10 μM) for 20 to 40 min. After washing with HBS to remove the Fura-2/AM solution, cells were equilibrated in HBS for 10 to 20 min. Cells were then visualized under the 40× objective of a Leitz Fluovert FS microscope and fluorescence emission was determined at 510 nM with excitation wave lengths alternating between 340 nM and 380 nM. Raw fluorescence data were converted to calcium concentrations using standard calcium concentration curves and software analysis techniques.

Materials

Cell culture media and supplements were from Specialty Media (Lavallette, N.J.). Cell culture plates (150 mm and 96-well microtiter) were from Corning (Corning, N.Y.). Sf9, Sf21, and High Five insect cells, as well as the baculovirus transfer plasmid, pBlueBacIII™, were purchased from Invitrogen (San Diego, Calif.). TMN-FH insect medium complemented with 10% fetal calf serum, and the baculovirus DNA, BaculoGold™, was obtained from Pharmingen (San Diego, Calif.). Ex-Cell 400™ medium with L-Glutamine was purchased from JRH Scientific. Polypropylene 96-well microtiter plates were from Co-star (Cambridge, Mass.). All radioligands were from New England Nuclear (Boston, Mass.). Commercially available NPY and related peptide analogs were either from Bachem Calif. (Torrance, Calif.) or Peninsula (Belmont, Calif.); [D-Trp$^{32}$]NPY and PP C-terminal fragments were synthesized by custom order from Chiron Mimotopes Peptide Systems (San Diego, Calif.). Bio-Rad Reagent was from Bio-Rad (Hercules, Calif.). Bovine serum albumin (ultra-fat free, A-7511) was from Sigma (St. Louis. Mo.). All other materials were reagent grade.

Radioligand Binding Assay Results

The compounds described above were assayed using cloned human NPY receptors. The preferred compounds were found to be selective NPY (Y5) antagonists. The binding affinities of several compounds for NPY (Y5) are illustrated in Table 1.

| EXAMPLE No. | STRUCTURE | $K_i$, nM hNPY-5 | $K_i$, nM hNPY-1,2,4 |
|---|---|---|---|
| 1 | 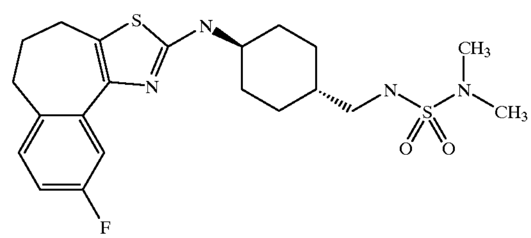 | 2.1 | >10000 |
| 2 | 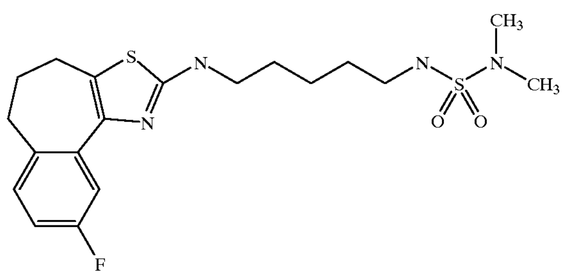 | 1.6 | |
| 3 | 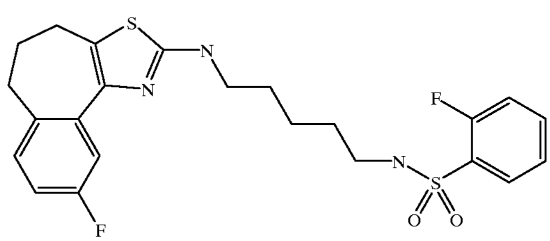 | 4.5 | >10000 |
| 4 | 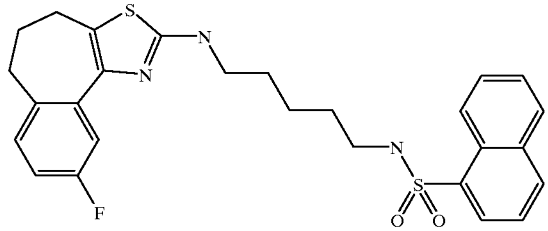 | 19.5 | >10000 |
| 5 | 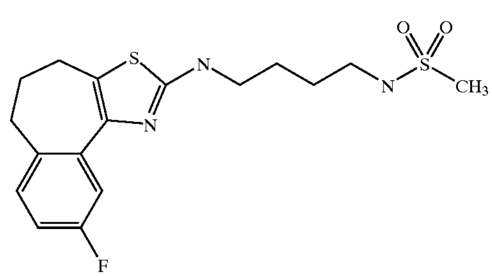 | 19.8 | >10000 |

-continued

| EXAMPLE No. | STRUCTURE | $K_i$, nM hNPY-5 | $K_i$, nM hNPY-1,2,4 |
|---|---|---|---|
| 6 | 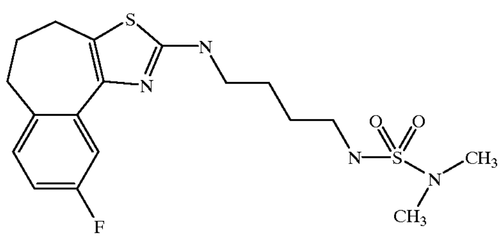 | 3.1 | |
| 7 | 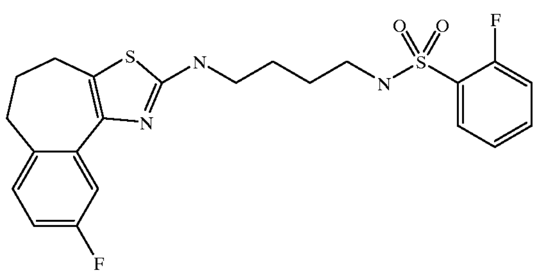 | 23 | >10000 |
| 8 | 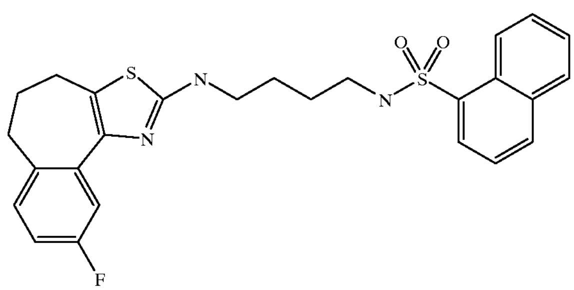 | 94 | |
| 9 | 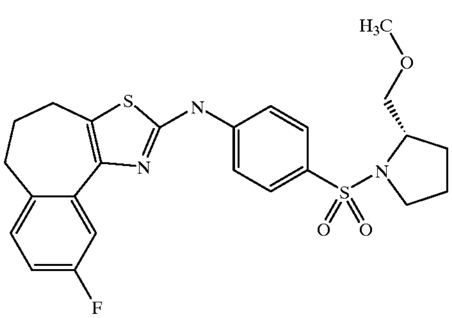 | 15.4 | >10000 |
| 10 | 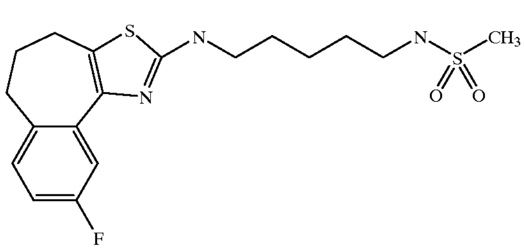 | 2.4 | >10000 |

-continued

| EXAMPLE No. | STRUCTURE | $K_i$, nM hNPY-5 | $K_i$, nM hNPY-1,2,4 |
|---|---|---|---|
| 11 | 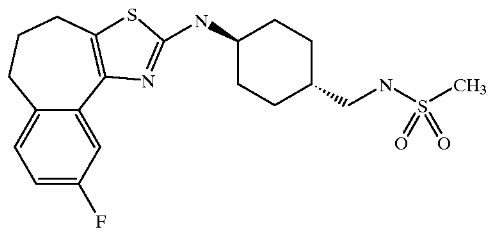 | 6.4 | >10000 |
| 12 | 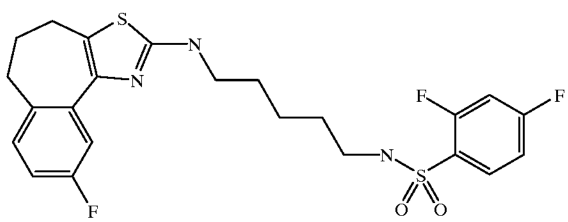 | 6.1 | >10000 |
| 13 | 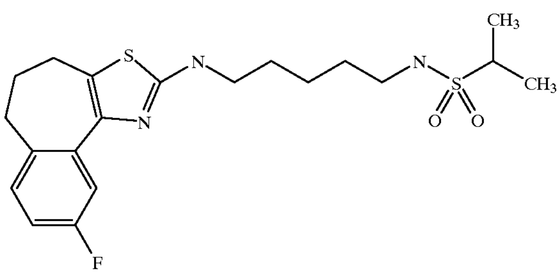 | 132 | |
| 14 | 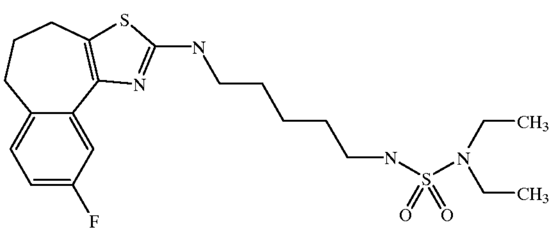 | 2.1 | >10000 |
| 15 | 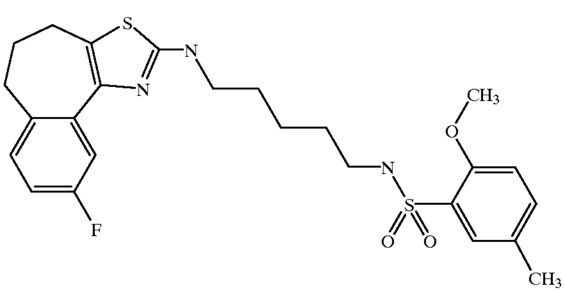 | 3.2 | |
| 16 | 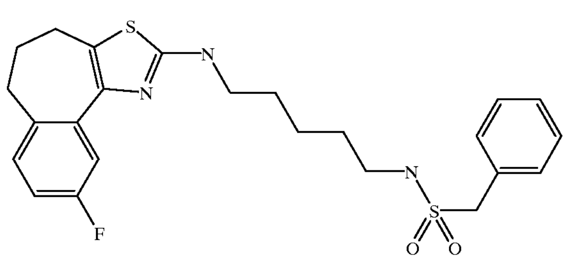 | 4.7 | >10000 |

-continued

| EXAMPLE No. | STRUCTURE | $K_i$, nM hNPY-5 | $K_i$, nM hNPY-1,2,4 |
|---|---|---|---|
| 17 | 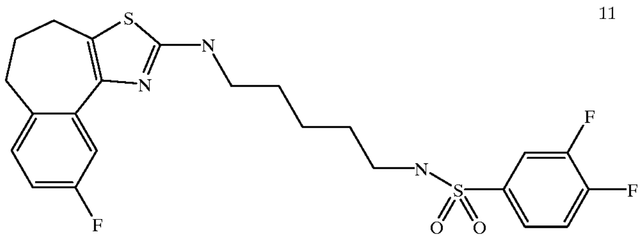 | 11 | >10000 |
| 18 | 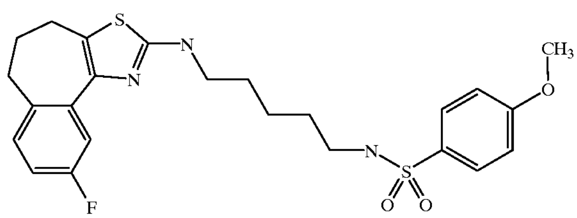 | 7.1 | >10000 |
| 19 | 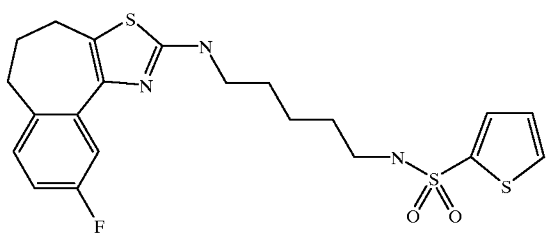 | 5 | >10000 |
| 20 | 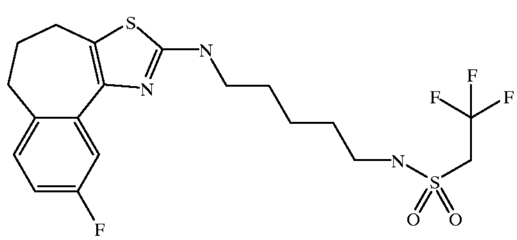 | 5.8 | >10000 |
| 21 | 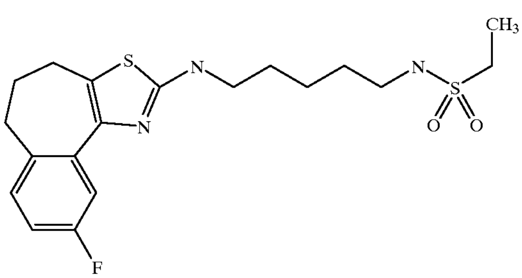 | 2.5 | >10000 |
| 22 | 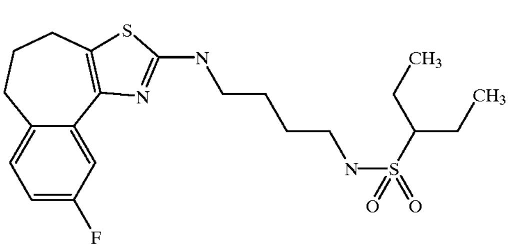 | 2.9 | >10000 |

-continued

| EXAMPLE No. | STRUCTURE | $K_i$, nM hNPY-5 | $K_i$, nM hNPY-1,2,4 |
|---|---|---|---|
| 23 | 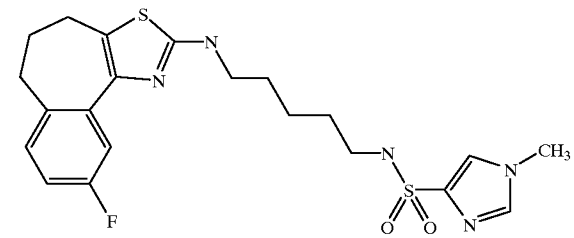 | 15.5 | >10000 |
| 24 | 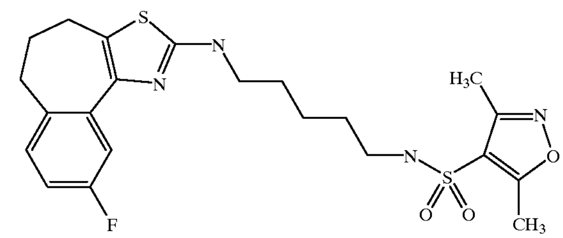 | 3.5 | >10000 |
| 25 | 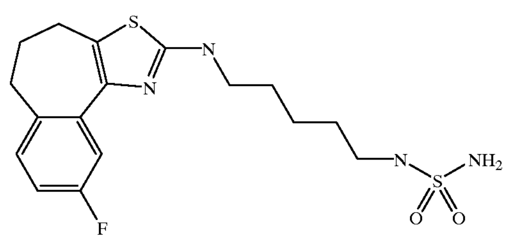 | 2.9 | >10000 |
| 26 | 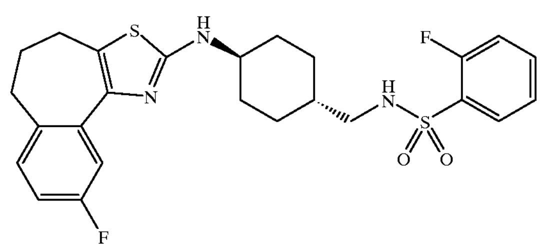 | 13.1 | >10000 |
| 27 | 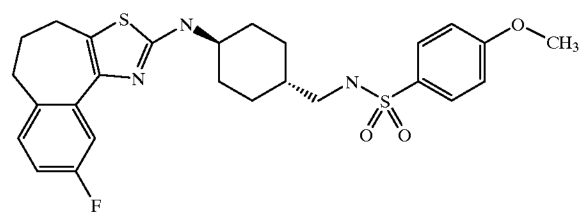 | 9.2 | >10000 |
| 28 | 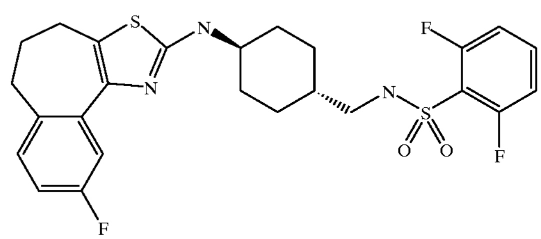 | 4 | >10000 |

-continued

| EXAMPLE No. | STRUCTURE | $K_i$, nM hNPY-5 | $K_i$, nM hNPY-1,2,4 |
|---|---|---|---|
| 29 | 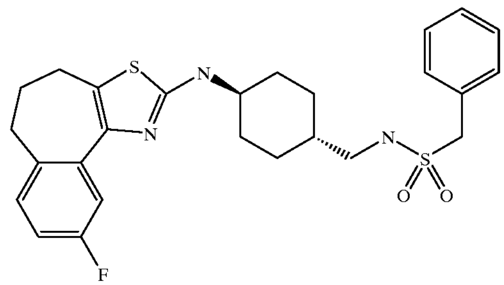 | 10.3 | >10000 |
| 30 | 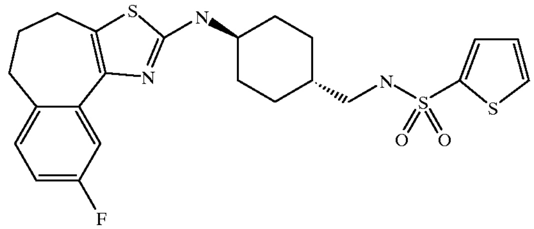 | 4.2 | >10000 |
| 31 | 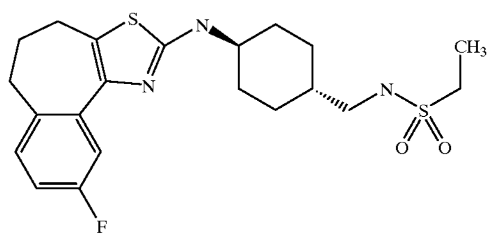 | 3.9 | >10000 |
| 32 | 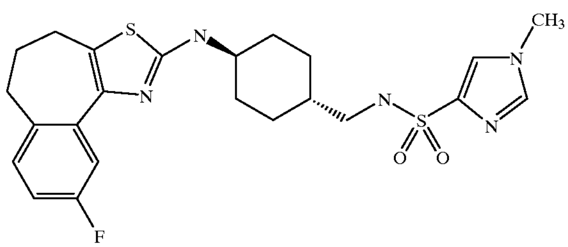 | 2.9 | >10000 |
| 33 | 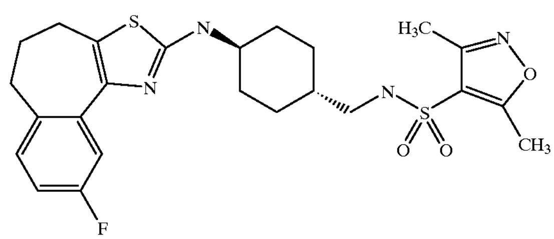 | 6.8 | >10000 |
| 34 | 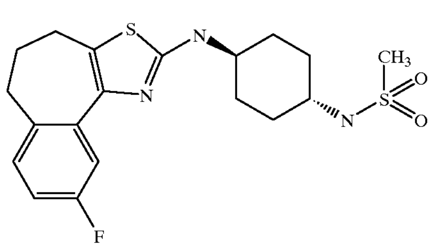 | 34 | |

-continued

| EXAMPLE No. | STRUCTURE | $K_i$, nM hNPY-5 | $K_i$, nM hNPY-1,2,4 |
|---|---|---|---|
| 35 | 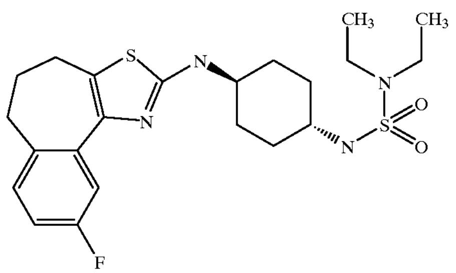 | 6.5 | >10000 |
| 36 | 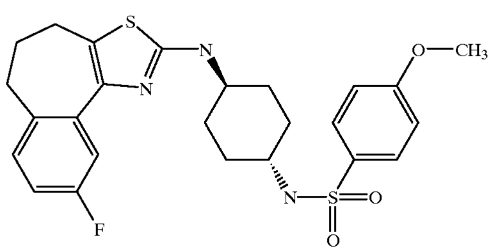 | 60 | |
| 37 | 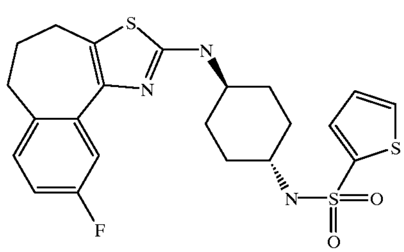 | 7.4 | >10000 |
| 38 | 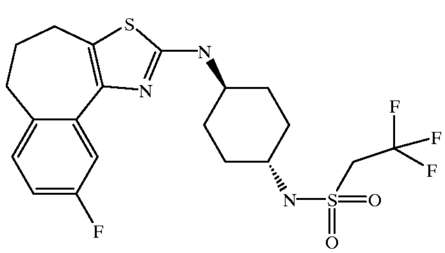 | 15.8 | >10000 |
| 39 | 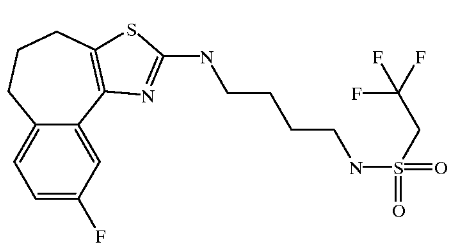 | 4.8 | >10000 |

-continued

| EXAMPLE No. | STRUCTURE | $K_i$, nM hNPY-5 | $K_i$, nM hNPY-1,2,4 |
|---|---|---|---|
| 40 | 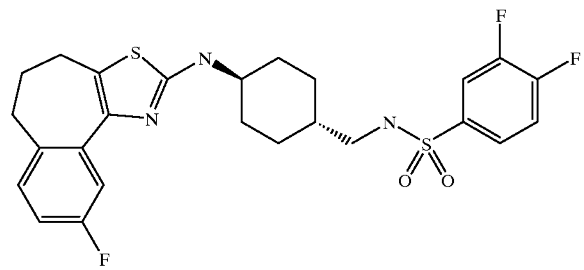 | 19.5 | >10000 |
| 41 | 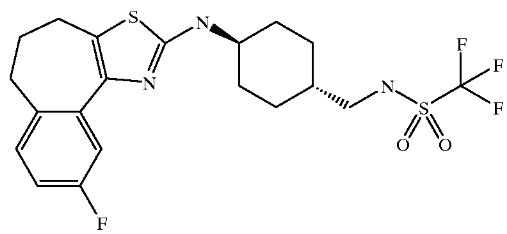 | 30 | |
| 42 | 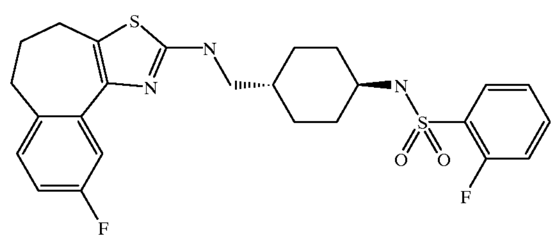 | 3.9 | >10000 |
| 43 | 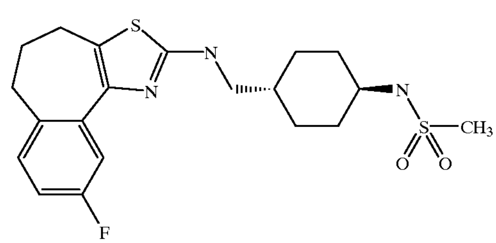 | 4.4 | >10000 |
| 44 | 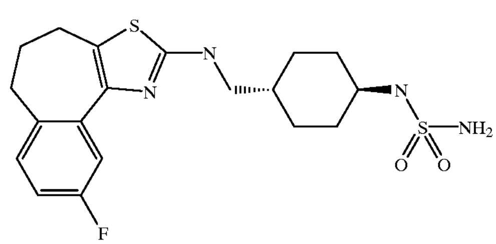 | 2.3 | >10000 |
| 45 | 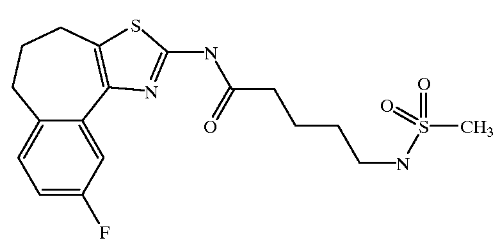 | 65 | >10000 |

-continued

| EXAMPLE No. | STRUCTURE | $K_i$, nM hNPY-5 | $K_i$, nM hNPY-1,2,4 |
|---|---|---|---|
| 46 | 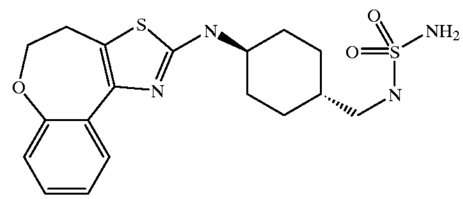 | 34 | >10000 |
| 47 | 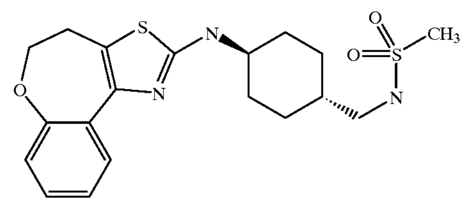 | 22 | >10000 |
| 48 | 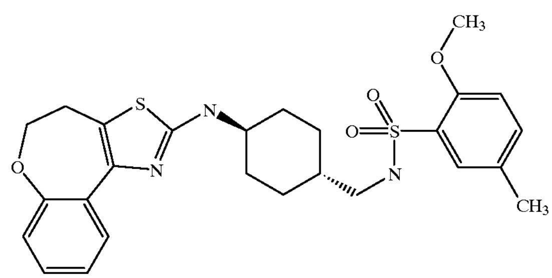 | 15.1 | >10000 |
| 49 | 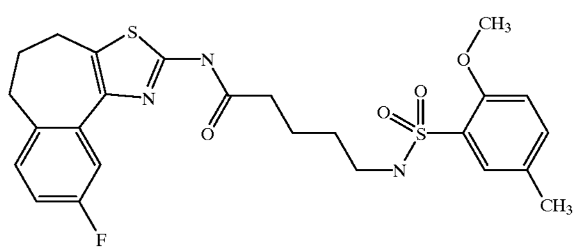 | 2.9 | |
| 50 | 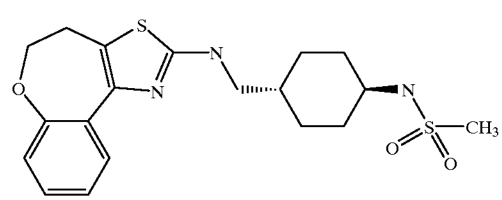 | 15.3 | |
| 51 | 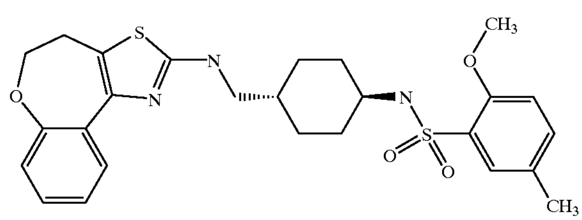 | 8.3 | |

-continued

| EXAMPLE No. | STRUCTURE | $K_i$, nM hNPY-5 | $K_i$, nM hNPY-1,2,4 |
|---|---|---|---|
| 52 | 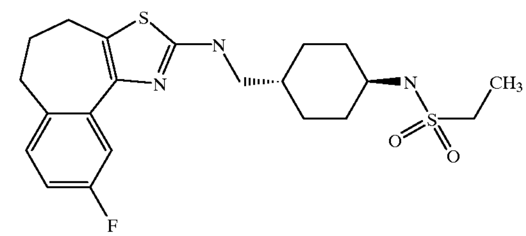 | 1.7 | |
| 53 | 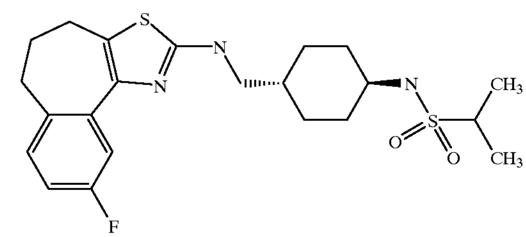 | 3.2 | |
| 54 | 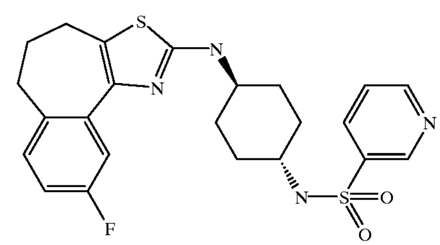 | 11.9 | >10000 |
| 55 | 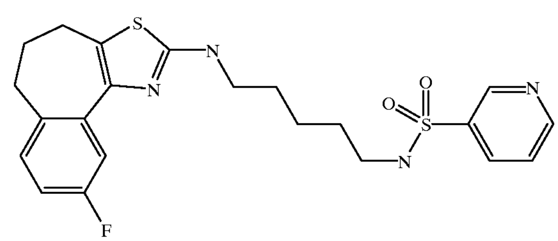 | 3.4 | |
| 56 | 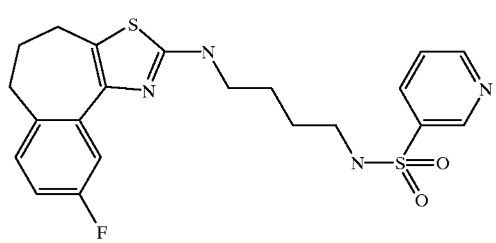 | 26 | |
| 57 | 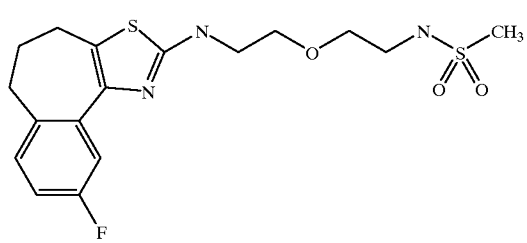 | 66 | |

-continued

| EXAMPLE No. | STRUCTURE | $K_i$, nM hNPY-5 | $K_i$, nM hNPY-1,2,4 |
|---|---|---|---|
| 58 | 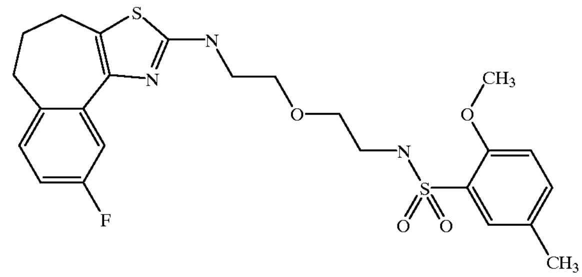 | 3 | |
| 59 | 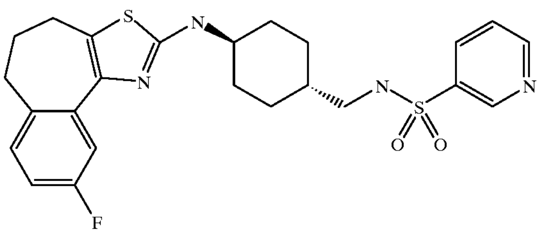 | 2.3 | |
| 60 | 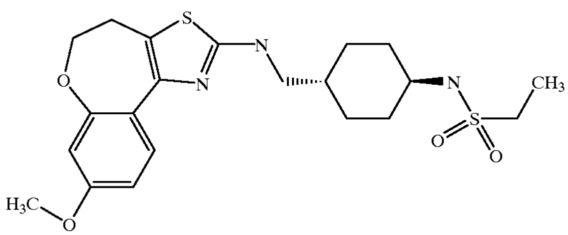 | 31 | |
| 61 | 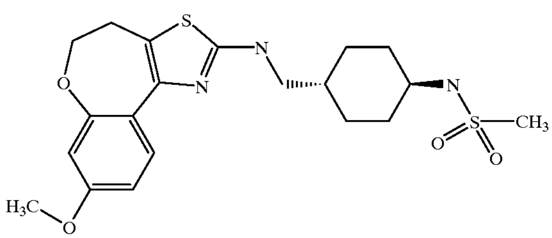 | 162 | |
| 62 | 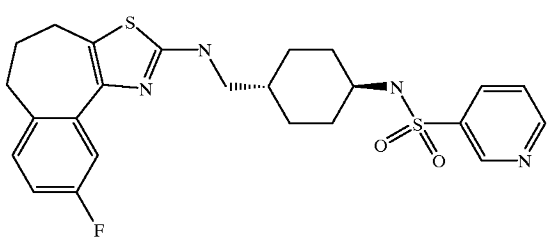 | 1.8 | |
| 63 | 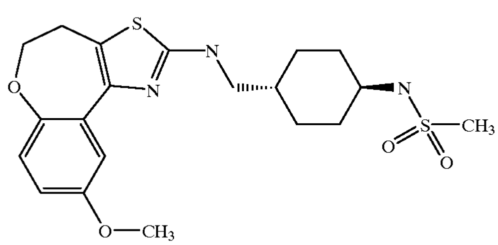 | 31 | |

-continued

| EXAMPLE No. | STRUCTURE | $K_i$, nM hNPY-5 | $K_i$, nM hNPY-1,2,4 |
|---|---|---|---|
| 64 | 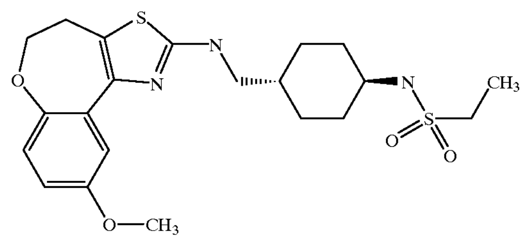 | 12.2 | |
| 65 | 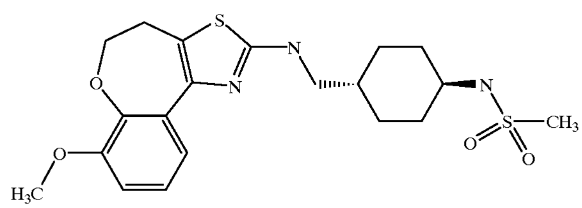 | 11.6 | |
| 66 | 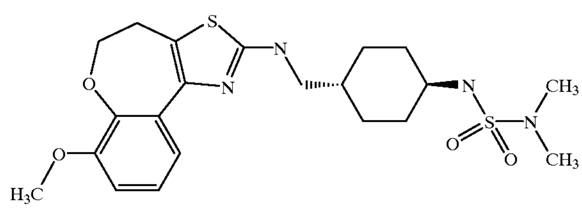 | 2 | |
| 67 | 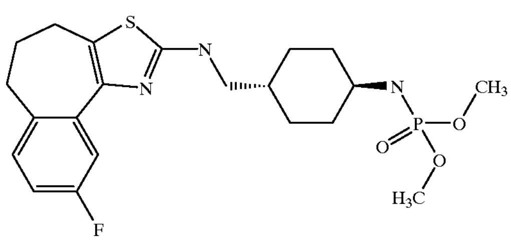 | 5.5 | |
| 68 | 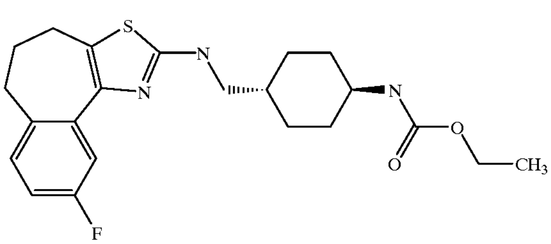 | 4 | |
| 69 | 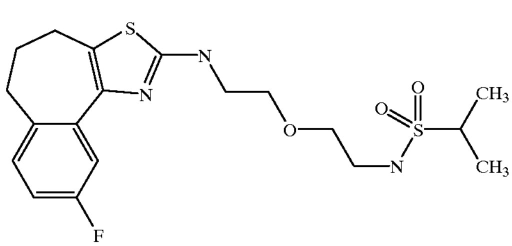 | 4.1 | |

-continued

| EXAMPLE No. | STRUCTURE | $K_i$, nM hNPY-5 | $K_i$, nM hNPY-1,2,4 |
|---|---|---|---|
| 70 | 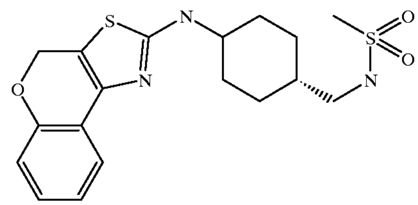 | 21 | |
| 71 | 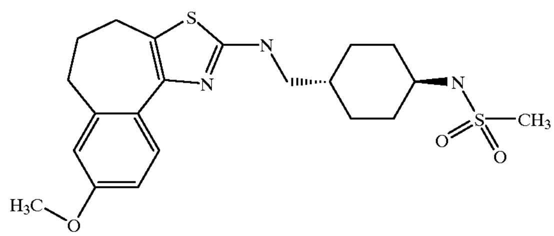 | 2.5 | |
| 72 | 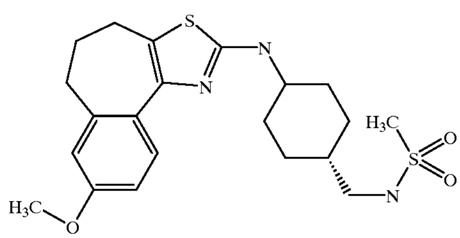 | 22 | |
| 73 | 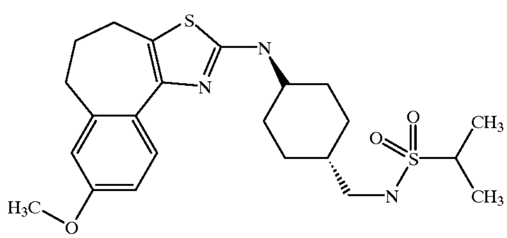 | 8.7 | |
| 74 | 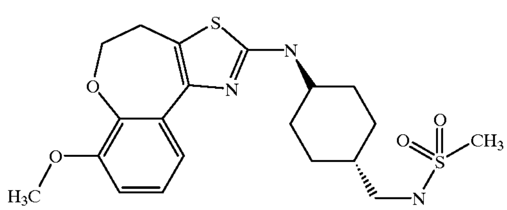 | 37 | |
| 75 | 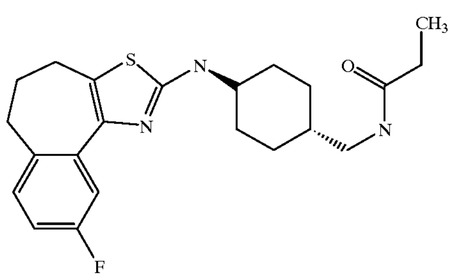 | 36 | |

-continued

| EXAMPLE No. | STRUCTURE | $K_i$, nM hNPY-5 | $K_i$, nM hNPY-1,2,4 |
|---|---|---|---|
| 76 | 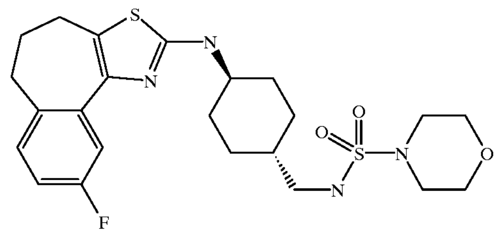 | | 4.1 |
| 77 | 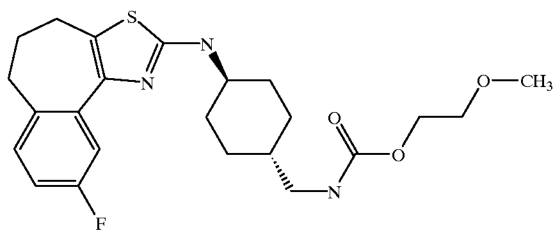 | | 14.6 |
| 78 | 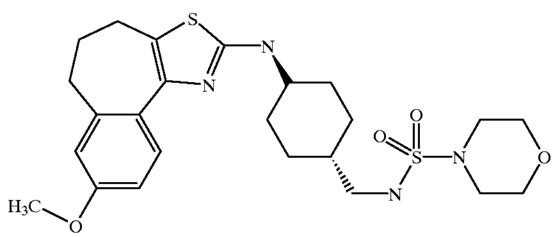 | | 6 |
| 79 | 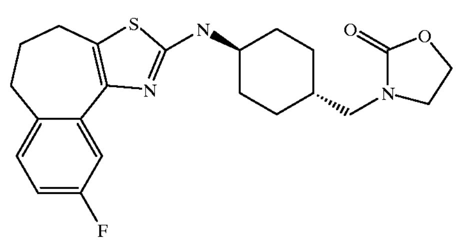 | | 20 |
| 80 | 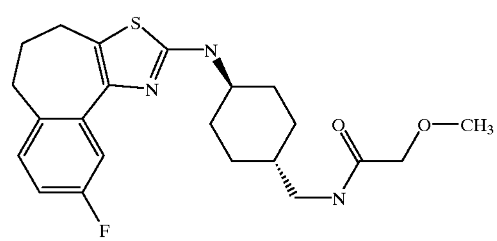 | | 33 |
| 81 | 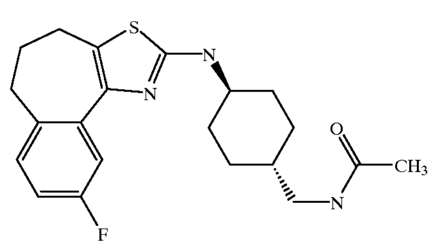 | | 62 |

-continued

| EXAMPLE No. | STRUCTURE | $K_i$, nM hNPY-5 | $K_i$, nM hNPY-1,2,4 |
|---|---|---|---|
| 82 | 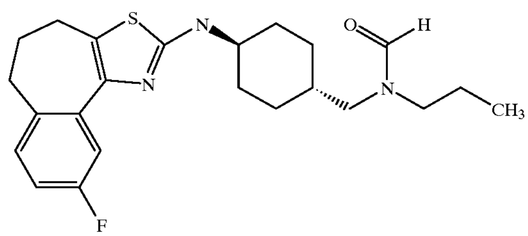 | 11.9 | |
| 83 | 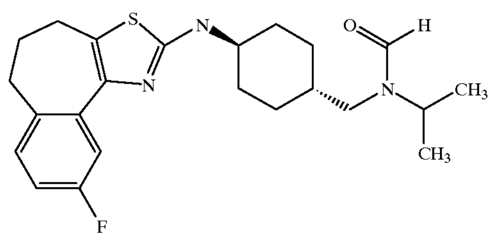 | 12 | |
| 84 | 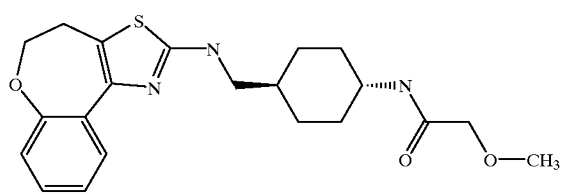 | 40 | |
| 85 | 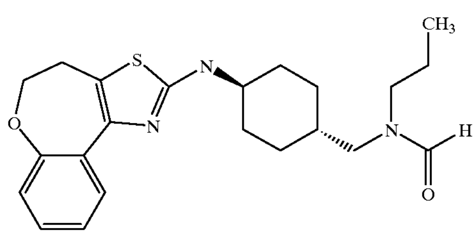 | 150 | |
| 86 | 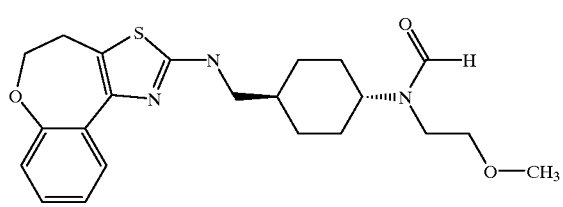 | 68 | |
| 87 | 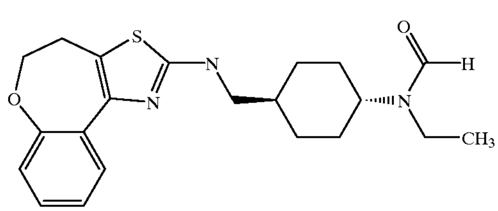 | 86 | |

-continued
| EXAMPLE No. | STRUCTURE | $K_i$, nM hNPY-5 | $K_i$, nM hNPY-1,2,4 |
|---|---|---|---|
| 88 | 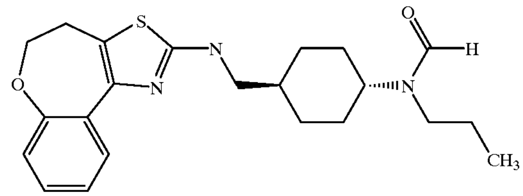 | 36 | |
| 89 | 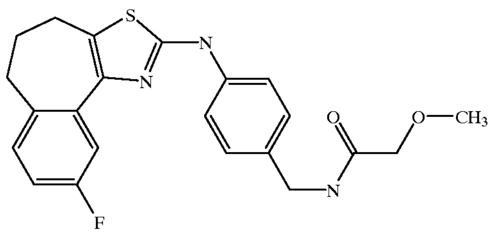 | 9.2 | |
| 90 | 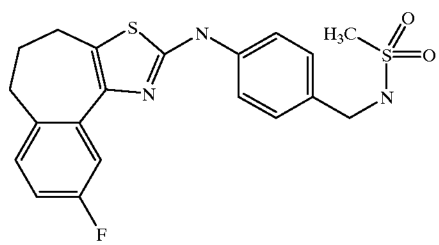 | 5.7 | |
Scheme 1A.
Synthesis of Thioureas
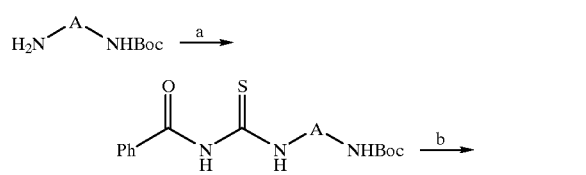
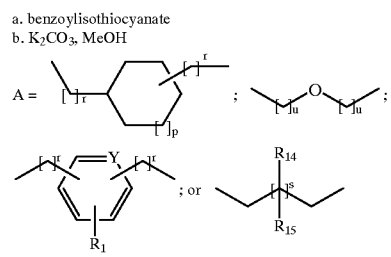
a. benzoylisothiocyanate
b. K$_2$CO$_3$, MeOH
Scheme 1B.
Synthesis of Thioureas
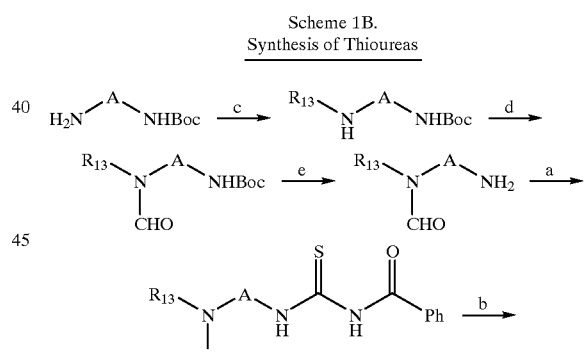
a. Benzoylisothiocyanate
b. K$_2$CO$_3$, MeOH
c. alkyl halide or acyl halide followed by borane reduction
d. formylating agent such as 1H-benzotriazole-1-carboxaldehyde
e. HCl or TFA
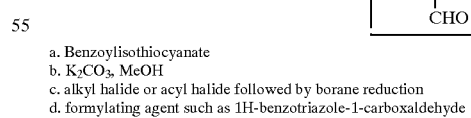
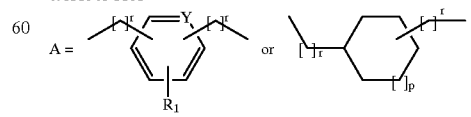

Scheme 1C. Synthesis of Thioureas

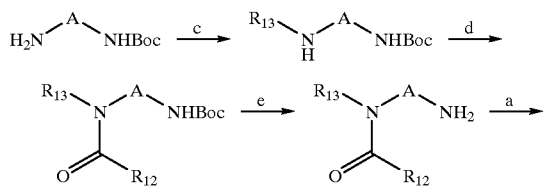

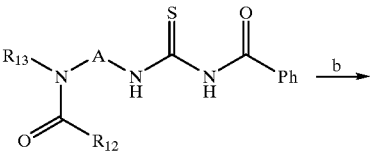

a. Benzoylisothiocyanate
b. K$_2$CO$_3$, MeOH
c. alkyl halide or acyl halide followed by borane reduction
d. R$_{12}$COCl
e. HCl or TFA

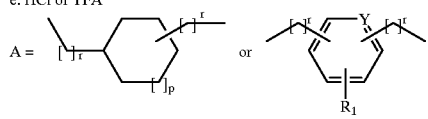

Scheme 1D. Synthesis of Thioureas

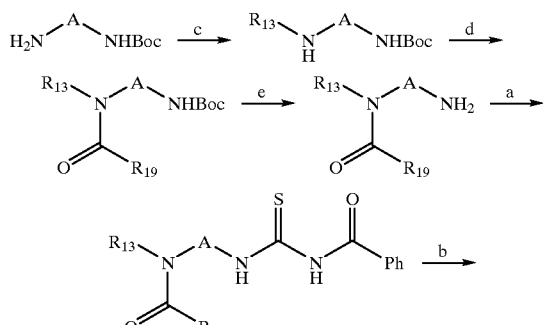

a. benzoylisothiocyanate
b. K$_2$CO$_3$, MeOH
c. alkyl halide or acyl halide followed by borane reduction
d. R$_{19}$COCl
e. HCl or TFA

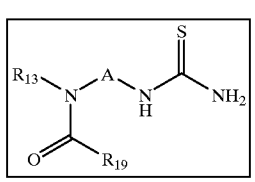

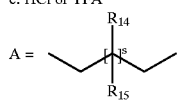

Scheme 1E. Synthesis of Thioureas

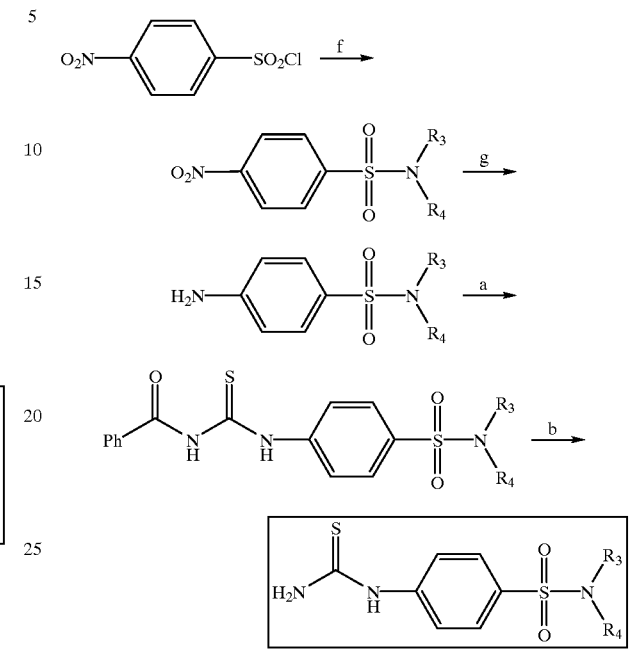

a. benzoylisothiocyanate
b. K$_2$CO$_3$, MeOH
f. HNR$_3$R$_4$
g. reduction

Scheme 2A Synthesis of Bromoketones

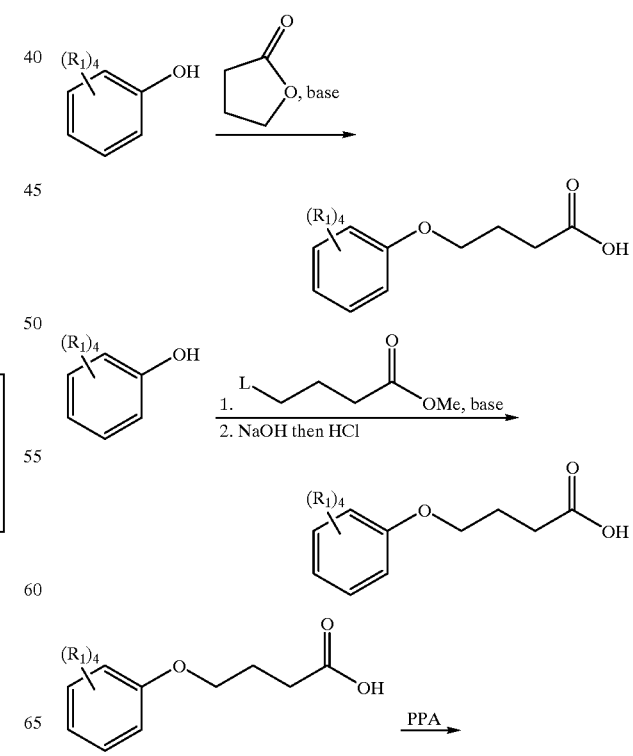

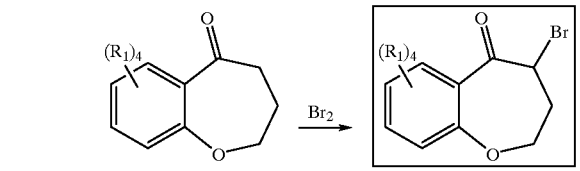
L = leaving group such as Br
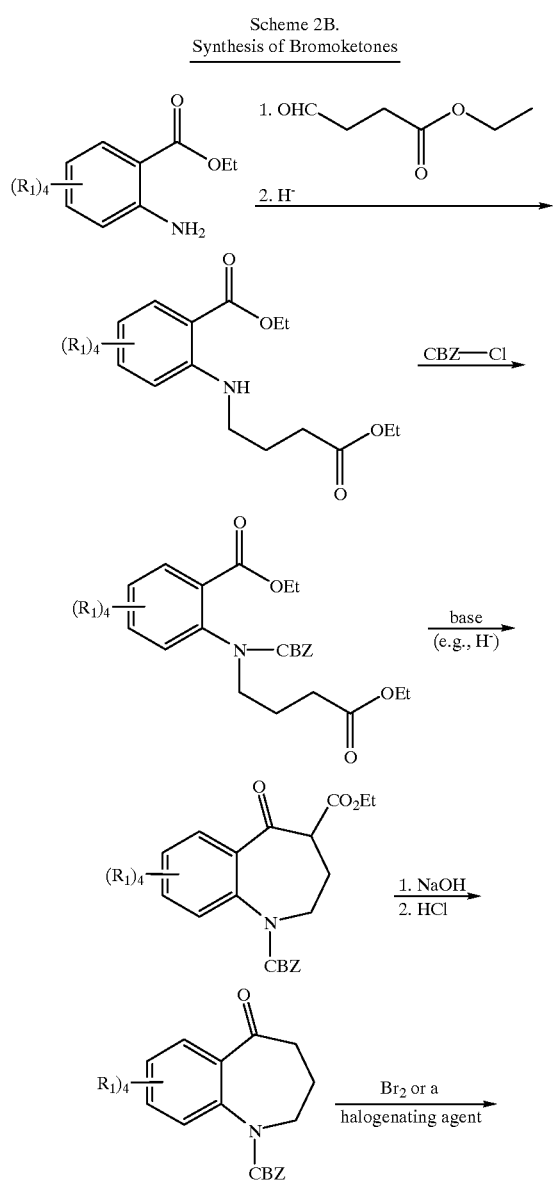
Scheme 2B.
Synthesis of Bromoketones
Scheme 2C.
Synthesis of Bromoketones
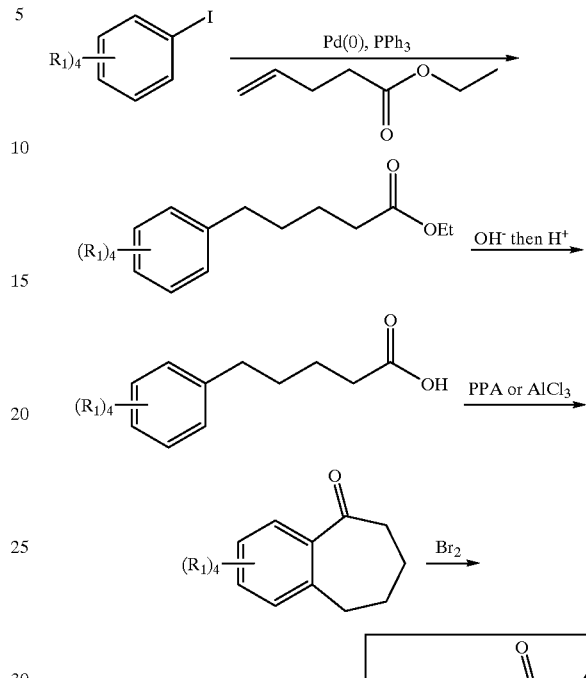
Scheme 3A.
Synthesis of the Tricycles
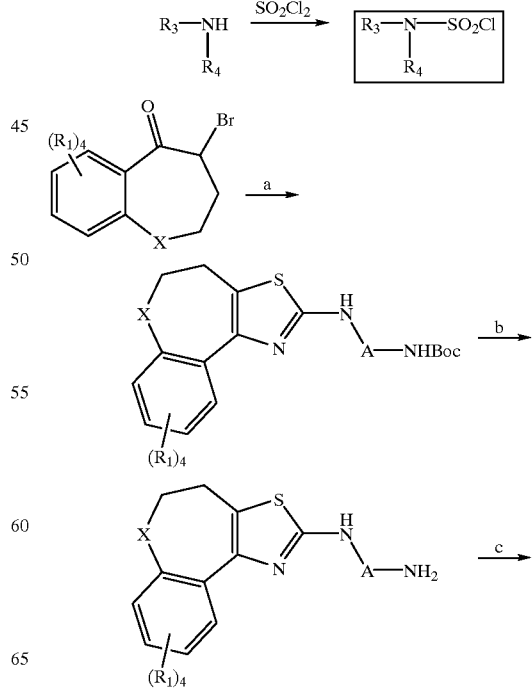

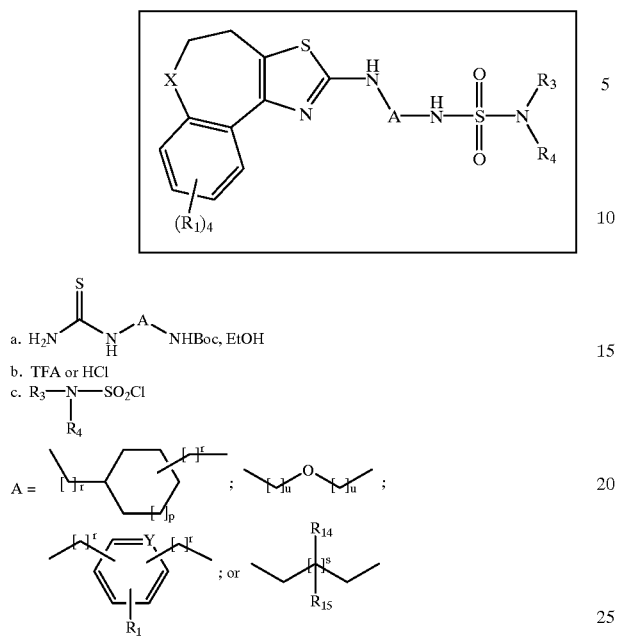
Scheme 3B.
Synthesis of the Tricycles
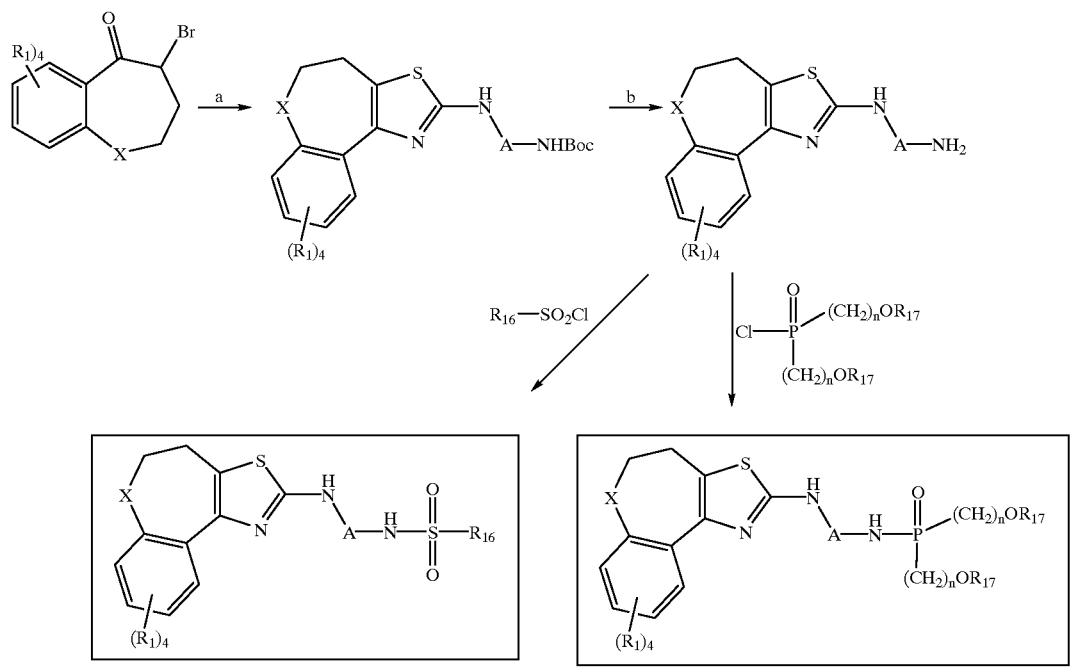
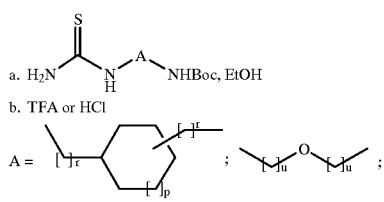

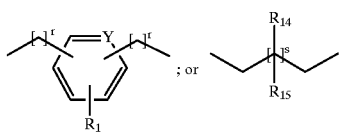
Scheme 3C.
Synthesis of the Tricycles
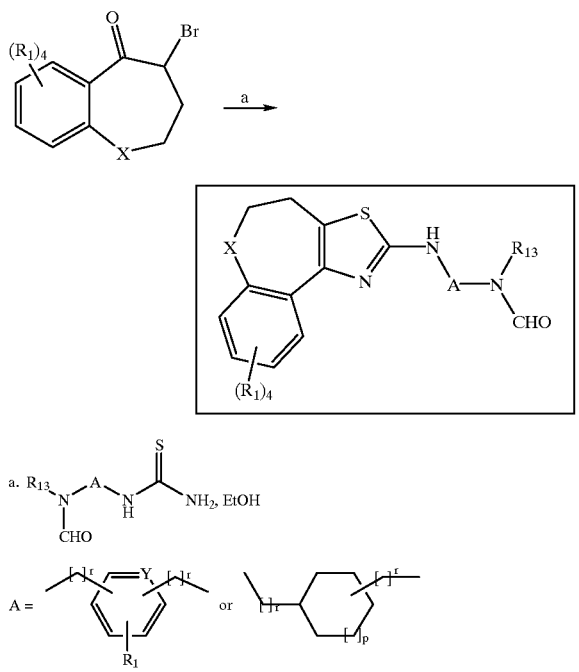
Scheme 3D.
Synthesis of the Tricycles
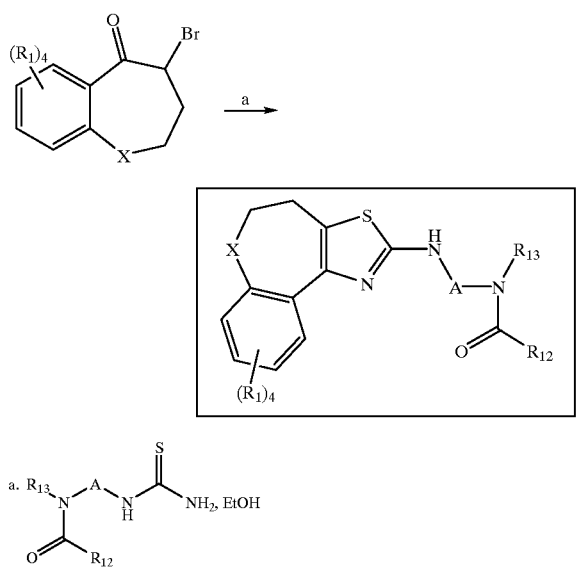
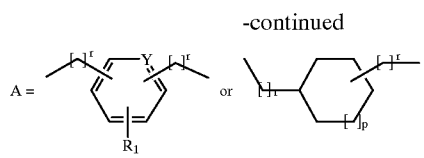
Scheme 3E.
Synthesis of the Tricycles
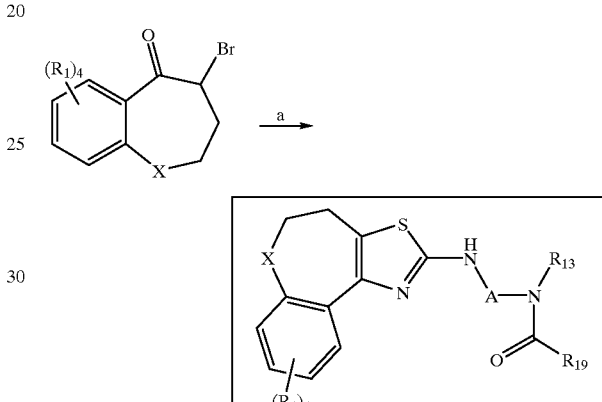
Scheme 3F.
Synthesis of the Tricycles
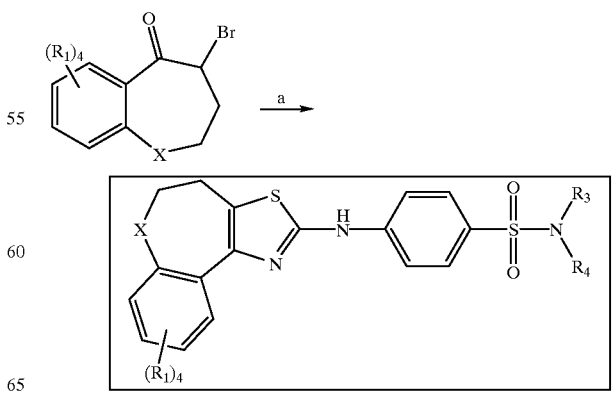

-continued
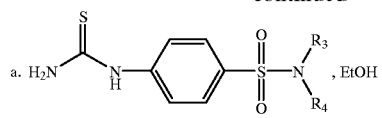
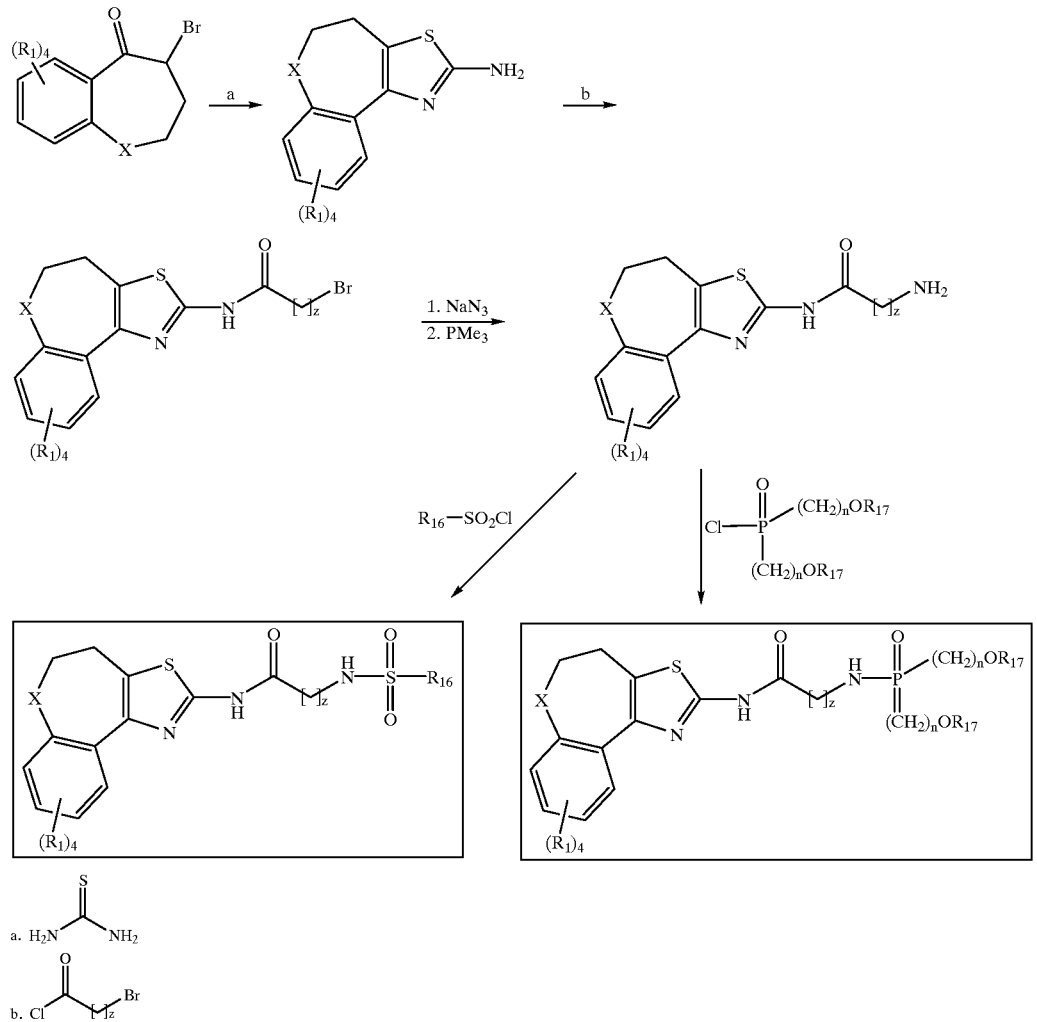
Scheme 3G.
Synthesis of the Tricycles
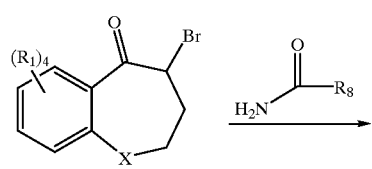
Scheme 4A.
Synthesis of Tricycles
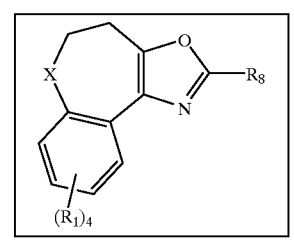
-continued

Scheme 4B.
Synthesis of Tricycles

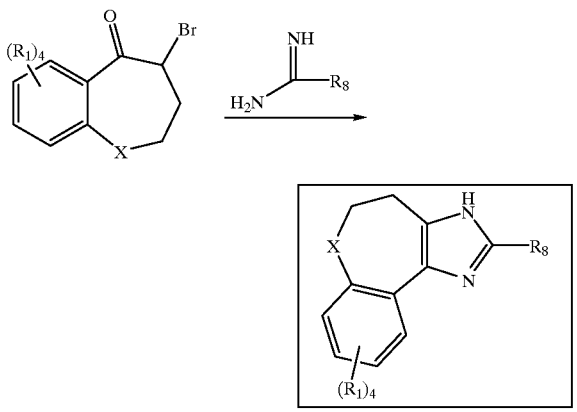

Scheme 5. Transamination of Sulfonylureas

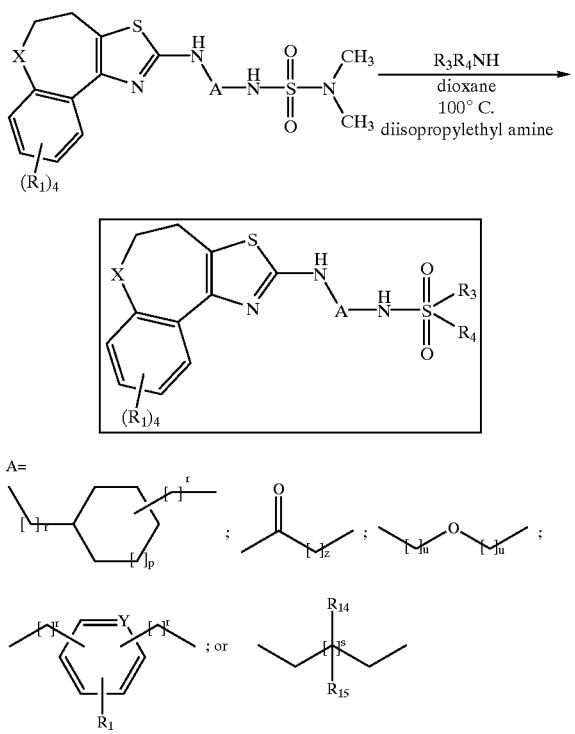

Scheme 6: Synthesis of Side Chains

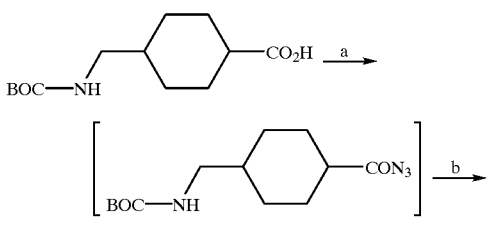

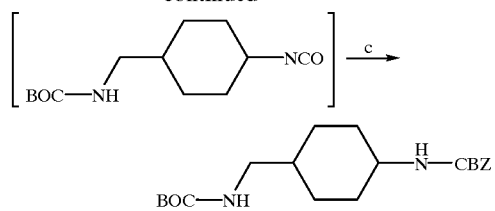

a. Diphenylphosphoryl azide, triethylamine, toluene;
b. heat; c. HOCH$_2$Ph

Functional Assay Results

The functional in vitro activity of several compounds were characterized using a radioimmunoassay of cAMP, the results of which are summarized in Table 2.

TABLE 2

Functional Antagonism Data

| Example # | K$_i$ (h NPY-5), nM | pK$_b$ |
|---|---|---|
| 1 | 2.1 | 7.9 |
| 3 | 4.5 | 8.5 |
| 4 | 19.5 | 8.6 |
| 11 | 6.4 | 8.5 |
| 15 | 3.2 | 8.6 |
| 20 | 0.3 | 8.3 |
| 34 | 33.5 | 7.2 |
| 43 | 4.4 | 7.8 |
| 44 | 2.3 | 8.8 |
| 50 | 15.3 | 8.1 |
| 79 | 20.1 | 7.9 |
| 80 | 32.9 | 7.4 |

REFERENCES

Balasubramaniam, A., Sheriff, S., Johnson, M. E., Prabhakaran, M., Huang, Y., Fischer, J. E., and Chance, W. T. (1994). [D-Trp$^{32}$]Neuropeptide Y: A competitive antagonist of NPY in rat hypothalamus. *J. Med. Chem.* 37: 311–815.

Bradford, M. M. (1976). A rapid and sensitive method for the quantitation of microgram quantities of protein utilizing the principle of protein-dye binding. *Anal. Biochem.* 72: 248–254.

Chabaka, L. M., et al., "Facile Synthesis of 2-Furyl-, 2-Pyrrolyl-, 2-Imidazolyl- and Pyrrolo-Azoles from 2-Substituted Methylazoles." *Pol. J. Chem.* (1994) 68(7): 1317–1325.

Clark, J. T., Kalra, P. S., Crowley, W. R., and Kalra, S. P. (1984). Neuropeptide Y and human pancreatic polypeptide stimulate feeding behavior in rats. *Endocrinology* 115: 427–429.

Crangk, G. and Foulis, M. J., "Oxazoles from ureas" *J. Med. Chem.* (1971) 14: 1075.

Criscione, L., Rigollier, P., Batzl-Hartmann, C., Rueger, H., Stricker-Krongrad, A., Wyss, P., Brunner, L., Whitebread, S., Yamaguchi, Y., Gerald, C., Heurich, R. O., Walker, M. W., Chiesi, M., Schilling, W., Hofbauer, K. G., Levens, N. (1998) Food intake in free-feeding and energy-deprived lean rats is mediated by the neuropeptide Y5 receptor. *J. Clin. Invest.* 102(12): 2136–45.

Critcher, D. J. and Pattenden, G., "Synthetic Studies Towards Pateamine, a Novel Thiazole-Based 19-Membered Bis-lactone from Mycale sp." *Tetrahedron. Lett.* (1996) 37(50): 9107–9110.

Cullen, B. (1987). Use of eurkaryotic expression technology in the functional analysis of cloned genes. *Methods Enzymol.* 152: 685–704.

De Kimpe, N., et al., "Synthesis of 2-Imino-4-thiazolines, 2-Imino-4-alkoxythiazolidines, Thiazoles, and 4-Imidazolin-2-ones from alpha-Halomethyl Ketimines.", *J. Heterocycl. Chem.* (1996) 33(4): 1179–1183.

Demchenko, A. M., et al., "Preparation and Application of alpha-Bromomono- and -bisdifluoromethoxyacetophenones in the Course of Synthesis of Polymethyleneimidazoles Containing a Bridge Nitrogen Atom", *Khim. Geterotsikl. Soedin.* (1997) 10: 1371–1376.

Di Fabio, R. and Pentassuglia, G., "Novel Synthesis of Ethyl 3-(Bromoacetyl)-4,6-dichloro-1H-indole-2-carboxylate as Useful Intermediate in the Preparation of Potential Glycine Site Antagonists", *Synth. Commun.* (1998) 28(1): 51–60.

Dryden, S., Frankish, H., Wang, Q., and Williams, G. (1994). Neuropeptide Y and energy balance: one way ahead for the treatment of obesity? *Eur. J. Clin. Invest.* 24: 293–308.

Dumont, Y., Martel, J.-C., Fournier, A., St-Pierre, S., and Quirion, R. (1992). Neuropeptide Y and neuropeptide Y receptor subtypes in brain and peripheral tissues. *Progress in Neurobiology* 38: 125–167.

Eva, C., Oberto, A., Sprengel, R. and Genazzani, E. (1992). The murine NPY-1 receptor gene: structure and delineation of tissue specific expression. *FEBS lett.* 314: 285–288.

Eva, C., Keinanen, K., Monyer, H., Seeburg, P., and Sprengel, R. (1990). Molecular cloning of a novel G protein-coupled receptor that may belong to the neuropeptide receptor family. *FEBS Lett.* 271: 80–84.

Friedman, B. S., et al., "Thiazoles from thioamides", *J. Am. Chem. Soc.* (1937) 59: 2262.

Hammar, W. J. and Rustad, M. A., "Oxazoles from alpha-bromoketones" *J. Heterocycl. Chem.* (1981) 18: 885.

Herzog, H., Hort, Y. J., Ball, H. J., Hayes, G., Shine, J., and Selbie, L. (1992). Cloned human neuropeptide Y receptor couples to two different second messenger systems. *Proc. Natl. Acad. Sci. USA* 89: 5794–5798.

Kalra, S. P., Dube, M. G., Fournier, A., and Kalra, P. S. (1991). Structure-function analysis of stimulation of food intake by neuropeptide Y: Effects of receptor agonists. *Physiology & Behavior* 50: 5–9.

Kearney, P. C., et al., "Solid-Phase Synthesis of 2-Aminothiazoles", *J. Org. Chem.* (1998) 63(1): 196–200.

Larhammar, D., Blomqvist, A. G., Yee, F., Jazin, E., Yoo, H., and Wahlestedt, C. (1992). Cloning and functional expression of a human neuropeptide Y/peptide YY receptor of the Y1type. *J. Biol. Chem.* 267: 10935–10938.

Levine, A. S., and Morley, J. E. (1984). Neuropeptide Y: A potent inducer of consummatory behavior in rats. *Peptides* 5: 1025–1029.

Little, T. L. and Webber, S. E., "A Simple and Practical Synthesis of 2-Aminoimidazoles" *J. Org. Chem.* (1994) 59(24): 7299–7305.

Marchetti, E., et al., "Oxazoles from ureas" *J. Med. Chem.* (1968) 11: 1092.

Michel, M. C. (1991). Receptors for neuropeptide Y: multiple subtypes and multiple second messengers. *Trends Pharmacol.* 12: 389–394.

Nagao, Y., et al., "Novel Nonprostanoid Prostacyclin (PGI2) Mimetics with Heterocyclic Moiety", *Heterocycles* (1996) 42(2): 517–523.

Novikova, A. P., et al., "Synthesis and Properties of 1,3,4-Thiadiazine Derivatives. Part 1. Condensation of Substituted Phenacyl Bromides and Bromoacetylpyridines with Thiosemicarbazide", *Khim. Geterotsikl. Soedin.* (1991) (6): 843–846.

Pathak, V. N., et al., "Synthesis of Some New Fluorine Containing Oxazoles, Oxadiazoles, Thiadiazoles and Triazines"; *J. Indian Chem. Soc.* (1993) 70(6): 539–542.

Plazzi, P. V., et al., "Heteroarylaminoethyl and Heteroarylthioethylimidazoles. Synthesis and H3-Receptor Affinity", *Eur. J. Med. Chem.* (1995) 30(11): 881–889.

Sahu, A., and Kalra, S. P. (1993). Neuropeptidergic regulation of feeding behavior (neuropeptide Y). *Trends Endocrinol. Metab.* 4: 217–224.

Stanley, B. G., and Leibowitz, S. F. (1984). Neuropeptide Y: Stimulation of feeding and drinking by injection into the paraventricular nucleus. *Life Sci.* 35: 2635–2642.

Stanley, B. G., Magdalin, W., Seirafi, A., Nguyen, M. M., and Leibowitz, S. F. (1992). Evidence for neuropeptide Y mediation of eating produced by food deprivation and for a variant of the $Y_1$ receptor mediating this peptide's effect. *Peptides* 13: 581–587.

Wahlestedt, C., Edvinsson, L., Ekblad, E., and Hakanson, R. Effects of neuropeptide Y at sympathetic neuroeffector junctions: Existence of $Y_1$ and $Y_2$ receptors. In: *Neuronal messengers in vascular function*, Fernstrom Symp. No 10., pp. 231–242. Eds A. Nobin and C. H. Owman. Elsevier: Amsterdam (1987).

Wahlestedt, C., and Reis, D. J. (1993). Neuropeptide Y-Related Peptides and Their Receptors—Are the Receptors Potential Therapeutic Targets? *Ann. Rev. Pharmacol. Tox.* 32: 309–352.

Zhao, Z., et al., "Synthesis of trans-4-Alkenyloxazoles" *Tetrahedron. Lett.* (1991) 32(13): 1609–1612.

What is claimed is:

1. A compound having the structure:

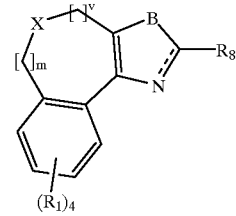

wherein each $R_1$ is independently H, F, Cl, Br, —CN, —OH, —$NO_2$, —$NR_5R_6$, —$SO_2R_5$, —$(CH_2)_nOR_5$, —$(CH_2)_nCONR_5R_6$, —$(CH_2)_nNR_5COR_5$, perfluoroalkyl, polyfluoroalkyl, aminoalkyl, or straight chained or branched $C_1$–$C_7$ alkyl;

wherein $R_5$ is independently H; or straight chained or branched $C_1$–$C_7$ alkyl;

wherein $R_6$ is independently H; or straight chained or branched $C_1$–$C_7$ alkyl;

wherein B is O, NH or S;

wherein X is $CHR_5$, O or $NR_5$;

wherein each n independently is an integer from 0 to 6 inclusive;

wherein $R_8$ is

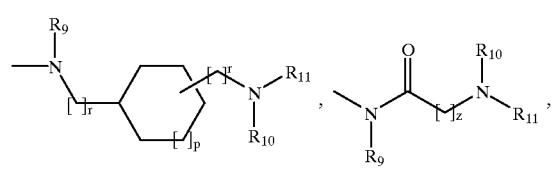

-continued

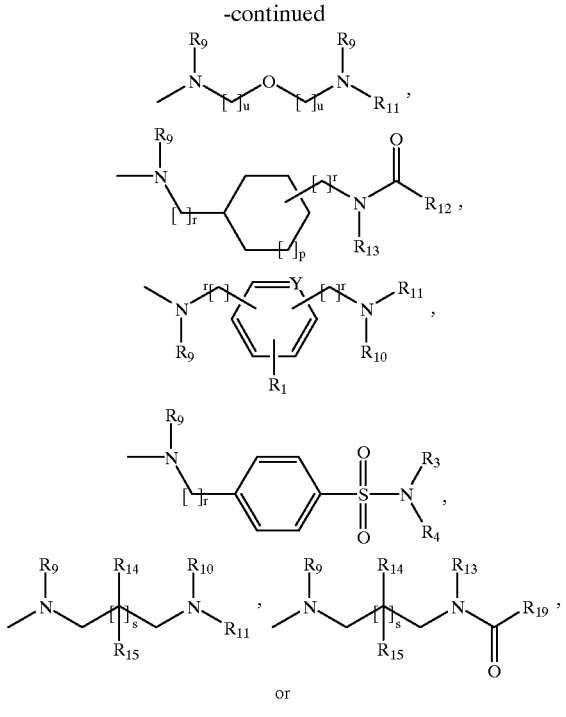

wherein Y is C or N;
wherein $R_7$ is independently straight chained or branched $C_1$–$C_7$ alkyl;
wherein $R_9$ is independently H; or straight chained or branched $C_1$–$C_4$ alkyl;
wherein $R_{10}$ is independently H; or straight chained or branched $C_1$–$C_4$ alkyl;
wherein $R_{11}$ is

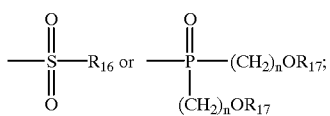

wherein $R_{12}$ is H, straight chained or branched $C_1$–$C_7$ alkyl, $(CH_2)_nOR_{17}$, or $O(CH_2)_uOR_{17}$; provided that when X is O, $R_{12}$ cannot be methyl; —wherein $R_{13}$ is independently H; —$(CH_2)_uOR_5$; —$(CH_2)_tCONR_5R_6$; —$(CH_2)_uNR_5COR_5$; —$(CH_2)_tCOR_7$; —$(CH_2)_tCO_2R_5$; —$(CH_2)_uNR_5R_6$; —$(CH_2)_uCN$; straight chained or branched $C_1$–$C_7$ alkyl; $C_1$–$C_7$ alkyl in which the $C_2$–$C_7$ atoms may be optionally substituted with one or more F or Cl; $C_3$–$C_7$ cycloalkyl-$C_1$–$C_7$ alkyl; straight chained or branched $C_2$–$C_7$ alkenyl or alkynyl; or $C_3$–$C_7$ cycloalkyl; phenyl or $C_1$–$C_6$ phenylalkyl; wherein the phenyl or $C_1$–$C_6$ phenylalkyl may be substituted with one or more of F, Cl, —CN, —$NO_2$, —$NR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl;

or $R_{12}$ and $R_{13}$ together with the amide linkage to which they are attached are pyrrolidinonyl, piperidonyl, or oxazolidinonyl; provided that when X is O, $R_{12}$ and $R_{13}$ cannot be oxazolidinonyl;

wherein $R_{14}$ is H; straight chained or branched $C_1$–$C_4$ alkyl; F; or —$(CH_2)_rOR_5$;

wherein $R_{15}$ is H, straight chained or branched $C_1$–$C_4$ alkyl, or F;

with the proviso that when $R_{14}$ is —OH, $R_{15}$ cannot be F;

wherein $R_{16}$ is $NR_3R_4$, perfluoroalkyl, unsubstituted straight chained or branched $C_1$–$C_7$ alkyl, substituted straight chained or branched $C_2$–$C_7$ alkyl, wherein the $C_2$–$C_7$ alkyl may be substituted with one or more of F, Cl, —CN, —$NR_5R_6$, —$SO_2R_5$, —$(CH_2)_nCOR_7$, —$(CH_2)_nOR_5$, —$(CH_2)_nCONR_5R_6$, —$(CH_2)_nNR_5COR_5$, —$(CH_2)_nCO_2R_5$, —$(CH_2)_nOCF_3$, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl; $C_3$–$C_7$ cycloalkyl or cycloalkenyl; phenyl, heteroaryl, or $C_1$–$C_7$ phenylalkyl, wherein the phenyl, heteroaryl, or $C_1$–$C_7$ phenylalkyl may be substituted with one or more of F, Cl, Br, —CN, —$NO_2$, —$NR_5R_6$, —$(CH_2)_nNR_5COR_5$, —$SO_2R_5$, —$(CH_2)_nCOR_7$, —$(CH_2)_nOR_5$, —$(CH_2)_n$ $CONR_5R_6$, —$(CH_2)_nCO_2R_5$, —$(CH_2)_nSO_2NR_5R_6$, ethylenedioxy, methylenedioxy, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl; quinolinyl, 1-naphthyl, 2-naphthyl, or 2,1,3-benzothiadiazolyl; wherein the quinolinyl, 1-naphthyl, 2-naphthyl or 2,1,3-benzothiadiazolyl may be substituted with one or more of F, Cl, Br, —CN, —$NO_2$, —$NR_5R_6$, —$(CH_2)_nNR_5COR_5$, —$SO_2R_5$, —$(CH_2)_n$ $COR_7$, —$(CH_2)_nOR_5$, —$(CH_2)_nCONR_5R_6$, —$(CH_2)_n$ $CO_2R_5$, —$(CH_2)_nSO_2NR_5R_6$, ethylenedioxy, methylenedioxy, straight chained or branched $C_1$–$C_7$ alkyl, perfluoroalkyl, polyfluoroalkyl, or aminoalkyl;

with the proviso that when X is O and $R_8$ is $NR_9(CH_2)_u$ $O(CH_2)_uNR_{10}R_{11}$, $R_{16}$ cannot be methyl;

wherein $R_3$ is independently H; —$(CH_2)_uOR_5$; —$(CH_2)_t$ $CONR_5R_6$; —$(CH_2)_uNR_5COR_5$; —$(CH_2)_tCOR_7$; —$(CH_2)_tCO_2R_5$; —$(CH_2)_uNR_5R_6$; —$(CH_2)_uCN$; straight chained or branched $C_1$–$C_7$ alkyl; straight chained or branched $C_2$–$C_7$ alkenyl or alkynyl; or $C_3$–$C_7$ cycloalkyl or cycloalkenyl; phenyl, $C_1$–$C_6$ phenylalkyl or $C_1$–$C_6$ heteroarylalkyl; wherein the phenyl, $C_1$–$C_6$ phenylalkyl, or $C_1$–$C_6$ heteroarylalkyl may be substituted with one or more of F, Cl, Br, —CN, —$NO_2$, —$NR_5R_6$, —$SO_2R_5$, —$(CH_2)_nCOR_7$, —$(CH_2)_n$ $OR_5$, —$(CH_2)_nCONR_5R_6$, —$(CH_2)_n$ $NR_5COR_5$, —$(CH_2)_nCO_2R_5$, —$(CH_2)_nSO_2NR_5R_6$, straight chained or branched $C_1$–$C_7$ alkyl, perfluoroalkyl, polyfluoroalkyl, or aminoalkyl, straight chained or branched $C_2$–$C_7$ alkenyl or alkynyl, or $C_3$–$C_7$ cycloalkyl or cycloalkenyl;

wherein $R_4$ is independently H; —$(CH_2)_uOR_5$; —$(CH_2)_t$ $CONR_5R_6$; —$(CH_2)_uNR_5COR_5$; —$(CH_2)_tCOR_7$; —$(CH_2)_tCO_2R_5$; —$(CH_2)_uNR_5R_6$; —$(CH_2)_uCN$; straight chained or branched $C_1$–$C_7$ alkyl; straight chained or branched $C_2$–$C_7$ alkenyl or alkynyl; or $C_3$–$C_7$ cycloalkyl or cycloalkenyl; phenyl or $C_1$–$C_6$ phenylalkyl; wherein the phenyl or $C_1$–$C_6$ phenylalkyl may be substituted with one or more of F, Cl, Br, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

or R$_3$ and R$_4$ taken together with the nitrogen atom to which they are attached are 1-azetidinyl, 1-pyrrolidinyl, 1-piperidinyl, or 1H-azepanyl, wherein the 1-azetidinyl, 1-pyrrolidinyl, 1-piperidinyl, or 1H-azepanyl is substituted with one or more of F, —CN, —(CH$_2$)$_n$NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl, or phenyl or heteroaryl; wherein if —(CH$_2$)$_n$NR$_5$R$_6$, —(CH$_2$)$_n$OR$_5$, or —(CH$_2$)$_n$NR$_5$COR$_5$ are in the 2-position, then n is not 0; wherein the phenyl or heteroaryl may be substituted with one or more of F, Cl, Br, —CN, —NO$_2$, —NR$_5$R$_6$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$NR$_5$COR$_5$, —(CH$_2$)$_n$CO$_2$R$_5$, —(CH$_2$)$_n$SO$_2$NR$_5$R$_6$, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

or R$_3$ and R$_4$ taken together with the nitrogen atom to which they are attached are morpholinyl, thiomorpholinyl, [1,4]oxazepanyl, [1,4]thiazepanyl, piperazinyl, or [1,4]diazepanyl, wherein the morpholinyl, thiomorpholinyl, [1,4]oxazepanyl, [1,4]thiazepanyl, piperazinyl, or [1,4]diazepanyl is optionally substituted with straight chained or branched C$_1$–C$_5$ alkyl or (CH$_2$)$_t$OR$_5$; and wherein the nitrogen atom of the piperazinyl or [1,4]diazepanyl ring may be optionally substituted with —(CH$_2$)$_u$OR$_5$; —COR$_5$; straight chained or branched C$_1$–C$_5$ alkyl; or phenyl; wherein the phenyl may be substituted with one or more of F, Cl, Br, —CN, —NO$_2$, —NR$_5$R$_6$ —(CH$_2$)$_n$OR$_5$, straight chained or branched C$_1$–C$_3$ alkyl, perfluoroalkyl, polyfluoroalkyl, or aminoalkyl;

wherein R$_{17}$ is H, straight chained or branched C$_1$–C$_4$ alkyl, perfluoroalkyl, or polyfluoroalkyl;

wherein R$_{19}$ is (CH$_2$)$_n$OR$_5$, NR$_5$R$_6$, phenyl, or heteroaryl, wherein the phenyl or heteroaryl may be substituted with one or more of F, Cl, Br, —CN, —NO$_2$, —NR$_5$R$_6$, —(CH$_2$)$_n$NR$_5$COR$_5$, —SO$_2$R$_5$, —(CH$_2$)$_n$COR$_7$, —(CH$_2$)$_n$OR$_5$, —(CH$_2$)$_n$CONR$_5$R$_6$, —(CH$_2$)$_n$CO$_2$R$_5$, —(CH$_2$)$_n$SO$_2$NR$_5$R$_6$, ethylenedioxy, methylenedioxy, straight chained or branched C$_1$–C$_7$ alkyl, perfluoroalkyl, polyfluoroalkyl, or aminoalkyl, straight chained or branched C$_2$–C$_7$ alkenyl or alkynyl, or C$_3$–C$_7$ cycloalkyl or cycloalkenyl;

wherein m is 0 or 1;

wherein each p independently is an integer from 0 to 2 inclusive;

wherein each r independently is an integer from 0 to 3 inclusive;

wherein each s independently is an integer from 1 to 6 inclusive;

wherein t is an integer from 1 to 4 inclusive;

wherein each u independently is an integer from 2 to 4 inclusive;

wherein v is 1 or 2;

with the proviso that when v is 2, m is 0;

wherein z is an integer from 2 to 7;

or a pharmaceutically acceptable salt thereof.

2. The compound of claim 1 having the structure:

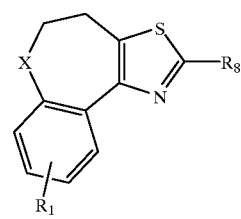

wherein X is CR$_5$R$_6$, O or NR$_5$.

3. The compound of claim 2 having the structure:

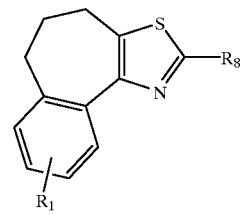

4. The compound of claim 2 having the structure:

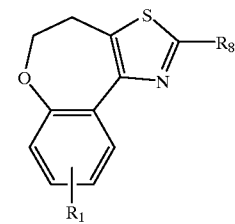

5. The compound of claim 4 having the structure:

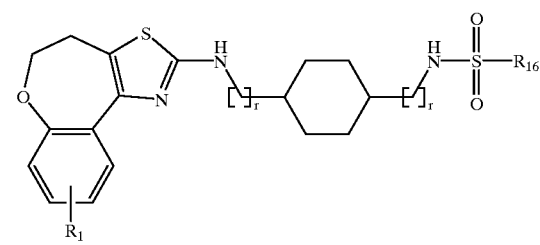

6. The compound of claim 5 wherein the compound is selected from the group consisting of:

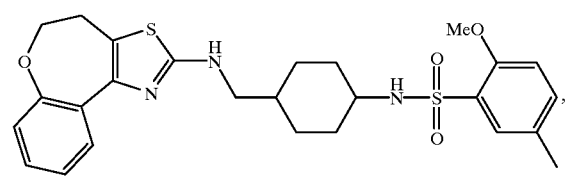

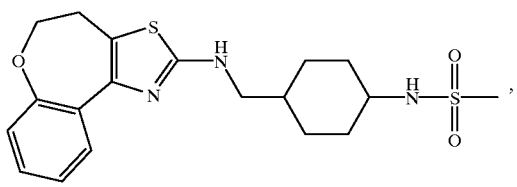
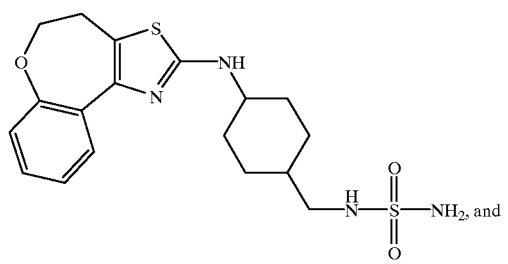
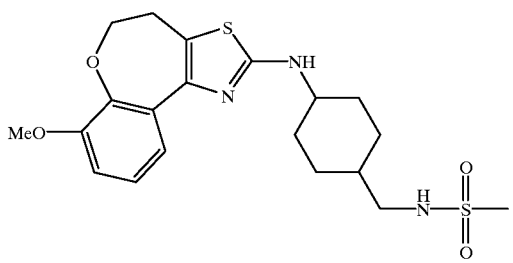
7. The compound of claim 3 having the structure:
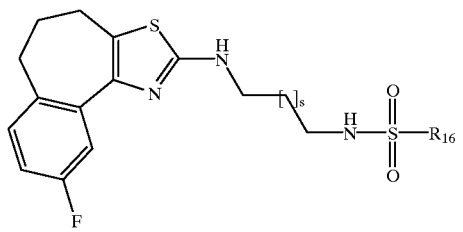
wherein s is 2, 3 or 4.
8. The compound of claim 7 selected from the group consisting of:
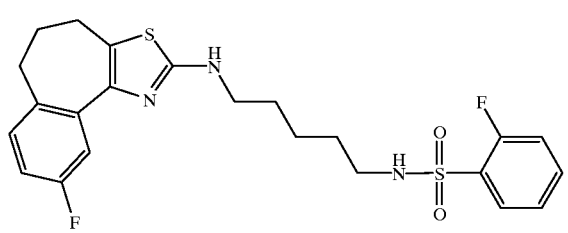
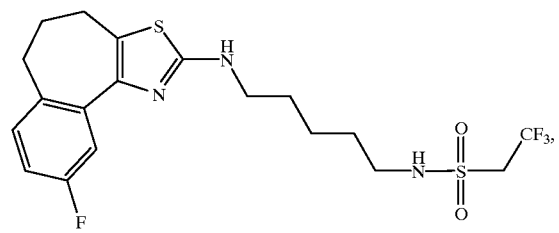
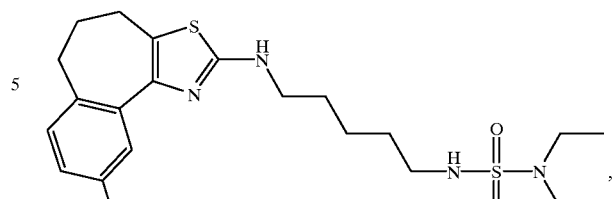
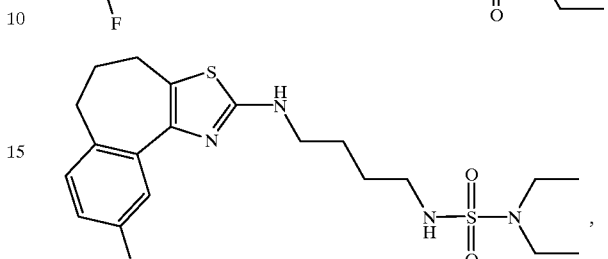
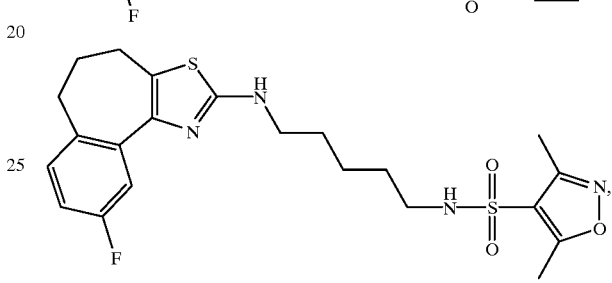
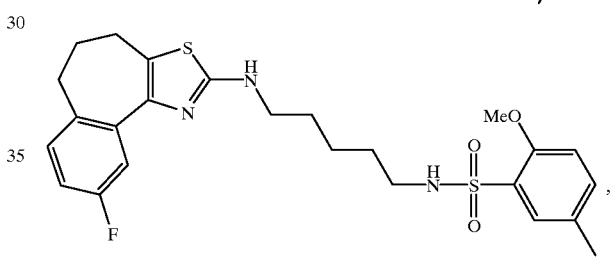
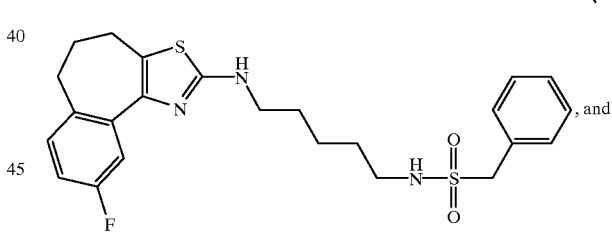
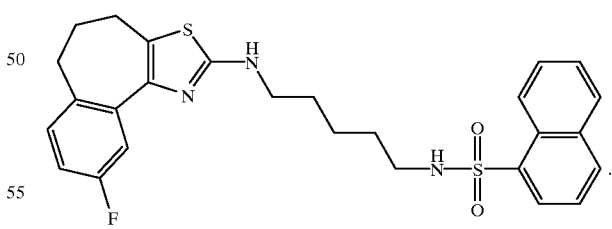

9. The compound of claim 3 having the structure:
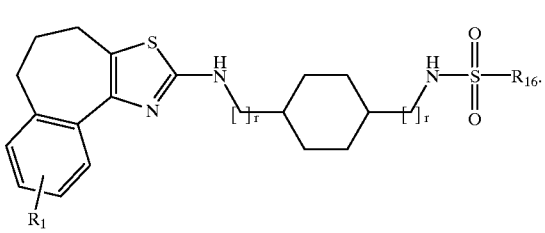
10. The compound of claim 9 selected from the group consisting of:
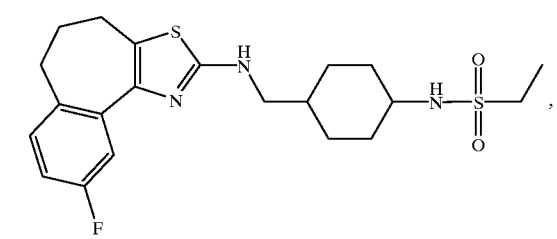
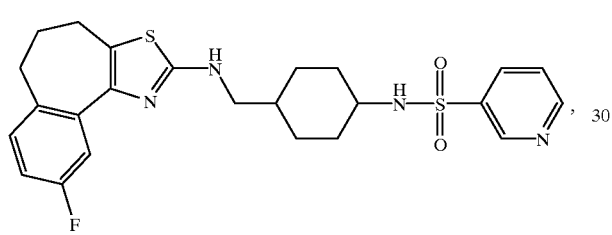
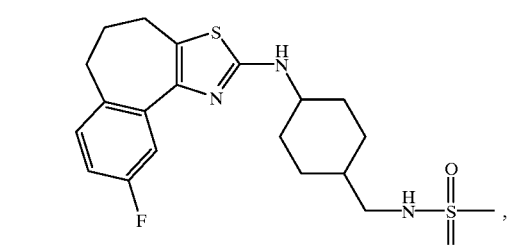
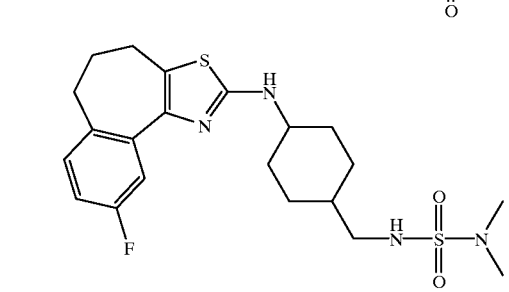
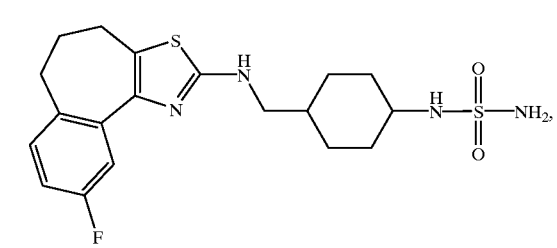
-continued
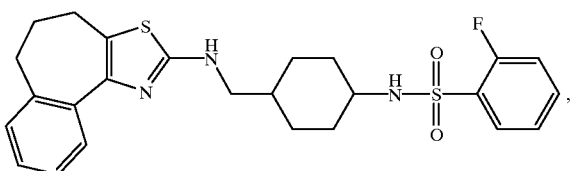
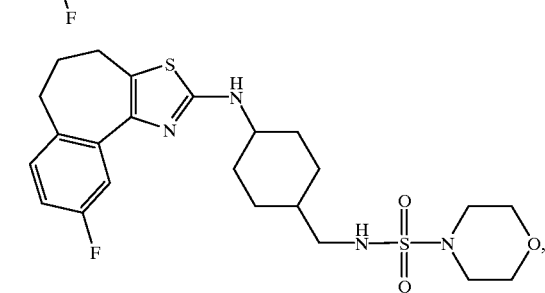
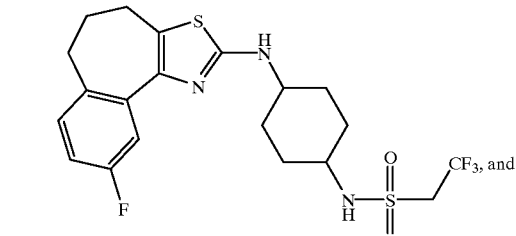
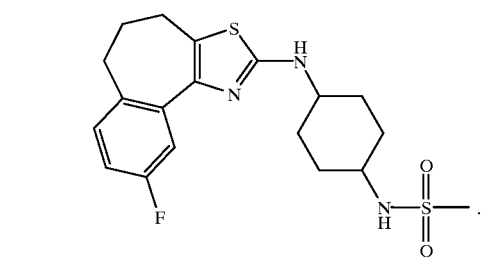
11. The compound of claim 3 having the structure:
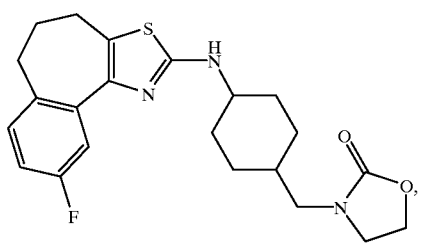

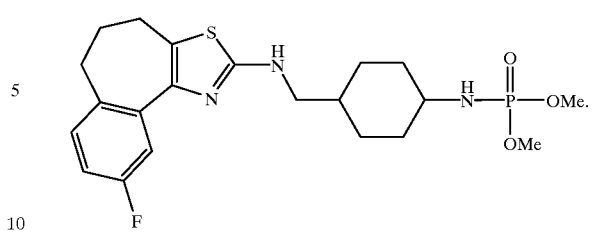

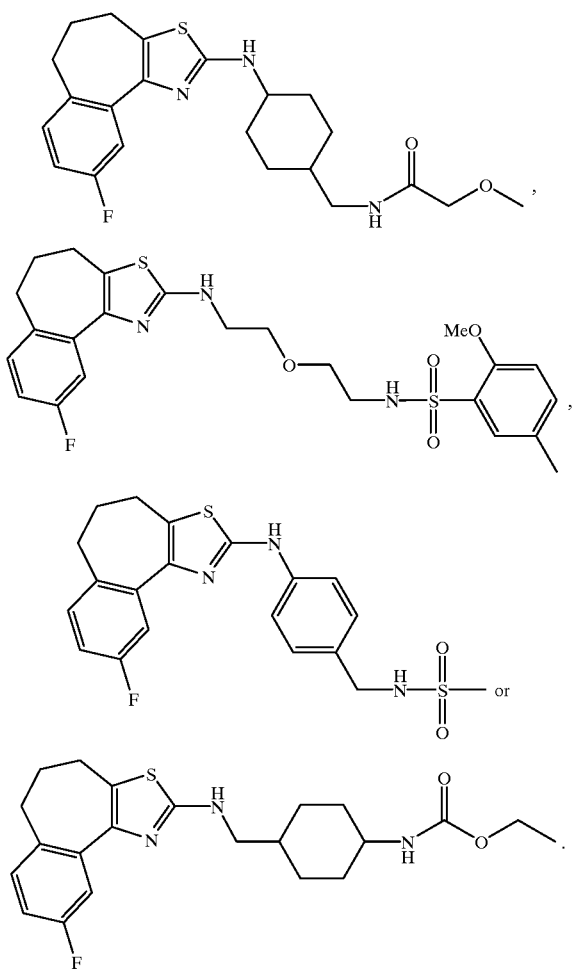

12. The compound of claim 1 selected from the group consisting of:

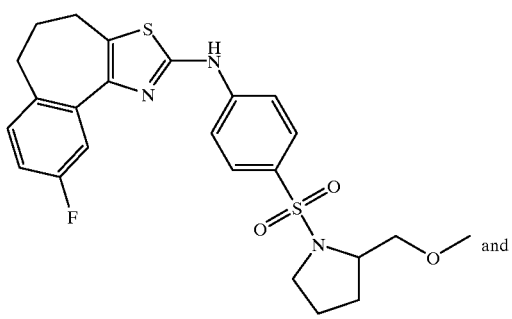

13. A pharmaceutical composition comprising a therapeutically effective amount of the compound of claim 1 and a pharmaceutically acceptable carrier.

14. A pharmaceutical composition of claim 13, wherein the amount of the compound is an amount from about 0.01 mg to about 800 mg.

15. A pharmaceutical composition of claim 14, wherein the amount of the compound is an amount from about 0.01 mg to about 500 mg.

16. A pharmaceutical composition of claim 15, wherein the amount of the compound is an amount from about 0.01 mg to about 250 mg.

17. A pharmaceutical composition of claim 16, wherein the amount of the compound is an amount from about 0.1 mg to about 60 mg.

18. A pharmaceutical composition of claim 17, wherein the amount of the compound is an amount from about 1 mg to about 20 mg.

19. The pharmaceutical composition of claim 13, wherein the carrier is a liquid and the composition is a solution.

20. The pharmaceutical composition of claim 13, wherein the carrier is a solid and the composition is a tablet.

21. The pharmaceutical composition of claim 13, wherein the carrier is a gel and the composition is a suppository.

22. A pharmaceutical composition made by combining a therapeutically effective amount of the compound of claim 1 and a pharmaceutically acceptable carrier.

23. A process for making a pharmaceutical composition comprising combining a therapeutically effective amount of the compound of claim 1 and a pharmaceutically acceptable carrier.

\* \* \* \* \*